(12) United States Patent
Mourich

(10) Patent No.: US 11,911,403 B2
(45) Date of Patent: Feb. 27, 2024

(54) ANTISENSE-INDUCED EXON EXCLUSION IN TYPE VII COLLAGEN

(71) Applicant: Sarepta Therapeutics, Inc., Cambridge, MA (US)

(72) Inventor: Dan V. Mourich, Cambridge, MA (US)

(73) Assignee: Sarepta Therapeutics, Inc., Cambridge, MA (US)

(*) Notice: Subject to any disclaimer, the term of this patent is extended or adjusted under 35 U.S.C. 154(b) by 263 days.

(21) Appl. No.: 17/080,363

(22) Filed: Oct. 26, 2020

(65) Prior Publication Data

US 2021/0161922 A1 Jun. 3, 2021

Related U.S. Application Data

(63) Continuation of application No. 15/578,612, filed as application No. PCT/US2016/035326 on Jun. 1, 2016, now Pat. No. 10,849,917.

(60) Provisional application No. 62/169,454, filed on Jun. 1, 2015.

(51) Int. Cl.
| | |
|---|---|
| C07H 21/02 | (2006.01) |
| A61K 31/70 | (2006.01) |
| C12N 15/113 | (2010.01) |
| C07H 21/04 | (2006.01) |
| A61P 17/00 | (2006.01) |

(52) U.S. Cl.
CPC ............. *A61K 31/70* (2013.01); *A61P 17/00* (2018.01); *C07H 21/02* (2013.01); *C07H 21/04* (2013.01); *C12N 15/113* (2013.01); *C12N 2310/11* (2013.01); *C12N 2310/3145* (2013.01); *C12N 2310/3181* (2013.01); *C12N 2310/3231* (2013.01); *C12N 2310/3233* (2013.01); *C12N 2320/33* (2013.01)

(58) Field of Classification Search
CPC .................... C12N 15/113; C12N 2310/11
See application file for complete search history.

(56) References Cited

U.S. PATENT DOCUMENTS

| | | | |
|---|---|---|---|
| 4,426,330 A | 1/1984 | Sears | |
| 4,534,899 A | 8/1985 | Sears | |
| 5,013,556 A | 5/1991 | Woodle et al. | |
| 5,034,506 A | 7/1991 | Summerton et al. | |
| 5,108,921 A | 4/1992 | Low et al. | |
| 5,142,047 A | 8/1992 | Summerton et al. | |
| 5,166,315 A | 11/1992 | Summerton et al. | |
| 5,185,444 A | 2/1993 | Summerton et al. | |
| 5,213,804 A | 5/1993 | Martin et al. | |
| 5,217,866 A | 6/1993 | Summerton et al. | |
| 5,227,170 A | 7/1993 | Sullivan | |
| 5,264,221 A | 11/1993 | Tagawa et al. | |
| 5,354,844 A | 10/1994 | Beug et al. | |
| 5,356,633 A | 10/1994 | Woodle et al. | |
| 5,395,619 A | 3/1995 | Zalipsky et al. | |
| 5,416,016 A | 5/1995 | Low et al. | |
| 5,417,978 A | 5/1995 | Tari et al. | |
| 5,459,127 A | 10/1995 | Felgner et al. | |
| 5,462,854 A | 10/1995 | Coassin et al. | |
| 5,469,854 A | 11/1995 | Unger et al. | |
| 5,506,337 A | 4/1996 | Summerton et al. | |
| 5,521,063 A | 5/1996 | Summerton et al. | |
| 5,521,291 A | 5/1996 | Curiel et al. | |
| 5,527,528 A | 6/1996 | Allen et al. | |
| 5,534,259 A | 7/1996 | Zalipsky et al. | |
| 5,539,082 A | 7/1996 | Nielsen et al. | |
| 5,543,152 A | 8/1996 | Webb et al. | |
| 5,543,158 A | 8/1996 | Gref et al. | |
| 5,547,932 A | 8/1996 | Curiel et al. | |
| 5,556,948 A | 9/1996 | Tagawa et al. | |
| 5,580,575 A | 12/1996 | Unger et al. | |
| 5,583,020 A | 12/1996 | Sullivan | |
| 5,591,721 A | 1/1997 | Agrawal et al. | |
| 5,595,756 A | 1/1997 | Bally et al. | |
| 5,698,685 A | 12/1997 | Summerton et al. | |
| 5,714,331 A | 2/1998 | Buchardt et al. | |
| 5,719,262 A | 2/1998 | Buchardt et al. | |
| 5,770,713 A | 6/1998 | Imbach et al. | |
| 6,169,079 B1 * | 1/2001 | Bennett | C07H 21/04 435/375 |
| 6,245,747 B1 | 6/2001 | Porter et al. | |
| 6,287,860 B1 | 9/2001 | Monia et al. | |
| 6,670,461 B1 | 12/2003 | Wengel et al. | |
| 6,794,499 B2 | 9/2004 | Wengel et al. | |
| 6,965,025 B2 | 11/2005 | Gaarde et al. | |
| 6,969,400 B2 | 11/2005 | Rhee et al. | |

(Continued)

FOREIGN PATENT DOCUMENTS

| | | |
|---|---|---|
| JP | 2018-518167 A | 7/2018 |
| WO | WO 1993/01286 A2 | 1/1993 |

(Continued)

OTHER PUBLICATIONS

Abes et al. (Journal of Peptide Science, 2008, 14, 455-460).*
Altschul et al. "Gapped BLAST and PSI-BLAST: A New Generation of Protein Database Search Programs", *Nucleic Acids Research* 25:3389 (1997).
Ashman et al., "Sequence requirements for oligodeoxyribonucleotide inhibitory activity", *International Immunology* 17(4):415 (Apr. 2005).
Bauer et al., "Human TLR9 confers responsiveness to bacterial DNA via species-specific CpG motif recoenition", *PNAS* 98(16):9237-9242 (2001).
Benner et al., "Synthetic Biology", *Nature Reviews Genetics* 6:553-543 (2005).

(Continued)

*Primary Examiner* — Amy H Bowman
(74) *Attorney, Agent, or Firm* — Lathrop GPM LLP; Brian C. Trinque

(57) ABSTRACT

The present disclosure relates to antisense oligomers and related compositions and methods for increasing the expression of functional human type VII collagen and methods for treating dystrophic epidermolysis bullosa and related disorders and relates to inducing exclusion of exon 80 in human type VII collagen mRNA.

8 Claims, 8 Drawing Sheets

Specification includes a Sequence Listing.

(56) References Cited

U.S. PATENT DOCUMENTS

| | | |
|---|---|---|
| 6,969,766 B2 | 11/2005 | Kim et al. |
| 7,022,851 B2 | 4/2006 | Kim et al. |
| 7,034,133 B2 | 4/2006 | Wengel et al. |
| 7,053,207 B2 | 5/2006 | Wengel et al. |
| 7,060,809 B2 | 6/2006 | Wengel et al. |
| 7,084,152 B2 | 8/2006 | Beck et al. |
| 7,125,994 B2 | 10/2006 | Kim et al. |
| 7,145,006 B2 | 12/2006 | Kim et al. |
| 7,179,896 B2 | 2/2007 | Kim et al. |
| 7,211,668 B2 | 5/2007 | Kim et al. |
| 7,569,575 B2 | 8/2009 | Sorensen et al. |
| 7,572,582 B2 | 8/2009 | Wengel et al. |
| 7,868,657 B1 | 1/2011 | Cassia |
| 7,943,762 B2 | 5/2011 | Weller et al. |
| 8,779,128 B2 | 7/2014 | Hanson et al. |
| 9,340,783 B2 * | 5/2016 | Hovnanian .......... C12N 15/113 |
| 2003/0045488 A1 | 3/2003 | Brown et al. |
| 2005/0239733 A1 | 10/2005 | Jurk et al. |
| 2005/0288246 A1 | 12/2005 | Iversen et al. |
| 2006/0281677 A1 | 12/2006 | Albarran et al. |
| 2010/0016215 A1 | 1/2010 | Moulton et al. |
| 2011/0269820 A1 | 11/2011 | Singh et al. |
| 2011/0318382 A1 | 12/2011 | Mourich et al. |
| 2012/0171170 A1 | 7/2012 | Collard et al. |
| 2013/0131312 A1 | 5/2013 | Iversen et al. |
| 2014/0275222 A1 | 9/2014 | Stamm et al. |
| 2014/0288155 A1 | 9/2014 | Hovnanian et al. |
| 2015/0344844 A1 | 12/2015 | Better et al. |
| 2016/0355822 A1 | 12/2016 | Uhlmann et al. |
| 2017/0029818 A1 | 2/2017 | de Visser et al. |

FOREIGN PATENT DOCUMENTS

| | | | |
|---|---|---|---|
| WO | WO 1993/24510 A1 | 12/1993 | |
| WO | WO 1994/26764 A1 | 11/1994 | |
| WO | WO 03/040328 A2 * | 5/2003 | .......... C12N 15/113 |
| WO | WO 2004/043977 A2 | 5/2004 | |
| WO | WO 2005/115479 A2 | 12/2005 | |
| WO | WO 2006/028742 A2 | 3/2006 | |
| WO | WO 2007/002390 A2 | 1/2007 | |
| WO | WO 2008/036127 A2 | 3/2008 | |
| WO | WO 2009/008725 A2 | 1/2009 | |
| WO | WO 2009/064471 A1 | 5/2009 | |
| WO | WO 2010/115993 A1 | 10/2010 | |
| WO | WO 2010/120820 A1 | 10/2010 | |
| WO | WO 2010/148249 A1 | 12/2010 | |
| WO | WO 2011/005942 A2 | 1/2011 | |
| WO | WO 2011/150408 A2 | 12/2011 | |
| WO | WO 2012/043730 A1 | 4/2012 | |
| WO | WO 2012/150960 A1 | 11/2012 | |
| WO | WO 2013/053819 A1 | 4/2013 | |
| WO | WO 2013/053928 A1 | 4/2013 | |
| WO | WO 2013/074834 A1 | 5/2013 | |
| WO | WO 2013/086441 A2 | 6/2013 | |
| WO | WO 2013/112053 A1 | 8/2013 | |
| WO | WO 2013/121202 A1 | 8/2013 | |
| WO | WO 2014/108529 A1 | 7/2014 | |
| WO | WO 2016/185041 A1 * | 11/2016 | .......... C12N 15/113 |
| WO | WO 2016/196670 A1 | 12/2016 | |
| WO | WO 2019/079637 A2 | 4/2019 | |

OTHER PUBLICATIONS

Chiu et al., "siRNA Function in RNAi: A Chemical Modification Analysis", *RNA* 9:1034-1048 (2003).
Deveraux et al., "A Comprehensive Set of Sequence Analysis Programs for the VAX", *Nucleic Acids Research* 12:387-395 (1984).
Dokka et al., "Novel Non-Endocytic Delivery of Antisense Oligonucleotides", *Advanced Drug Delivery Reviews* 44:35-49 (2000).
European Search Report in European Application No. 13151106, dated Oct. 14, 2013.
European Search Report in European Application No. 16804357.8, dated Dec. 13, 2018.
Partial European Search Report in European Application No. 13151106, dated Jun. 25, 2015.
GenBank Accession No. CPO18606.1, Feb. 7, 2017 [online]. [Retrieved Feb. 17, 2019]. Retrieved from the Internet <URL: https://www.ncbi.nhu.nih.govinuccore/CPO18606.1t> entire document.
Habermehl et al., Naturstoffchemie. Springer, (2008).
Heil et al., "Species-Specific Recognition of Single-Stranded RNA via Toll-like Receptor 7 and 8", *Science* 303(5663):1526-1529 (2004).
Hirao, "Unnatural Base Pair Systems for DNA/RNA-Based Biotechnology", *Current Opinion in Chemical Biology* 10:622-627 (2006).
International Preliminary Report on Patentability in International Application No. PCT/EP2014/050453 dated Jan. 13, 2014.
International Preliminary Report on Patentability in International Application No. PCT/US2016/035326 dated Jun. 1, 2016.
International Search Report in International Application No. PCT/US2016/035326 dated Aug. 12, 2016.
International Search Report in International Application No. PCT/US2018/056572 dated May 6, 2019.
International Search Report and Written Opinion in International Application No. PCT/EP2014/050453 dated Jan. 13, 2014.
Invitation to Pay Additional Fees and where Applicable, Protest Fee for Application No. PCT/US2018/056572 dated Feb. 19, 2019.
Iyer et al., "The Automated Synthesis of Sulfur-Containing Oligodeoxyribonucleotides Using 3H-1,2-Benzodithiol-3-One 1,1-Dioxide as a Sulfur-Transfer Reagent", *Journal of Organic Chemistry* 55:4693-4699 (1990).
Jurk et al., "Modulating responsiveness of human TLR7 and 8 to small molecule ligands with T-rich phosphorothiate oligodeoxynucleotides", *European Journal of Immunology* 36(7):1815-1826 (2006).
Koller et al., "Trans-Splicing Improvement by the Combined Application of Antisense Strategies", *International Journal of Molecular Sciences* 16:1179-1191 (Jan. 2015).
Kool et al., "Replacing the Nucleobases in DNA with Designer Molecules", *Accounts in Chemical Research* 35:936-943 (2002).
Kruegar et al., "Synthesis and Properties of Size-Expanded DNAs: Toward Designed, Functional Genetic Systems", *Accounts of Chemical Research* 40:141-150 (2007).
Lappalainen et al., "Cationic Liposomes Mediated Delivery of Antisense Oligonucleotides Targeted to HPV 16 E7 mRNA in CaSki Cells", *Antiviral Research* 23:119 (1994).
Lenert et al., "Structural Characterization of the Inhibitory DNA Motif for the Type A (D)-CpG-Induced Cytokine Secretion and NK-Cell Lytic Activity in Mouse Spleen Cells", *DNA and Cell Biology* 22(10):621-631 (Oct. 2003).
Limbach et al., "Summary the Modified Nucleosides of RNA", *Nucleic Acids Research* 22(12):2183-2196 (1994).
Luganini et al "Inhibition of Herpes Simplex Virus Type 1 and Type 2 Infections by Peptide-, Derivatized Dendrimers", *Antimicrob. Agents Chemotherapy* 52:1111-1120 (Jul. 2011).
Makino et al., "Involvement of Tachykinins and NK1 Receptor in the Joint Inflammation with Collagen Type II-Specific Monoclonal Antibody-Induced Arthritis in Mice", *J. Nippon Medical School* 79:129-138 (2012).
Martin et al., "Ein Neuer Zugang Zu 2'-O-Alkylribonucleosiden Und Eigenschaften Deren Oligonucleotide", *Helvetica Chimica Acta* 78:486-504 (1995).
Miyada et al., "Oligomer Hybridization Techniques", *Methods Enzymology* 154:94-107 (1987).
Mourich et al., "Antisense Targeting of cFLIP Sensitizes Activated T Cells to Undergo Apoptosis and Desensitizes Responses to Contact Dermatitis", *Journal of Investigative Dermatology* 129(8):1945-1953 (2009).
Nielsen et al., "Sequence-selective recognition of DNA by strand displacement with a thymine-substituted polyamide", *Science* 254:1497-1500 (1991).
Obika et al., "Synthesis of 2'-O,4'-C-Methyleneuridine and -Cytidine. Novel Bicyclic Nucleosides having a Fixed C3, -Endo Sugar Puckering", *Tetrahedron Letters* 38(50):8735 (1997).

(56) References Cited

OTHER PUBLICATIONS

Obika et al., "Stability and Structural Features of the Duplexes Containing Nucleoside analogues with a fixed N-Type Conformation, 2'-O,4'-C- Mehtyleneribonucleosides", *Tetrahedron Letters* 39:5401 (1997).

Obika et al., "Synthesis and Properties of 3'-Amino-2',4'-BNA, A Bridged Nucleic Acid with a N3'→P5' Phosphoramidate Linkage", *Bioorganic Medicinal Chemistry* 16:9230 (2008).

Pendaries et al., "sIRNA-Mediated Allele-Specific Inhibition of Mutant Type VII Collagen in Dominant Dystrophic Epidermolysis Bullosa", *Journal of Investigative Dermatology* 132:1741-1743 (Feb. 2012).

Requirement for Restriction in U.S. Appl. No. 14/760,791 dated Feb. 23, 2016.

Requirement for Restriction in U.S. Appl. No. 15/244,879 dated Mar. 6, 2017.

Revankar et al., "DNA with Altered Bases," *Comprehensive Natural Products Chemistry* 7(9):313-339 (1999).

Robbins et al., "2'-O-Methyl-Modified RNAs Act as TLR7 Antagonists", *Molecular Therapy* 15(9):1663-1669 (Sep. 2007).

Roemmler et al., "Guanine Modification of Inhibitory Oligonucleotides Potentiates Their Suppressive Function", *International Journal of Medical Microbiology* 302(Suppl. 1):120 (Sep. 2012).

Roemmler et al., "Guanine Modification of Inhibitory Oligonucleotides Potentiates Their Suppressive Function," *The Journal of Immunology* 191(6):3240-3253 (Aug. 2013).

Roller et al., "Blockade of Phosphatidylinositol 3-Kinase (PI3K) .3 PI3KY Reduces IL-17 and Ameliorates Imiquimod-Induced Psoriasis-like Dermatitis", *Journal of Immunology* 189:4612-4620 (2012).

Romesberg et al., "Beyond A, C, G and T: Augmenting Nature's Alphabet", *Current Opinion in Chemical Biology* 7(6):723-733 (2003).

Summerton et al., "Morpholino Antisense Oligomers: Design, Preparation, and Properties", *Antisense and Nucleic Acid Drug Development* 7:187-195 (1997).

Turczynski et al., "Antisense-Mediated Exon Skipping to Reframe Transcripts", *Exon Skipping: Methods and Protocols, Methods in Molecular Biology* 867(15):221-238 (2012).

Turczynski et al., "Exon Skipping Restores Functional Type VII Collagen in Dystrophic Epidermolysis Bullosa", *Journal of Investigative Dermatology* 133(850):S144 (May 2013). (Abstract Only).

Uhlmann et al., "Antisense oligonucleotides: a new therapeutic principle", *Chemical Reviews* 90:543 (1990).

Uhlmann et al., "Antisense Oligomers: A Therapeutic Principle", *Chemical Reviews* 90(4):544-584 (1990).

Uhlmann et al., "Recent advances in the development of immunostimulatory oligonucleotides", *Current Opinion in Drug Discovery and Development* 6(2):204-217, (Jan. 2003).

Varki et al., "Epidermolysis Bullosa. II. Type VII Collagen Mutations and Phenotype-Genotype Correlations in the Dystrophic Subtypes", *Journal of Medical Genetics* 44:181-192 (2007).

Wengel et al., "LNA (Locked Nucleic Acids): Synthesis and High-Affinity Nucleic Acid Recognition", *Chemical Communications*, p. 455 (1998).

Wengel et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* 54:3607 (1998).

Wengel et al., "Synthesis of 3 c-C- and 4'-C-Branched Oligodeoxynucleotides and the Development of Locked Nucleic Acid (LNA)", *Accounts of Chemical Research* 32:301 (1999).

Williams, "Cationic Lipids Reduce Time and Dose of C-MYC Antisense Oligodeoxynucleotides Required to Specifically Inhibit Burkitt's Lymphoma Cell Growth", *Leukemia* 10(12):1980-1989 (1996).

Written Opinion in International Application No. PCT/US2016/035326, dated Oct. 31, 2016.

Written Opinion in International Application No. PCT/US2018/056572, dated May 6, 2019.

Wu et al., "Receptor-Mediated In Vitro Gene Transformation by a Soluble DNA Carrier System", *Journal of Biological Chemistry* 262:4429-4432 (1987).

Yamada et al., "Synthesis of 2'-O-[2-(N-Methylcarbamoyl)Ethyl]ribonucleosides Using Oxa-Michael Reaction and Chemical and Biological Properties of Oligonucleotide Derivatives Incorporating These Modified Ribonucleosides", *Journal of Organic Chemistry* 76(6):3042-3053 (2011).

Yoo et al., "2'-O-Methyl-Modified Phosphorothioate Antisense Oligonucleotides have Reduced Non-Specific Effects In Vitro", *Nucleic Acids Research* 32:2008-2016 (2004).

\* cited by examiner

SEQUENCE LISTING

<160> NUMBER OF SEQ ID NOS: 36

<210> SEQ ID NO 1
<211> LENGTH: 63
<212> TYPE: DNA
<213> ORGANISM: Homo Sapiens

<400> SEQUENCE: 1
ggtctgcagg gtccaagagg cccccctggc ccagtggtga gtacccaaga accttcacct    60
gtc                                                                 63

<210> SEQ ID NO 2
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(22)
<223> OTHER INFORMATION: n = thymine or uracil

<400> SEQUENCE: 2
nngggnacnc accacngggc ca                                            22

<210> SEQ ID NO 3
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(22)
<223> OTHER INFORMATION: n = thymine or uracil

<400> SEQUENCE: 3
gnncnngggn acncaccacn gg                                            22

<210> SEQ ID NO 4
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(22)
<223> OTHER INFORMATION: n = thymine or uracil

<400> SEQUENCE: 4
aaggnncnng ggnacncacc ac                                            22

<210> SEQ ID NO 5
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(22)
<223> OTHER INFORMATION: n = thymine or uracil

<400> SEQUENCE: 5
acaggngaag gnncnngggn ac                                            22

<210> SEQ ID NO 6
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (3)..(3)
<223> OTHER INFORMATION: n = thymine or uracil -continued

```
<220> FEATURE:
<221> NAME/KEY: misc_feature
<222> LOCATION: (6)..(6)
<223> OTHER INFORMATION: n = thymine or uracil
<220> FEATURE:
<221> NAME/KEY: misc_feature
<222> LOCATION: (13)..(13)
<223> OTHER INFORMATION: n = thymine or uracil
<220> FEATURE:
<221> NAME/KEY: misc_feature
<222> LOCATION: (21)..(21)
<223> OTHER INFORMATION: n = inosine

<400> SEQUENCE: 6
ggnacncacc acngggccag ng                                            22

<210> SEQ ID NO 7
<211> LENGTH: 22
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (6)..(6)
<223> OTHER INFORMATION: n = thymine or uracil
<220> FEATURE:
<221> NAME/KEY: misc_feature
<222> LOCATION: (8)..(8)
<223> OTHER INFORMATION: n = inosine
<220> FEATURE:
<221> NAME/KEY: misc_feature
<222> LOCATION: (14)..(14)
<223> OTHER INFORMATION: n = inosine
<220> FEATURE:
<221> NAME/KEY: misc_feature
<222> LOCATION: (16)..(16)
<223> OTHER INFORMATION: n = inosine
<220> FEATURE:
<221> NAME/KEY: misc_feature
<222> LOCATION: (18)..(18)
<223> OTHER INFORMATION: n = inosine
<220> FEATURE:
<221> NAME/KEY: misc_feature
<222> LOCATION: (21)..(21)
<223> OTHER INFORMATION: n = thymine or uracil

<400> SEQUENCE: 7
accacngngc cagngngncc nc                                            22

<210> SEQ ID NO 8
<211> LENGTH: 24
<212> TYPE: DNA
<213> ORGANISM: Artificial Sequence
<220> FEATURE:
<223> OTHER INFORMATION: Antisense Oligomer
<220> FEATURE:
<221> NAME/KEY: misc_feature
<222> LOCATION: (1)..(24)
<223> OTHER INFORMATION: n = thymine or uracil

<400> SEQUENCE: 8
ggcncnnggg acccngcaga cccn                                          24

<210> SEQ ID NO 9
<211> LENGTH: 9
<212> TYPE: PRT
<213> ORGANISM: Artificial Sequence
<220> FEATURE:
<223> OTHER INFORMATION: rTAT

<400> SEQUENCE: 9
```

Arg Arg Arg Gln Arg Arg Lys Lys Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Tat

<400> SEQUENCE: 10

Arg Lys Lys Arg Arg Gln Arg Arg Arg
1               5

<210> SEQ ID NO 11
<211> LENGTH: 11
<212> TYPE: PRT
<213> ORGANISM: Artificial Sequence
<220> FEATURE:
<223> OTHER INFORMATION: R9F2

<400> SEQUENCE: 11

Arg Arg Arg Arg Arg Arg Arg Arg Arg Phe Phe
1               5                   10

<210> SEQ ID NO 12
<211> LENGTH: 11
<212> TYPE: PRT
<213> ORGANISM: Artificial Sequence
<220> FEATURE:
<223> OTHER INFORMATION: R5F2R4

<400> SEQUENCE: 12

Arg Arg Arg Arg Arg Phe Phe Arg Arg Arg Arg
1               5                   10

<210> SEQ ID NO 13
<211> LENGTH: 4
<212> TYPE: PRT
<213> ORGANISM: Artificial Sequence
<220> FEATURE:
<223> OTHER INFORMATION: R4

<400> SEQUENCE: 13

Arg Arg Arg Arg
1

<210> SEQ ID NO 14
<211> LENGTH: 5
<212> TYPE: PRT
<213> ORGANISM: Artificial Sequence
<220> FEATURE:
<223> OTHER INFORMATION: R5

<400> SEQUENCE: 14

Arg Arg Arg Arg Arg
1               5

<210> SEQ ID NO 15
<211> LENGTH: 6
<212> TYPE: PRT
<213> ORGANISM: Artificial Sequence
<220> FEATURE:
<223> OTHER INFORMATION: R6

<400> SEQUENCE: 15

Arg Arg Arg Arg Arg Arg

```
1               5

<210> SEQ ID NO 16
<211> LENGTH: 7
<212> TYPE: PRT
<213> ORGANISM: Artificial Sequence
<220> FEATURE:
<223> OTHER INFORMATION: R7

<400> SEQUENCE: 16

Arg Arg Arg Arg Arg Arg Arg
1               5

<210> SEQ ID NO 17
<211> LENGTH: 8
<212> TYPE: PRT
<213> ORGANISM: Artificial Sequence
<220> FEATURE:
<223> OTHER INFORMATION: R8

<400> SEQUENCE: 17

Arg Arg Arg Arg Arg Arg Arg Arg
1               5

<210> SEQ ID NO 18
<211> LENGTH: 9
<212> TYPE: PRT
<213> ORGANISM: Artificial Sequence
<220> FEATURE:
<223> OTHER INFORMATION: R9

<400> SEQUENCE: 18

Arg Arg Arg Arg Arg Arg Arg Arg Arg
1               5

<210> SEQ ID NO 19
<211> LENGTH: 16
<212> TYPE: PRT
<213> ORGANISM: Artificial Sequence
<220> FEATURE:
<223> OTHER INFORMATION: (RAhx)8
<220> FEATURE:
<221> NAME/KEY: misc_feature
<222> LOCATION: (1)..(16)
<223> OTHER INFORMATION: Xaa is 6-aminohexanoic acid

<400> SEQUENCE: 19

Arg Xaa Arg Xaa Arg Xaa Arg Xaa Arg Xaa Arg Xaa Arg Xaa Arg Xaa
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: (RAhxR)4 - (P007)
<220> FEATURE:
<221> NAME/KEY: misc_feature
<222> LOCATION: (1)..(12)
<223> OTHER INFORMATION: Xaa is 6-aminohexanoic acid

<400> SEQUENCE: 20

Arg Xaa Arg Arg Xaa Arg Arg Xaa Arg Arg Xaa Arg
1               5                   10

<210> SEQ ID NO 21
<211> LENGTH: 15
<212> TYPE: PRT
```

```
<213> ORGANISM: Artificial Sequence
<220> FEATURE:
<223> OTHER INFORMATION: (RAhxR)5 - (CP04057)
<220> FEATURE:
<221> NAME/KEY: misc_feature
<222> LOCATION: (1)..(15)
<223> OTHER INFORMATION: Xaa is 6-aminohexanoic acid

<400> SEQUENCE: 21

Arg Xaa Arg Arg Xaa Arg Arg Xaa Arg Arg Xaa Arg Arg Xaa Arg
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: (RAhxRRBR)2 - (CP06062)
<220> FEATURE:
<221> NAME/KEY: misc_feature
<222> LOCATION: (2)..(2)
<223> OTHER INFORMATION: Xaa is 6-aminohexanoic acid
<220> FEATURE:
<221> NAME/KEY: misc_feature
<222> LOCATION: (5)..(5)
<223> OTHER INFORMATION: Xaa is beta-alanine
<220> FEATURE:
<221> NAME/KEY: misc_feature
<222> LOCATION: (11)..(11)
<223> OTHER INFORMATION: Xaa is beta-alanine
<220> FEATURE:
<221> NAME/KEY: misc_feature
<222> LOCATION: (8)..(8)
<223> OTHER INFORMATION: Xaa is 6-aminohexanoic acid

<400> SEQUENCE: 22

Arg Xaa Arg Arg Xaa Arg Arg Xaa Arg Arg Xaa Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: (RAR)4F2

<400> SEQUENCE: 23

Arg Ala Arg Arg Ala Arg Arg Ala Arg Arg Ala Arg Phe Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: (RGR)4F2

<400> SEQUENCE: 24

Arg Gly Arg Arg Gly Arg Arg Gly Arg Arg Gly Arg Phe Phe
1               5                   10

<210> SEQ ID NO 25
<211> LENGTH: 19
<212> TYPE: DNA
<213> ORGANISM: Artificial Sequence
<220> FEATURE:
<223> OTHER INFORMATION: DEB 79 FWD Set 2

<400> SEQUENCE: 25
taccaggaga gcgtggtat                                                19
```

<210> SEQ ID NO 26
<211> LENGTH: 18
<212> TYPE: DNA
<213> ORGANISM: Artificial Sequence
<220> FEATURE:
<223> OTHER INFORMATION: DEB 83 REV Set 2

<400> SEQUENCE: 26
gtcctggagg tcctgtct                                                   18

<210> SEQ ID NO 27
<211> LENGTH: 22
<212> TYPE: DNA
<213> ORGANISM: Artificial Sequence
<220> FEATURE:
<223> OTHER INFORMATION: Col7a1-1D(19)

<400> SEQUENCE: 27
aaggttcttg ggtactcacc ac                                              22

<210> SEQ ID NO 28
<211> LENGTH: 22
<212> TYPE: DNA
<213> ORGANISM: Artificial Sequence
<220> FEATURE:
<223> OTHER INFORMATION: Col7a1-2D(16)

<400> SEQUENCE: 28
gttcttgggt actcaccact gg                                              22

<210> SEQ ID NO 29
<211> LENGTH: 22
<212> TYPE: DNA
<213> ORGANISM: Artificial Sequence
<220> FEATURE:
<223> OTHER INFORMATION: Col7a1-3D(09)
<220> FEATURE:
<221> NAME/KEY: misc_feature
<222> LOCATION: (21)..(21)
<223> OTHER INFORMATION: n = inosine

<400> SEQUENCE: 29
ggtactcacc actgggccag ng                                              22

<210> SEQ ID NO 30
<211> LENGTH: 22
<212> TYPE: DNA
<213> ORGANISM: Artificial Sequence
<220> FEATURE:
<223> OTHER INFORMATION: Col7a1-4D(12)

<400> SEQUENCE: 30
ttgggtactc accactgggc ca                                              22

<210> SEQ ID NO 31
<211> LENGTH: 24
<212> TYPE: DNA
<213> ORGANISM: Artificial Sequence
<220> FEATURE:
<223> OTHER INFORMATION: Col7a1-7A(-02-22)

<400> SEQUENCE: 31
ggcctcttgg accctgcaga ccct                                            24

<210> SEQ ID NO 32

```
<211> LENGTH: 22
<212> TYPE: DNA
<213> ORGANISM: Artificial Sequence
<220> FEATURE:
<223> OTHER INFORMATION: Col7a1-6D(-05-26)

<400> SEQUENCE: 32
acaggtgaag gttcttgggt ac                                              22

<210> SEQ ID NO 33
<211> LENGTH: 22
<212> TYPE: DNA
<213> ORGANISM: Artificial Sequence
<220> FEATURE:
<223> OTHER INFORMATION: Col7a1-5D(02)
<220> FEATURE:
<221> NAME/KEY: misc_feature
<222> LOCATION: (1)..(22)
<223> OTHER INFORMATION: n = inosine

<400> SEQUENCE: 33
accactgngc cagngngncc tc                                              22

<210> SEQ ID NO 34
<211> LENGTH: 63
<212> TYPE: DNA
<213> ORGANISM: Artificial Sequence
<220> FEATURE:
<223> OTHER INFORMATION: Target Sequence
<220> FEATURE:
<221> NAME/KEY: misc_feature
<222> LOCATION: (1)..(63)
<223> OTHER INFORMATION: n = thymine or uracil

<400> SEQUENCE: 34
ggncngcagg gnccaagagg cccccongc ccagnggnga gnacccaaga accnncaccn        60 gnc                                                                   63

<210> SEQ ID NO 35
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(19)
<223> OTHER INFORMATION: n = thymine or uracil

<400> SEQUENCE: 35
naccaggaga gcgnggnan                                                  19

<210> SEQ ID NO 36
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(18)
<223> OTHER INFORMATION: n = thymine or uracil

<400> SEQUENCE: 36
gnccnggagg nccngncn                                                   18
```

ANTISENSE-INDUCED EXON EXCLUSION IN TYPE VII COLLAGEN

CROSS-REFERENCE TO RELATED APPLICATIONS

This application is a continuation of U.S. application Ser. No. 15/578,612, filed Nov. 30, 2017, which application is a U.S. National Stage of International Application No. PCT/US16/35326, filed Jun. 1, 2016, which claims priority from U.S. Provisional Patent Application Ser. No. 62/169,454 filed Jun. 1, 2015, which are incorporated herein by reference in their entireties.

STATEMENT REGARDING SEQUENCE LISTING

The Sequence Listing associated with this application is provided in text format, and is hereby incorporated by reference into the specification. The name of the text file containing the Sequence Listing is SPT-8124USCON.txt.

BACKGROUND

Field of the Disclosure

Antisense oligomers and related compositions and methods are disclosed, including methods for increasing expression levels of functional human type VII collagen, methods for treating dystrophic epidermolysis bullosa and related disorders related to the expression of human type VII collagen, and methods for decreasing expression levels of exon 80 in human type VII collagen pre-mRNA transcript, thereby increasing the levels of functional human type VII collagen protein encoded by the human type VII collagen gene (COL7A1).

Description of the Related Art

Antisense technology, recently has been adapted to alter the splicing process of a precursor messenger RNA (pre-mRNA). Pre-mRNA is an immature single strand of messenger RNA synthesized from a DNA transcript through a process known as transcription. The pre-mRNA transcript comprises two different segment types, introns and exons. Introns are removed in a process called splicing, which is generally performed by a spliceosome complex. The remaining exons are joined together and become part of the final, mature mRNA molecule.

The precise process of intron/exon splicing involves various structural elements within the intron region. These include an intron splice donor site, located at the 5' end of the intron, a branch site, located near the 3' end of the intron, and a splice acceptor site, located at the 3' end of the intron. The splice donor site generally includes a conserved GU sequence at the 5' end of the exon/intron junction. The splice acceptor site generally includes an AG sequence at the 3' end of the intron/exon junction.

Variations in the splicing process can create variations in the resultant mRNA by varying the exon composition within the mRNA, a process often referred to as alternative splicing. Alternative splicing can occur in many ways. Exons may be extended or skipped. Portions of introns may be retained. Alternative splicing increases the coding potential of the human genome by producing multiple proteins from a single gene. Inappropriate alternative splicing is also associated with a growing number of human diseases.

Epidermolysis bullosa (EB) is a group of inherited mechanobullous disorders characterized by fragility of the skin within the cutaneous basement membrane zone, with considerable clinical and genetic heterogeneity, inherited either in an autosomal dominant or autosomal recessive fashion. EB has been divided into three broad categories based on the level of tissue separation, determined by diagnostic electron microscopy and/or immunoepitope mapping (Fine et al., 2000): the simplex form of EB (EBS) demonstrates tissue separation within the basal keratinocytes at the bottom layer of epidermis; the junctional form of EB (JEB) displays cleavage within the lamina lucida in the dermoepidermal basement membrane; and the dystrophic form of EB (DEB) displays tissue separation below the lamina densa within the upper papillary dermis (Varki et al., 2007).

DEB is caused by mutations in COL7A1 (Online Mendelian Inheritance in Man® (OMIM) *120120), on chromosomal region 3p21, encoding type VII collagen. It is either dominantly or recessively inherited. The recessive form, RDEB (OMIM #226600) is one of the most severe genodermatoses in children and young adults. The dominant form, DDEB (OMIM #131750) is usually less severe. DEB patients suffer since birth from loss of adhesion between the epidermis and the dermis resulting in severe blistering of the skin and mucosae after mild trauma. The disease leads to severe local and systemic complications, and the prognosis is poor because of the increased risk of aggressive skin cancer. Indeed, over 50% of affected individuals will die before the age of 40-years directly due to metastatic squamous cell carcinoma (Fine et al, 2000). There are 4 subtypes of RDEB: the severe generalized type (Hallopeau-Siemens) which is the most severe; the generalised non-severe (mitis) form; the inversa form (which involves mainly the flexures); and, the centripetalis (localised) form. All these clinical variants are caused by loss of function mutations in COL7A1, which result in structural defects in anchoring fibrils (Hilal et al., 1993; Hovnanian et al., 1992).

Type VII collagen is the major component of anchoring fibrils which are key attachment structures for dermo-epidermal adhesion.

Type VII collagen is synthesized as a 290-kDa protein precursor. The protein has a homotrimeric quaternary structure, and each of the three identical α1-chains consists of three major domains: the 130-kDa globular, non collagenous domain 1 (NC I) at the amino terminus, the helical, collagenous domain of 140 kDa, and the small non collagenous domain 2 (NC2) at the carboxy terminus. In the extracellular matrix, type VII collagen further assembles into antiparallel dimers, with the helical portions disulfide-bonded at a short carboxy terminal overlap that places the amino terminal globular domains at opposite ends. The NCI globular domain is encoded by exons 2 to 27. The central collagenous domain is encoded by exons 28 to 112 and folds into an interrupted collagen triple helix. The larger interruption in the periodic Gly-X-X collagenous sequence is the so-called hinge segment, encoded by exons 71 and 72. With a predicted a-helical structure, it is thought to confer flexibility to the molecule. The NC2 domain is encoded by exons 113 to 118. The NC2 domain is required for the trimerisation of the al chains and for the antiparallel dimerisation of the homotrimers.

The gene encoding type VII collagen, COL7A1, is segmented into 118 exons and spreads over 32 kb on human chromosome 3p21. The shortest exons are 27 nucleotides long while the longest are 201 nucleotides in length. Among the 118 exons, exons 28 to 112 are in frame, suggesting that skipping of any of these exons while preserving the reading frame of the mRNA is theoretically feasible.

Accordingly, novel antisense oligomers and methods of increasing the expression of functional human type VII collagen protein as described herein are believed to be advantageous.

SUMMARY

Compositions and methods for increasing the expression of functional human type VII collagen protein are provided. Variously described antisense oligomers for decreasing expression levels of exon 80 containing human type VII collagen mRNA are further provided.

Various aspects include an antisense oligomer of 12 to 40 subunits, optionally comprising at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an exon/intron splice junction of human type VII collagen pre mRNA. In various embodiments, the contiguous nucleotides include the exon/intron splice junction. In further embodiments, the exon/intron splice junction comprises the splice junction of exon 80/intron 80 (e.g., SEQ ID NO: 1).

Additional aspects include antisense oligomers of 12 to 40 subunits that specifically hybridize to a target region spanning an exon/intron splice junction of human type VII collagen pre-mRNA. The exon/intron splice junction is the splice junction at the intersect of exon 80/intron 80. In embodiments, the splice junction of exon 80/intron 80 comprises the splice junction within SEQ ID NO: 1.

Additional aspects include antisense oligomers having a nucleotide analog subunit comprising a modified sugar moiety. In various embodiments, at least one modified sugar moiety includes a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

Additional aspects include antisense oligomers having a nucleotide analog subunit comprising a modified internucleoside linkage. In various embodiments, the modified internucleoside is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

Additional aspects include antisense oligomers having a nucleotide analog subunit comprising at least one combination of a modified sugar moiety and a modified internucleoside linkage. In various embodiments, one or more subunits are selected from a morpholino subunit optionally substituted with a phosphoramidate internucleoside linkage, a phosphorodiamidate internucleoside linkage, or a phosphorothioate internucleoside linkage, a 2' O-methyl subunit optionally substituted with a phosphoramidate internucleoside linkage, a phosphorodiamidate internucleoside linkage, or a phosphorothioate internucleoside linkage, a 2'O-methoxyethyl subunit optionally substituted with a phosphoramidate internucleoside linkage, a phosphorodiamidate internucleoside linkage, or a phosphorothioate internucleoside linkage, a 2'-fluoro subunit optionally substituted with a phosphoramidate internucleoside linkage, a phosphorodiamidate internucleoside linkage, or a phosphorothioate internucleoside linkages, a 2'O,4'C-ethylene-bridged nucleic acid subunit optionally substituted with a phosphoramidate internucleoside linkage, a phosphorodiamidate internucleoside linkage, or a phosphorothioate internucleoside linkage, a 2'-O-[2-(N-methylcarbamoyl)ethyl] subunit optionally substituted with a phosphoramidate internucleoside linkage, a phosphorodiamidate internucleoside linkage, or a phosphorothioate internucleoside linkage, a tricyclo-DNA subunit optionally substituted with a phosphoramidate internucleoside linkage, a phosphorodiamidate internucleoside linkage, or a phosphorothioate internucleoside linkage, a locked nucleic acid subunit optionally substituted with a phosphoramidate internucleoside linkage, a phosphorodiamidate internucleoside linkage, or a phosphorothioate internucleoside linkage, a morpholino subunit further comprising a phosphorodiamidate internucleoside linkage where a phosphorous atom of the phosphorodiamidate is covalently bonded to the nitrogen atom of the morpholine ring, and is covalently bonded to a (1,4-piperazin)-1-yl moiety or to a substituted (1,4-piperazin)-1-yl moiety, a morpholino subunit further comprising a phosphorodiamidate internucleoside linkage where a phosphorus atom of the phosphorodiamidate is covalently bonded to the nitrogen atom of the morpholine ring, and is covalently bonded to a 4-aminopiperdin-1-yl moiety or a substituted 4-aminopiperdin-1-yl moiety, a ribose sugar subunit substituted with a phosphorothioate internucleoside or a phosphoramidate internucleoside linkage, a deoxyribose sugar subunit substituted with a phosphorothioate internucleoside linkage or a phosphoramidate internucleoside linkage, a peptide nucleic acid subunit optionally substituted, or any combination of the foregoing.

In various aspects and embodiments, antisense oligomers further comprise a peptide covalently bonded to the antisense oligomer. In various embodiments, an arginine-rich cell-penetrating peptide is conjugated to the 3' or the 5' end of the antisense oligomer.

In various embodiments, the antisense oligomer specifically hybridizes to a human type VII collagen pre-mRNA target region. The target region may comprise splice junction sequence(s) set forth in Table 1. In various embodiments, the antisense oligomer specifically hybridizes to a target region spanning an exon/intron splice junction of the human type VII collagen pre-mRNA.

In various embodiments, the antisense oligomer comprises any of a targeting sequence set forth in Table 2, a fragment of at least 12 contiguous nucleotides of a targeting sequence in Table 2, or a variant having at least 90% sequence identity to a targeting sequence in Table 2. In further embodiments, the antisense oligomer consists or consists essentially of a targeting sequence set forth in Table 2.

In various aspects and embodiments, a nucleobase of a nucleotide subunit is independently selected from adenine, guanine, thymine, uracil, cytosine, inosine, hypoxanthine, 2,6-diaminopurine, 5-methyl cytosine, C5-propynyl-modified pyrimidines, and 10-(9-(aminoethoxy)phenoxazinyl).

In various aspects, the antisense oligomer of the disclosure is a compound of formula (I):

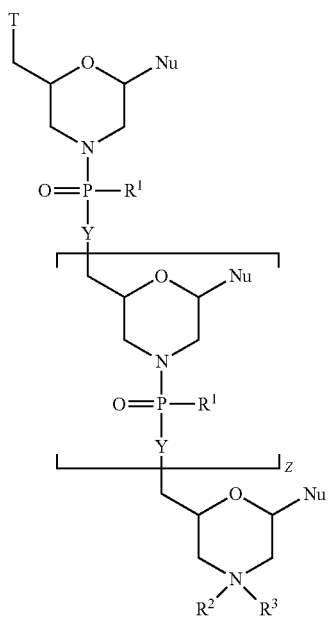

(1)

or a pharmaceutically acceptable salt thereof, where:

each Nu is a nucleobase which taken together forms a targeting sequence;

Z is an integer from 10 to 38;

each Y is independently selected from O and $-NR^4$ where each $R^4$ is independently selected from H, $C_1$-$C_6$ alkyl, aralkyl, $-C(=NH)NH_2$, $-C(O)(CH_2)_nNR^5C(=NH)NH_2$, $-C(O)(CH_2)_2NHC(O)(CH_2)_5NR^5C(=NH)NH_2$, and G, where $R^5$ is selected from H and $C_1$-$C_6$ alkyl and n is an integer from 1 to 5;

T is selected from OH and a moiety of the formula:

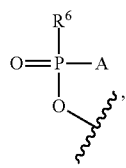

where:

A is selected from $-$OH and $-N(R^7)_2R^8$ where:
each $R^7$ is independently selected from H and $C_1$-$C_6$ alkyl, and
$R^8$ is selected from an electron pair and H, and
$R^6$ is selected from OH, $-N(R^9)CH_2C(O)NH_2$, and a moiety of the formula:

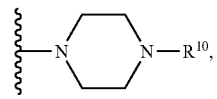

where:
$R^9$ is selected from H and $C_1$-$C_6$ alkyl; and
$R^{10}$ is selected from G, $-C(O)-R^{11}OH$, acyl, trityl, 4-methoxytrityl, $-C(=NH)NH_2$, $-C(O)(CH_2)_mNR^{12}C(=NH)NH_2$, and $-C(O)(CH_2)_2NHC(O)(CH_2)_5NR^{12}C(=NH)NH_2$, where:
m is an integer from 1 to 5,
$R^{11}$ is of the formula $-(O\text{-alkyl})_y\text{-}$ where y is an integer from 3 to 10 and
each of the y alkyl groups is independently selected from $C_2$-$C_6$ alkyl; and
$R^{12}$ is selected from H and $C_1$-$C_6$ alkyl;

each instance of $R^1$ is independently selected from:
$-N(R^{13})_2R^{14}$ where each $R^{13}$ is independently selected from H and $C_1$-$C_6$ alkyl, and $R^{14}$ is selected from an electron pair and H;

a moiety of formula (II):

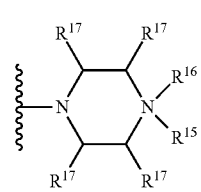

(II)

where:
$R^{15}$ is selected from H, G, $C_1$-$C_6$ alkyl, $-C(=NH)NH_2$, $-C(O)(CH_2)_qNR^{18}C(=NH)NH_2$, and $-C(O)(CH_2)_2NHC(O)(CH_2)_5NR^{18}C(=NH)NH_2$, where:
$R^{18}$ is selected from H and $C_1$-$C_6$ alkyl; and
q is an integer from 1 to 5,
$R^{16}$ is selected from an electron pair and H; and
each $R^{17}$ is independently selected from H and methyl; and a moiety of formula (III):

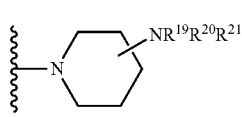

(III)

where:
$R^{19}$ is selected from H, $C_1$-$C_6$ alkyl, $-C(=NH)NH_2$, $-C(O)(CH_2)NR^{22}C(=NH)NH_2$, $-C(O)CH(NH_2)(CH_2)_3NHC(=NH)NH_2$, $-C(O)(CH_2)_2NHC(O)(CH_2)_5NR^{22}C(=NH)NH_2$, $-C(O)CH(NH_2)(CH_2)_4NH_2$ and G, where:
$R^{22}$ is selected from H and $C_1$-$C_6$ alkyl; and
r is an integer from 1 to 5,
$R^{20}$ is selected from H and $C_1$-$C_6$ alkyl; and
$R^{21}$ is selected from an electron pair and H;

$R^2$ is selected from H, G, acyl, trityl, 4-methoxytrityl, $C_1$-$C_6$ alkyl, $-C(=NH)NH_2$, $-C(O)-R^{23}$, $-C(O)(CH_2)_5NR^{24}C(=NH)NH_2$, $-C(O)(CH_2)_2NHC(O)(CH_2)_5NR^{24}C(=NH)NH_2$, $-C(O)CH(NH_2)(CH_2)_3NHC(=NH)NH_2$, and a moiety of the formula:

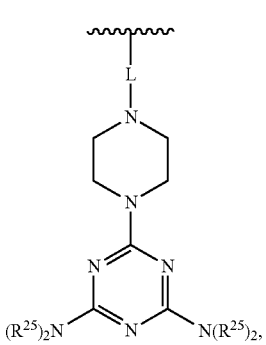

where,
R²³ is of the formula —(O-alkyl)ᵥ-OH where v is an integer from 3 to 10 and each of the v alkyl groups is independently selected from $C_2$-$C_6$ alkyl; and
R²⁴ is selected from H and $C_1$-$C_6$ alkyl;
s is an integer from 1 to 5;
L is selected from —C(O)(CH₂)₆C(O)— and —C(O)(CH₂)₂S₂(CH₂)₂C(O)—; and
each R²⁵ is of the formula —(CH₂)₂OC(O)N(R²⁶)₂ where each R²⁶ is of the formula —(CH₂)₆NHC(=NH)NH₂; and
R³ is selected from an electron pair, H, and $C_1$-$C_6$ alkyl,
where G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, and —C(O)CH₂NH—CPP, or G is of the formula:

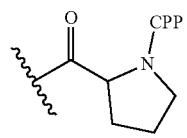

where the CPP is attached to the linker moiety by an amide bond at the CPP carboxy terminus, with the proviso that up to one instance of G is present, and
where the targeting sequence is complementary to 12 or more contiguous nucleotides in a target region spanning an exon/intron junction of human type VII collagen pre-mRNA, wherein said exon/intron junction comprises the splice junction of exon 80/intron 80. In some embodiments, the contiguous nucleotides include the exon/intron splice junction.

In various embodiments, the exon 80/intron 80 junction comprises SEQ ID NO: 1.

In various embodiments, Nu is independently adenine, guanine, thymine, uracil, cytosine, inosine, hypoxanthine, 2,6-diaminopurine, 5-methyl cytosine, C5-propynyl-modified pyrimidines, or 10-(9-(aminoethoxy)phenoxazinyl).

In various embodiments, the targeting sequence comprises a sequence selected from SEQ ID NOS: 2, 3, 4 or 6, is selected from SEQ ID NOS: 2, 3, 4 or 6, is a fragment of at least 12 contiguous nucleotides of a targeting sequence selected from SEQ ID NOS: 2, 3, 4 or 6, or is a variant having at least 90% sequence identity to a targeting sequence selected from SEQ ID NOS: 2, 3, 4 or 6, where X is selected from uracil (U) or thymine (T).

In various embodiments, R¹ of formula (I) is —N(CH₃)₂.

In some embodiments, 50-90% of the R¹ groups are —N(CH₃)₂. In some embodiments, at least one R¹ is selected from:

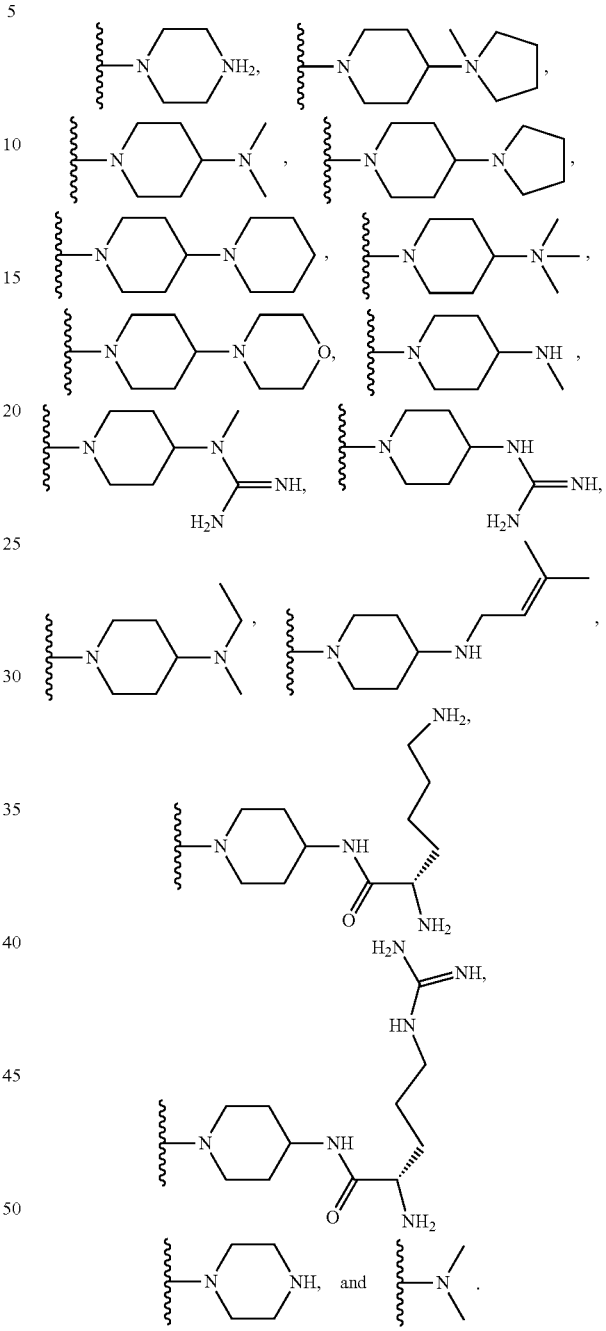

In various embodiments, T is of the formula:

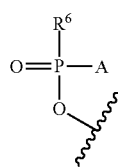

where A is —N(CH$_3$)$_2$, and R$^6$ is of the formula:

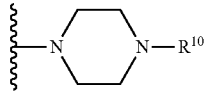

where R$^{10}$ is —C(O)R$^{11}$OH.

In various embodiments, the antisense oligomer is a compound of formula (IV):

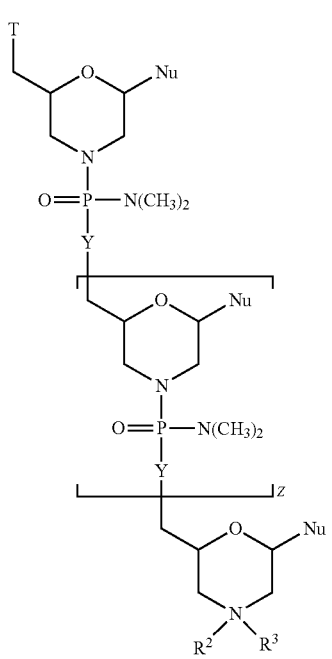

or a pharmaceutically acceptable salt thereof, where:
each Nu is a nucleobase which taken together form a targeting sequence;
Z is an integer from 10 to 38;
each Y is independently selected from O and —NR$^4$, wherein each R$^4$ is independently selected from H, C$_1$-C$_6$ alkyl, aralkyl, —C(=NH)NH$_2$, —C(O)(CH$_2$)$_n$NR$^5$C(=NH)NH$_2$, —C(O)(CH$_2$)$_2$NHC(O)(CH$_2$)$_5$NR$^5$C(=NH)NH$_2$, and G, wherein R$^5$ is selected from H and C$_1$-C$_6$ alkyl and n is an integer from 1 to 5;
T is selected from OH and a moiety of the formula:

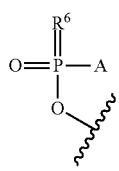

where:
A is selected from —OH and —N(R$^7$)$_2$R$^8$, where:
each R$^7$ is independently selected from H and C$_1$-C$_6$ alkyl, and
R$^8$ is selected from an electron pair and H, and
R$^6$ is selected from OH, —N(R$^9$)CH$_2$C(O)NH$_2$, and a moiety of the formula:

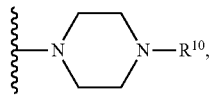

where:
R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$, where:
m is an integer from 1 to 5,
R$^{11}$ is of the formula —(O-alkyl)$_y$-, wherein y is an integer from 3 to 10 and
each of the y alkyl groups is independently selected from C$_2$-C$_6$ alkyl; and
R$^{12}$ is selected from H and C$_1$-C$_6$ alkyl;
R$^2$ is selected from H, G, acyl, trityl, 4-methoxytrityl, C$_1$-C$_6$ alkyl, —C(=NH)NH$_2$, and —C(O)—R$^{23}$; and
R$^3$ is selected from an electron pair, H, and C$_1$-C$_6$ alkyl.

In various embodiments, the targeting sequence of compound (IV) comprises a sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T).

In some embodiments, the targeting sequence is selected from SEQ ID NOS: 2, 3, 4 or 6.

In various embodiments, the antisense oligomer further comprises a peptide moiety which enhances cellular uptake.

In various aspects, antisense oligomers comprising a targeting sequence complementary to 12 or more contiguous nucleotides in a target region spanning an exon/intron splice junction of human type VII collagen pre-mRNA are provided. In some embodiments, the contiguous nucleotides include the exon/intron splice junction. In further aspects and embodiments, the splice junction comprises a splice junction between exon 80/intron 80. In various embodiments, the target region comprises SEQ ID NO: 1 as set forth in Table 1. In some embodiments, the targeting sequence comprises one of SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T). In various embodiments, the targeting sequence comprises SEQ ID NOS: 2, 3, 4 or 6.

Also included are pharmaceutical compositions, comprising a physiologically-acceptable carrier and an antisense oligomer described herein.

Various aspects relate to methods of treating dystrophic epidermolysis bullosa (DEB) and related disorders in a subject in need thereof including, administering to the subject in need thereof an effective amount of an antisense oligomer described herein. In embodiments, dystrophic epidermolysis bullosa and related disorders comprise at least one of Dystrophic Epidermolysis Bullosa (DEB), including any of recessive type Dystrophic Epidermolysis Bullosa (RDEB), dominant type Dystrophic Epidermolysis Bullosa (DDEB), Hallopeau-Siemens type Dystrophic Epidermolysis Bullosa (RDEB-HS), non-severe form of recessive Dystrophic Epidermolysis Bullosa, invesa form of recessive Dystrophic Epidermolysis Bullosa, centripetalis form of recessive Dystrophic Epidermolysis Bullosa, non-Hallopeau-Siemens type Dystrophic Epidermolysis Bullosa (Non-HS RDEB). In other embodiments, methods of treating Epidermolysis Bullosa Simplex (EBS), and Junctional Epidermolysis Bullosa (JEB) are provided. In various embodiments, the antisense oligomer comprises a modified antisense oligomer as described herein.

Methods for increasing the expression of functional human type VII collagen include administering an antisense oligomer to a subject in need thereof, where the antisense oligomer binds to a target region of a human type VII collagen pre-mRNA transcript and binding the antisense oligomer to the target region in the human type VII collagen pre-mRNA transcript, where expression of functional human type VII collagen is increased. Expression of pre-mRNA excluding exon 80 into mature mRNA is increased, such that mature mRNA excludes exon 80. Expression of human type VII collagen mRNA excluding exon 80 is increased. Without being bound to theory, it is believed that the resulting transcript maintains an open reading frame such that the mRNA transcript is translated into functional human type VII collagen protein. Accordingly, expression of genomic exon 80 is inhibited while expression of functional human type VII collagen is increased. In various embodiments, the target is a region spanning an exon/intron splice junction of a human type VII collagen pre-mRNA transcript. In further embodiments, the exon/intron splice junction comprises the splice junction of exon 80/intron 80. In further embodiments, the antisense oligomer comprises a modified antisense oligomer as described herein.

Methods of increasing the expression of functional human type VII collagen protein include, administering an antisense oligomer that binds to a target region of a human type VII collagen pre-mRNA transcript and increasing translation of functional human type VII collagen. In various embodiments, a mutation contained in exon 80, for example, may encode a termination (stop) codon which results in the premature termination of translation of the mRNA transcript, or a mutation in exon 80 may encode for alternative amino acids that result in a non-functional protein. At least some protein translated from a pre-mRNA transcript having such a mutation(s) is non-functional. In accordance with various methods, exon 80 is excluded from at least some of the resulting mature mRNA transcript. The resulting translation of the mature mRNA transcript then results in an increase in functional human type VII collagen protein. In further embodiments, expression of functional human type VII collagen protein is increased. In some embodiments, the target region comprises a splice junction. In certain embodiments, the splice junction comprises an exon 80/intron 80 splice junction. In further aspects and embodiments, translation of human type VII collagen mRNA into functional human type VII collagen protein is increased. In various embodiments, the antisense oligomer comprises a modified antisense oligomer as described herein.

In various embodiments, expression of functional human type VII collagen is increased by at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%.

Methods for increasing the accumulation of functional human type VII collagen in anchoring fibrils and/or increasing the accumulation of anchoring fibrils are provided, comprising administering an antisense oligomer described herein to a subject in need thereof, where the antisense oligomer binds to a target region of a human type VII collagen pre-mRNA transcript. In embodiments, translation of functional human type VII collagen is increased. In further embodiments, the accumulation of: 1) functional human type VII collagen protein in anchoring fibrils in the subject is increased, 2) anchoring fibrils in the subject is increased, or 3) functional human type VII collagen protein in anchoring fibrils and anchoring fibrils in the subject is increased. In embodiments, a subject is a subject with dystrophic epidermolysis bullosa (DEB) or related disorders thereof. In various embodiments, the target region is a region spanning an exon/intron splice junction of a human type VII collagen pre-mRNA transcript, and in further embodiments, the splice junction comprises sequences spanning the exon 80/intron 80 splice junction. In further embodiments, the antisense oligomer comprises a modified antisense oligomer as described herein.

Medicaments for the treatment of dystrophic epidermolysis bullosa (DEB) and related disorders thereof are provided comprising an antisense oligomer compound of 12 to 40 subunits, comprising at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an exon/intron junction of human type VII collagen pre-mRNA transcript, where the contiguous nucleotides include the exon/intron junction, and where said exon/intron junction comprises the splice junction of exon 80/intron 80. In further embodiments, the antisense oligomer comprises a modified antisense oligomer as described herein.

Methods of inhibiting the progression of dystrophic epidermolysis bullosa (DEB) and related disorders include administering an antisense oligomer that binds to a target region of a human type VII collagen pre-mRNA transcript, and increasing translation of functional human type VII collagen. In various embodiments, the antisense oligomer comprises a modified antisense oligomer as described herein.

Methods of treating dystrophic epidermolysis bullosa and related disorders in a subject in need thereof, include, in various embodiments, administering to the subject an effective amount of an antisense oligomer of the disclosure, where the antisense oligomer binds to a target region of a human type VII collagen pre-mRNA transcript, and where transcription of the target region into functional human type VII collagen protein is increased. Further aspects include antisense oligomers for use in the preparation of a medicament for the treatment of dystrophic epidermolysis bullosa and related disorders. In various embodiments, the antisense oligomer comprises a modified antisense oligomer.

In certain embodiments, the method comprises increasing the expression levels of functional human type VII collagen in a subject by at least about 10% relative to a control. In some embodiments, the levels of functional human type VII collagen in a subject are increased by at least about 1, 2, 3, 4, 5, 6, 7, 8, 9, or 10%.

These and other aspects of the present disclosure will become apparent upon reference to the following detailed description and attached drawings. All references disclosed herein are hereby incorporated by reference in their entirety as if each was incorporated individually.

DETAILED DESCRIPTION

I. Definitions

Figure 1A:
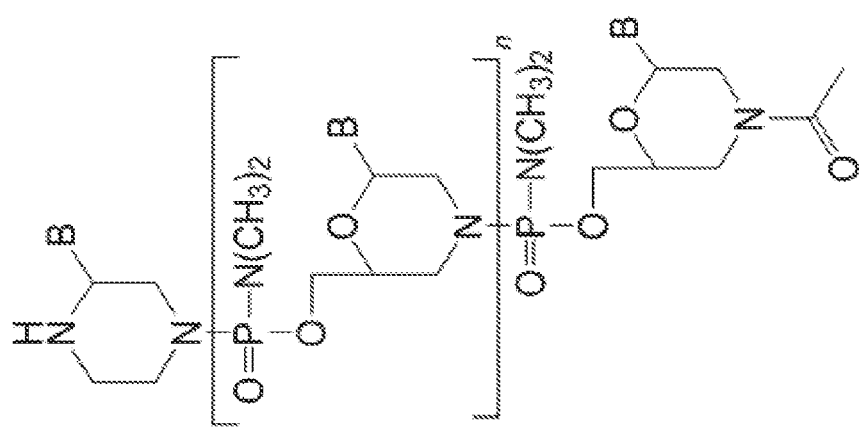
FIG. 1A illustrates a modified oligomer at the 5' end to add a linker.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The terms "sequence" and "coding sequence" mean any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

The term "consisting of" means including, and limited to, whatever follows the phrase "consisting of." Thus, the phrase "consisting of" indicates that the listed elements are required or mandatory, and that no other elements may be present. The term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "administering," or "administer" include delivery of the antisense oligomers of the disclosure to a subject either by local or systemic administration. Administration may be topical (including ophthalmic and to mucous membranes including vaginal and rectal delivery), pulmonary, e.g., by inhalation or insufflation of powders or aerosols, including by nebulizer, intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

The terms "contacting a cell," "introducing" or "delivering" include delivery of the oligomers of the disclosure into a cell by methods routine in the art, e.g., transfection (e.g., liposome, calcium-phosphate, polyethyleneimine), electroporation (e.g., nucleofection), microinjection).

The term "alkyl" refers to a linear (i.e., unbranched or acyclic), branched, cyclic, or polycyclic non aromatic hydrocarbon groups, which are optionally substituted with one or more functional groups. Unless otherwise specified, "alkyl" groups contain one to eight, and preferably one to six carbon atoms. $C_1$-$C_6$ alkyl, is intended to include $C_1$, $C_2$, $C_3$, $C_4$, $C_5$, and $C_6$ alkyl groups. Lower alkyl refers to alkyl groups containing 1 to 6 carbon atoms. Examples of alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "alkoxy" refers to a subset of alkyl in which an alkyl group as defined above with the indicated number of carbons attached through an oxygen bridge. For example, "alkoxy" refers to groups —O-alkyl, where the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

The term "aryl" used alone or as part of a larger moiety as in "aralkyl,", "aralkoxy," or "aryloxy-alkyl," refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring." "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl," as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "acyl" refers to a C(O)R group (in which R signifies H, alkyl or aryl as defined above). Examples of acyl groups include formyl, acetyl, benzoyl, phenylacetyl and similar groups.

The term "homolog" refers to compounds differing regularly by the successive addition of the same chemical group. For example, a homolog of a compound may differ by the addition of one or more —$CH_2$— groups, amino acid residues, nucleotides, or nucleotide analogs.

The terms "cell penetrating peptide" (CPP) or "a peptide moiety which enhances cellular uptake" are used interchangeably and refer to cationic cell penetrating peptides, also called "transport peptides," "carrier peptides," or "peptide transduction domains." For example, a peptide-conjugated phosphoramidate or phosphorodiamidate morpholino (PPMO) may include a cell penetrating peptide or peptide moiety which enhances cellular uptake as described herein. In various embodiments, a peptide may be covalently bonded to the antisense oligomer. In further embodiments, a peptide may be conjugated to the 3' end or the 5' end of the antisense oligomer. In further embodiments, a peptide may be linked to a piperazinyl moiety or to a nitrogen atom of the 3' terminal morpholine ring. In some embodiments, a cell penetrating peptide or peptide moiety which enhances cellular uptake may include an arginine-rich peptide as described herein.

The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. In some embodiments, the CPPs are of the formula —[(C(O)CHR'NH)$_m$]R" where R' is a side chain of a naturally occurring amino acid or a one- or two-carbon homolog thereof, R" is selected from Hydrogen or acyl, and m is an integer up to 50. Additional CPPs are well-known in the art and are disclosed, for example, in U.S. Published Application No. 20100016215, which is hereby incorporated by reference in its entirety. In other embodiments, m is an integer selected from 1 to 50 where, when m is 1, the moiety is a single amino acid or derivative thereof.

The term "amino acid" refers to a compound comprising a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine, Aspartic Acid, Histidine, Methionine, Proline, Phenylalanine, Threonine, Tryptophan, Cysteine, Glutamic Acid, Serine, Tyrosine, Pyrolysine, Selenocystenine and Arginine. Additionally, as used herein, "amino acid" also includes derivatives of amino acids such as esters, and amides, and salts, as well as other derivatives, including derivatives having pharmaco properties upon metabolism to an active form. Accordingly, the term "amino acid" is understood to include naturally occurring and non-naturally occurring amino acids.

The term "an electron pair" refers to a valence pair of electrons that are not bonded or shared with other atoms.

The term "homology" refers to the percentage number of amino acids that are identical or constitute conservative substitutions. Homology may be determined using sequence comparison programs such as GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The term "isolated" refers to a material that is substantially or essentially free from components that normally accompany it in its native state. For example, an "isolated oligonucleotide," or "isolated oligomer" as used herein, may refer to an oligomer that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with an oligonucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more antisense oligomer compounds or compositions to produce or cause a greater physiological response (e.g., downstream effects) in a cell or a subject relative to the response caused by either no antisense oligomer compound or a control compound. Relevant physiological or cellular responses (in vivo or in vitro) will be apparent to persons skilled in the art, and may include decreases in the inclusion of exon 80 in a COL7A1 human type VII collagen-coding mRNA, or the exclusion of exon 80 in a human type VII collagen mRNA transcript, and/or an increase in the expression of functional human type VII collagen protein in a skin cell, or tissue, such as in a subject in need thereof. A "decreased" or "reduced" amount is typically a "statistically significant" amount, and may include a decrease that is 1, 2, 3, 4, 5, 6, 7, 8, 9, 10, 15, 20, 30, 40, 50 or more times less (e.g., 100, 500, 1000 times), including all integers and decimal points in between and above 1 (e.g., 1.1, 1.2, 1.3, 1.4, 1.5, 1.6, 1.7, 1.8, 1.9), the amount produced by a subject in need thereof in the absence of administration of an antisense oligomer compound (e.g. the "native" or "natural" rate of expression of a specific subject or cohort) or a control compound. The terms "reduce" or "inhibit" may relate generally to the ability of one or more antisense oligomer compounds or compositions to "decrease" a relevant physiological or cellular response, such as a symptom of a disease or condition described herein, as measured according to routine techniques in the diagnostic art. An "increased" or "enhanced" amount is typically a "statistically significant" amount, and may include an increase that is 1, 2, 3, 4, 5, 6, 7, 8, 9, 10, 15, 20, 30, 40, 50 or more times greater than (e.g., 100, 500, 1000 times), including all integers and decimal points in between and above 1 (e.g., 1.1, 1.2, 1.3, 1.4, 1.5, 1.6, 1.7, 1.8, 1.9), the amount produced by a subject in need thereof in the absence of administration of an antisense oligomer compound (e.g. the "native" or "natural" rate of expression of a specific subject or cohort) or a control compound. The term "enhance" may relate generally to the ability of one or more antisense oligomer compounds or compositions to "increase" a relevant physiological or cellular response, such as a symptom of a disease or condition described herein, as measured according to routine techniques in the diagnostic art.

Relevant physiological or cellular responses (in vivo or in vitro) will be apparent to persons skilled in the art, and may include reductions in the symptoms or pathology of eipermolysis bullosa and related disorders, such as Dystrophic Epidermolysis Bullosa (DEB), including any of recessive type Dystrophic Epidermolysis Bullosa (RDEB), dominant type Dystrophic Epidermolysis Bullosa (DDEB), Hallopeau-Siemens type Dystrophic Epidermolysis Bullosa (RDEB-HS), non-severe form of recessive Dystrophic Epidermolysis Bullosa, invesa form of recessive Dystrophic Epidermolysis Bullosa, centripetalis form of recessive Dystrophic Epidermolysis Bullosa, non-Hallopeau-Siemens type Dystrophic Epidermolysis Bullosa (Non-HS RDEB). In other embodiments, methods of treating Epidermolysis Bullosa Simplex (EBS), and Junctional Epidermolysis Bullosa (JEB) are provided, for example, where a reduction in symptoms or pathology may accompany or relate to an increase in the expression of functional human type VII collagen protein, increasing the accumulation of functional human type VII collagen in anchoring fibrils and/or increasing the accumulation of anchoring fibrils in one or more tissues. An "increase" in a response may be "statistically significant" as compared to the response produced by a subject in need thereof in the absence of administration of an antisense oligomer compound (e.g. the "native" or "natural" rate of expression of a specific subject or cohort) or a control compound, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase, including all integers in between.

The term "functional" in reference to a human type VII collagen protein includes those type VII collagen proteins possessing, for example, a portion or substantial portion of the functionality of wild-type type VII collagen protein, nearly complete or complete functionality of wild-type or normal type VII collagen protein. A functional protein may be derived from a mRNA transcript having one or more exons removed or excised such that the resulting mRNA transcript maintains the open reading frame. A functional protein may be derived from a RNA transcript where, for example, exon 80 is excluded. A protein translated from a mRNA transcript having fewer exons than the wildtype mRNA may result in a transcribed protein comprising fewer amino acid residues than a protein transcribed from a wildtype mRNA transcript. A functional protein composed of fewer amino acid residues than a wildtype protein may have the same or similar activity/functionality as the wild-type protein. For example, a functional type VII collagen protein may have or possess about 5% to about 100%, about 5% to about 90%, about 5% to about 80%, about 5% to about 70%, about 5% to about 60%, about 5% to about 50%, about 5% to about 30%, about 5% to about 20%, about 5% to about 10%, about 10% to about 100%, about 10% to about 90%, about 10% to about 80%, about 10% to about 70%, about 10% to about 60%, about 10% to about 50%, about 10% to about 40%, about 10% to about 30%, about 10% to about 20%, about 30% to about 100%, about 30% to about 90%, about 30% to about 80%, about 30% to about 70%, about 30% to about 60%, about 30% to about 50%, about 40% to about 100%, about 40% to about 90%, about 40% to about 80%, about 40% to about 70%, about 40% to about 60%, about 40% to about 50%, about 50% to about 100%, about 50% to about 90%, about 50% to about 80%, about 50% to about 70%, about 50% to about 60%, about 60% to about 100%, about 60% to about 90%, about 60% to about 80%, about 60% to about 70%, about 70% to about 100%, about 70% to about 90%, about 70% to about 80%, about 80% to about 100%, about 80% to about 90%, or about 90% to about 100% of the functionality of wild-type or normal type VII collagen protein.

A non-functional, dysfunctional or inactive protein includes a protein derived from a mRNA transcript including an exon 80 mutation and/or having little to no functionality of wild-type type VII collagen protein. For example, a functional type VII collagen protein may possess about 5%, 10%, 15%, 20%, 25%, 30%, 35%, 40%, 45%, 50%, 55%, 60%, 65%, 70%, 75% 80%, 85%, 90%, 95%, or 100% of the functionality of wild-type or normal type VII collagen protein. A non-functional, dysfunctional or inactive protein includes a protein derived from a mRNA transcript containing one or more mutations in exon 80 of human type VII collagen COL7A1 gene. A mutation in exon 80 may, for example, incorporate a premature stop codon such that translation of the resulting mRNA transcript is prematurely terminated, or may encode for alternative amino acids that result in a non-functional protein. The resulting human type VII collagen protein is a non-functional, dysfunctional or inactive protein and is degraded. COL7A1 gene mutations are disclosed in International Published Application No. WO 2013/053819 and Varki et al., J. Med. Genet., 2007, 44:181-192, the contents of which are incorporated herein by reference.

The disclosure thus provides methods of restoring functionality to type VII collagen, e.g. an unstable, defective, dysfunctional, not enough functional or non-functional type VII collagen, and/or increasing expression of functional human type VII collagen. Those skilled in the art will recognize that there are many ways to determine or measure a level of functionality of a protein, and to determine a level of increase or decrease of functionality or whether a functional protein is produced and/or whether expression of a functional protein is increased, e.g. in response to a treatment protocol. Such methods include, but are not limited to, measuring or detecting an activity/functionality of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein.

Particularly, the functionality of type VII collagen and/or whether a type VII collagen protein is functional can be measured and/or determined in vitro and/or in vivo by several methods recognized in the art:

The synthesis of type VII collagen following exon 80 skipping can be assessed by western blotting (Titeux et al., 2010). However, as described in WO 2013/053819 (FIG. 1A), the disclosure of which is incorporated by reference in its entirety, due to the small size of the targeted exon 80, the skipped mRNA synthesizes a protein with an apparent molecular weight similar to that of the wild-type protein.

The correct assembly of the a1 collagen chains into homotrimers can be demonstrated by western blotting under non reducing conditions. The correct proteolytic pattern of type VII collagen homotrimers can be assessed by Pepsin and collagenase digestions followed by western blotting (Titeux et al., 2010).

Colloidal gold migration assay. Cell mobility of treated cells can be assayed on a collagen matrix as RDEB cells display an enhanced motility compared to normal keratinocytes and fibroblasts (Chen et al., 2002).

In vitro adhesion assays. RDEB cells display a defect in adhesion to extracellular matrix components like type I collagen, type IV collagen, fibronectin but not laminin I (Chen et al., 2002).

Detection of type VII collagen at the dermal epidermal junction by indirect immunohistochemistry using xenograft of treated RDEB skin equivalents grafted onto nude mice (Titeux et al., 2010).

Assessment of anchoring fibrils formation in vivo by transmission electron microscopy (TEM) using xenograft of treated RDEB skin equivalents grafted onto nude mice (Titeux et al., 2010).

Demonstration of the restoration of dermal-epidermal adherence in vivo using xenograft of treated RDEB skin equivalents grafted onto nude mice (Titeux et al., 2010).

The entire contents of the above references are incorporated herein by reference.

Figure 4:
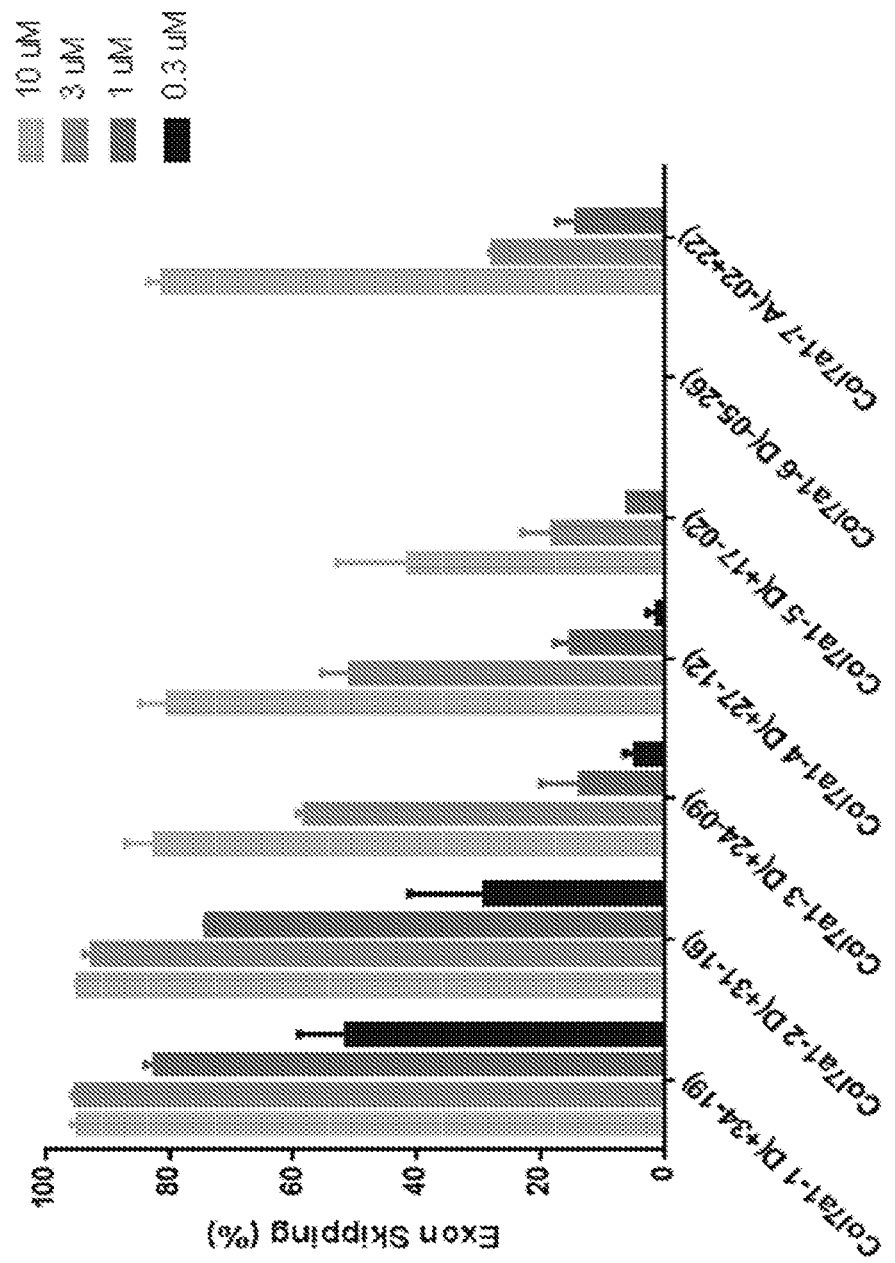
FIG. 4 illustrates a first series of human type VII collagen antisense oligomers activity in human adult epidermal keratinocytes (HEKa).

Thus, in various embodiments, the presence of, expression of, or increased expression of functional type VII collagen may be determined, for example, by western blot analysis of, for example, RDEB cells treated with an antisense oligomer of the instant disclosure to evaluate the presence of both monomers and homotrimers of type VII collagen (see for example, WO2013/053819, Examples 1 and 3, and FIGS. 1A and 4; the entire contents of which are incorporated herein by reference). In various embodiments, treatment of RDEB cells or a subject in need of treatment of DEB with an antisense oligomer of the disclosure may result in expression of a type VII collagen protein in an amount that is, for example, about 5%, 10%, 15%, 20%, 25%, 30%, 35%, 40%, 45%, 50%, 55%, 60%, 65%, 70%, 75%, 80%, 85%, 90%, 95%, or 100%, or any of the percentile ranges disclosed above, of the normal amount of type VII collagen expressed in normal cells or a normal subject.

Figure 1B:
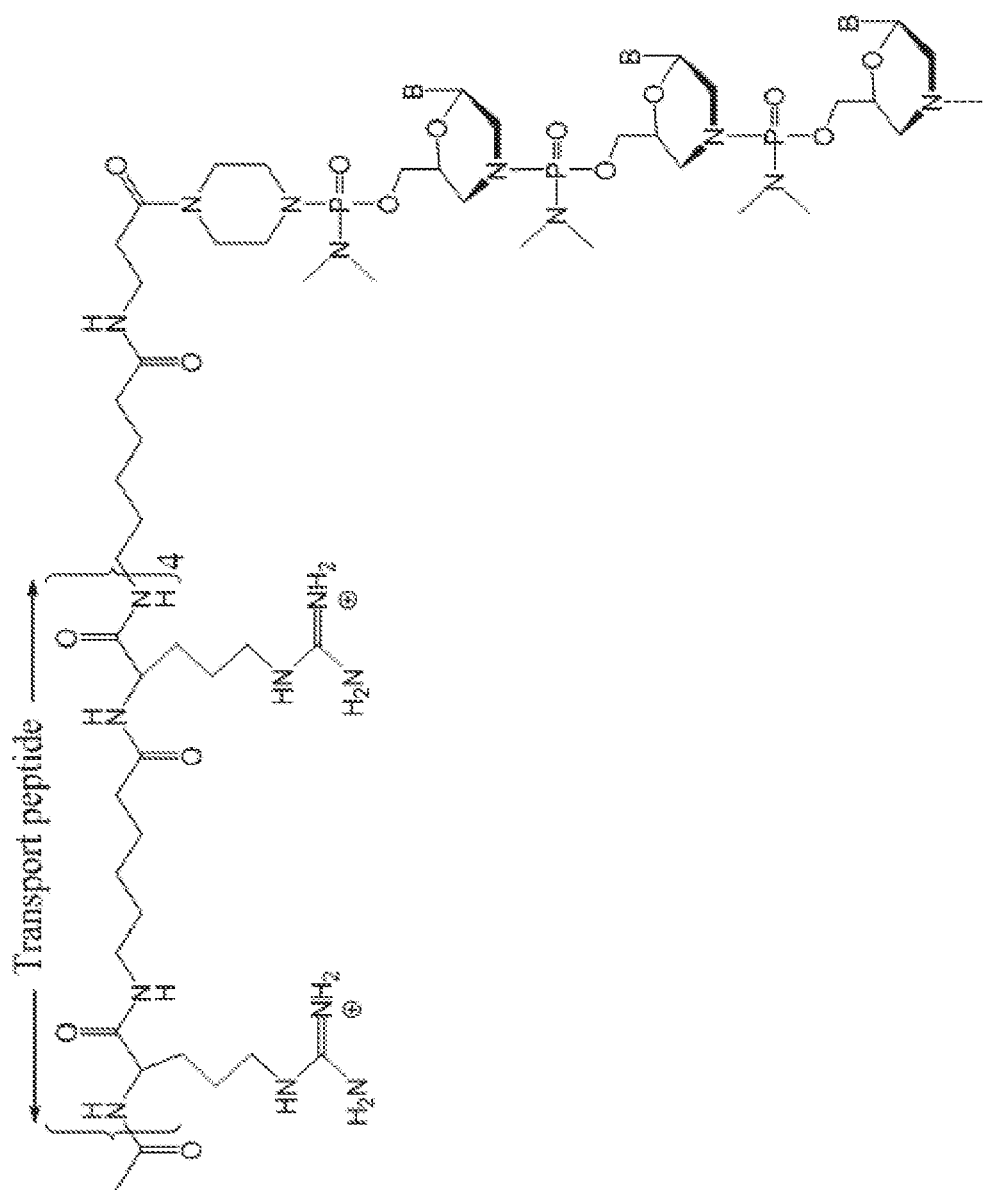
FIGS. 1B and 1C illustrates an antisense oligomer conjugated to a cell penetrating peptide (CPP).

In various aspects of the disclosure, functionality of a type VII collagen expressed by RDEB cells or a subject in need of treatment of DEB may be determined by immunohistochemical analysis and transmission electron microcopy of, for example, RDEB skin equivalents for the presence of normal type VII collagen deposits along the dermal-epidermal junction, anchoring fibrils formation and/or accumulation, and dermal-epidermal adhesion as compared to untreated RDEB skin equivalents (see for example, WO 2013/053819, Example 1 and FIG. 1B; the entire contents of which are incorporated herein by reference).

In the present case, antisense oligomers are used to cause exon 80 skipping resulting in an amelioration of Dystrophic Epidermolysis Bullosa symptoms (i.e. restoration of protein function or stability) in the range of about 30% to about 100% or the percentages disclosed above with regard to functionality, compared to a non-treatment. Such symptoms may be observed on a micro level (i.e. restoration of protein expression and/or localization evaluated by, for example, immunohistochemistry, immunofluorescence, western-blot analyses; amelioration of the skin lesion by histological examination; restoration/amelioration of protein functionality evaluated by the ability to form anchoring fibrils between the external epithelia and the underlying stroma.

The term "nucleotide" refers to a naturally occurring nucleotide comprising a nucleobase, a sugar and at least one phosphate group (e.g., a phosphodiester linking group).

The term "nucleotide analog" refers to a derivative of, or modification to, a naturally occurring nucleotide, for example, a nucleotide comprising at least one modification. Such modifications may include at least one of (i) a modified internucleoside linkage, (ii) a modified sugar moiety, or (iii) a combination of the foregoing. The skilled practitioner will appreciate that where a modification is specified with respect to any one component of a nucleotide subunit (e.g., a modified sugar), the unspecified portion(s) of the nucleotide subunit may remain unmodified (e.g., an unmodified internucleoside linkage, an unmodified nucleobase).

The terms "oligonucleotide," "oligomer," "oligo," "antisense oligonucleotide," "antisense oligomer," and "antisense oligo," and other appropriate combinations and derivations thereof, refer to linear sequences of nucleotides, or nucleotide analogs, where one or more nucleobases may hybridize to a portion of a target RNA against which the oligomer is directed, referred to as a target sequence, by Watson-Crick base pairing, to form an oligomer:RNA heteroduplex within the target sequence. Specifically, the terms "antisense," "oligonucleotide," "oligomer," "oligo" and "compound" may be used in various combinations and interchangeably to refer to such an oligomer. Cyclic subunits comprising portions of the nucleotides may be based on ribose or another pentose sugar, sugar analog or, in certain embodiments may be a modified sugar, for example, a morpholino group (see description of morpholino-based oligomers below).

The term "modified," "non-naturally-occurring," or "analogs," and other appropriate combinations and derivatives thereof, when referring to oligomers, refer to oligomers having one or more nucleotide subunits having at least one modification selected from (i) a modified internucleoside linkage, e.g., an internucleoside linkage other than the standard phosphodiester linkage found in naturally-occurring oligonucleotides, (ii) modified sugar moieties, e.g., moieties other rather than ribose or deoxyribose moieties found in naturally occurring oligonucleotides, or (iii) a combination of the foregoing. In various embodiments, a modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

A modification to the internucleoside linkage may be between at least two sugar and/or modified sugar moieties of an oligomer. Nucleotide analogs support bases capable of hydrogen bonding by Watson-Crick base pairing to naturally occurring oligonucleotide bases, where the analog presents the bases in a manner to permit such hydrogen bonding in a sequence-specific fashion between the oligomer analog molecule and bases in the naturally occurring oligonucleotide (e.g., single-stranded RNA or single-stranded DNA). Exemplary analogs are those having a substantially uncharged, phosphorus containing internucleoside linkages.

A "nuclease-resistant" oligomer refers to one whose internucleoside linkage is substantially resistant to nuclease cleavage, in non-hybridized or hybridized form; by common extracellular and intracellular nucleases in the body (for example, by exonucleases such as 3'-exonucleases, endonucleases, RNase H); that is, the oligomer shows little or no nuclease cleavage under normal nuclease conditions in the body to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA. For example, a nuclease-resistant oligomer may be an antisense oligomer as described herein.

The terms "nucleobase" (Nu), "base pairing moiety" or "base" are used interchangeably to refer to a purine or pyrimidine base found in naturally occurring, or "native." DNA or RNA (e.g., uracil, thymine, adenine, cytosine, and guanine), as well as analogs of these naturally occurring purines and pyrimidines, that may confer improved properties, such as binding affinity to the oligomer. Exemplary analogs include hypoxanthine (the base component of the nucleoside inosine); 2, 6-diaminopurine; 5-methyl cytosine; C₅-propynyl-modified pyrimidines; 10-(9-(aminoethoxy) phenoxazinyl) (G-clamp) and the like.

Further examples of base pairing moieties include, but are not limited to, uracil, thymine, adenine, cytosine, guanine and hypoxanthine (inosine) having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glen-research.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

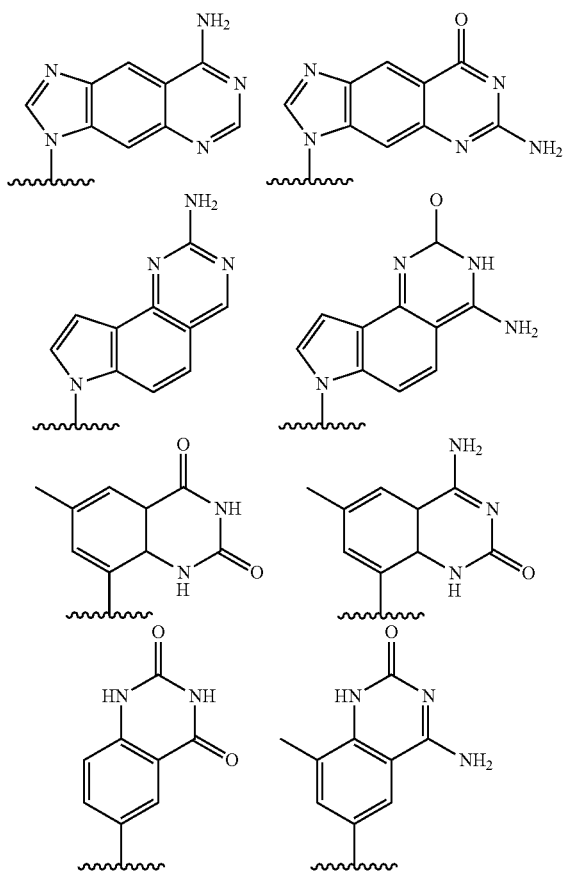

-continued

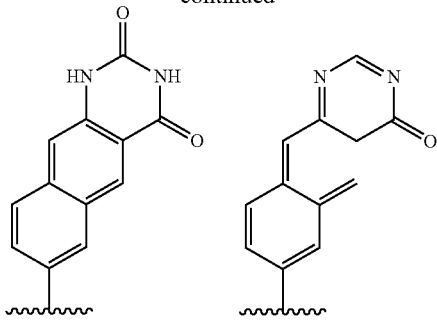

A nucleobase covalently linked to a ribose, sugar analog, modified sugar or morpholino comprises a nucleoside. "Nucleotides" comprise a nucleoside together with at least one linking phosphate group. The phosphate groups comprise covalent linkages to adjacent nucleosides form an oligomer. Thus, the phosphate group of the nucleotide is commonly referred to as forming an "internucleoside linkage." Accordingly, a nucleotide comprises a nucleoside as further described herein and an internucleoside linkage. In some embodiments, an antisense oligomer of the disclosure comprises subunits wherein a "subunit" includes naturally occurring nucleotides, nucleotide analogs as described herein, and combinations thereof. In certain embodiments, an antisense oligomer of the disclosure comprises subunits wherein at least one subunit is a nucleotide analog.

The terms "sequence identity" and "sequence homology" (e.g. a "sequence 50% identical to) refer to the extent that a sequence is identical on a nucleotide-by-nucleotide basis over a window of comparison. A "percentage identity" may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997. In various embodiments, an antisense oligomer of the disclosure may have at least 70%, 75%, 80%, 85%, 90%, 95%, 99% or 100% sequence identity with a targeting sequence in Table 2 (SEQ ID NOS: 2, 3, 4 and 6).

As used herein, an oligomer "specifically hybridizes" to a target oligonucleotide if the oligomer hybridizes to the target under physiological conditions, with a melting point (Tm) substantially greater than 40° C., 45° C., 50° C., and in various embodiments, 60° C.-80° C. or higher. Such hybridization preferably corresponds to stringent hybridization conditions. At a given ionic strength and pH, the Tm is the temperature at which 50% of a target sequence hybridizes to a complementary sequence. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100%.

As used herein, the term "subunit" refers to a naturally occurring nucleotide or a naturally occurring nucleotide comprising at least one modification. A modification may comprise at least one of (i) a modified internucleoside linkage, (ii) a modified sugar moiety, or (iii) a combination of the foregoing. In further embodiments, a modification may include a modified nucleobase.

As used herein, the term "sufficient length" refers to an antisense oligomer that is complementary to at least 12, more typically 12-40, contiguous nucleobases in a region spanning a human type VII collagen pre-mRNA exon/intron splice junction region comprising exon 80/intron 80. In various embodiments, the antisense oligomer comprises at least a number of nucleotides to be capable of specifically hybridizing to a target region of a human type VII collagen pre-mRNA sequence. Preferably an oligomer of sufficient length is from 12 to 30 nucleotides, 12-25 nucleotides, 12-22 nucleotides, 15-25 nucleotides, 15-22 nucleotides, or 15-20 nucleotides in length, including all integers in between these ranges. More preferably, an oligomer of sufficient length is from 12 to 27, 12 to 22 or 15-22 nucleotides in length.

As used herein, the term a "subject" or a "subject in need thereof" includes a mammalian subject such as a human subject. Exemplary mammalian subjects have or are at risk for having epidermolysis bullosa and related disorders. As used herein, the term "epidermolysis bullosa" and "related disorders" refers to a group of inherited mechanobullous disorders or related disorder, a human autosomal dominant or autosomal recessive disease that is often characterized by the expression of dysfunctional human type VII collagen protein in affected individuals. In some embodiments, epidermolysis bullosa (DB) and related disorders include, but are not limited to, Dystrophic Epidermolysis Bullosa (DEB), including any of recessive type Dystrophic Epidermolysis Bullosa (RDEB), dominant type Dystrophic Epidermolysis Bullosa (DDEB), Hallopeau-Siemens type Dystrophic Epidermolysis Bullosa (RDEB-HS), non-severe form of recessive Dystrophic Epidermolysis Bullosa, invesa form of recessive Dystrophic Epidermolysis Bullosa, centripetalis form of recessive Dystrophic Epidermolysis Bullosa, non-Hallopeau-Siemens type Dystrophic Epidermolysis Bullosa (Non-HS RDEB). In other embodiments, methods of treating Epidermolysis Bullosa Simplex (EBS), and Junctional Epidermolysis Bullosa (JEB) are provided.

As used herein, the term "target" refers to a region within a pre-mRNA transcript as relating to the antisense oligomers contemplated herein. In various aspects, the target is a region of a human type VII collagen pre-mRNA spanning an exon/intron splice junction of human type VII collagen pre-mRNA. In various embodiments, the target region is an exon/intron splice junction region comprising exon 80/intron 80 of the pre-mRNA of human type VII collagen. In various embodiments, the target region comprises all or at least a portion of SEQ ID NO: 1 wherein the portion spans at least the splice junction of exon 80/intron 80. In embodiments, the exon/intron splice junction is a donor exon/intron splice junction of human type VII collagen. In further embodiments, the donor exon/intron splice junction comprises the donor exon/intron splice junction of exon 80/intron 80.

In various embodiments, the term "targeting sequence" refers to the sequence in the antisense oligomer or oligomer analog that is complementary to the target sequence in the pre-mRNA transcript. The entire sequence, or only a portion, of the antisense oligomer may be complementary to the target sequence. For example, in an oligomer having 20-30 bases, about 12, 13, 14, 15, 16, 17, 18, 19, 20, 21, 22, 23, 24, 25, 26, 27, 28, 29, or 30 may contain sequences (e.g. "targeting sequences") that are complementary to the target region within the pre-mRNA transcript. Typically, the targeting sequence is formed of contiguous bases in the oligomer, but may alternatively be formed of non-contiguous sequences that when placed together, e.g., from opposite ends of the oligomer, constitute a sequence that spans the target sequence.

A "targeting sequence" may have "near" or "substantial" complementarity to the target sequence and still function for its intended purpose, for example, to decrease expression of human type VII collagen exon 80 coding pre-mRNA, or increase expression of functional human type VII collagen protein, or increase the accumulation of functional human type VII collagen in anchoring fibrils, or increase the accumulation of anchoring fibrils. Preferably, antisense oligomer compounds employed in the present disclosure have at most one mismatch with the target sequence out of 12 nucleotides, and preferably at most one mismatch out of 20. Alternatively, the antisense oligomers employed have at least 90% sequence homology, and preferably at least 95% sequence homology, with the exemplary targeting sequences as designated herein. A targeting sequence may be a sequence spanning an exon/intron splice junction of the human type VII collagen COL7A1 gene. In some embodiments, an exon/intron splice junction comprises the splice junction of exon 80/intron 80.

As used herein, the term "TEG," "triethylene glycol tail," or "G3" refers to triethylene glycol moieties conjugated to the oligomer, e.g., at its 3'- or 5'-end. For example, in some embodiments, "TEG" includes wherein T of the compound of formula (I) is of the formula:

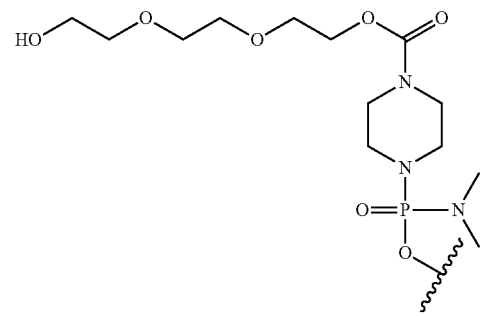

As used herein, the term a "therapeutically effective amount" or "effective amount" of a composition refers to an amount effective in the prevention or treatment of a disorder for the treatment of which the composition is effective. A "disorder" refers to any dystrophic epidermolysis bullosa or related disorders that would benefit from treatment with the composition.

As used herein, the terms "quantifying," "quantification" or other related words refer to determining the quantity, mass, or concentration in a unit volume, of a nucleic acid, oligonucleotide, oligomer, peptide, polypeptide, or protein.

In various embodiments, as used herein, the term "treatment" includes treatment of a subject (e.g. a mammal, such as a human) or a cell to alter the current course of the subject or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

II. Modulation of the Exon 80 Exon/Intron Splice Junction of Human Type VII Collagen Pre-mRNA Various aspects relate to methods for modulating the splicing of intron and exons of human type VII collagen pre-mRNA. Further aspects relate to inhibiting splicing at the splice junction site of exon 80/intron 80. In further aspects, expression of human type VII collagen coding mRNA, excluding exon 80 is increased, such as relative to exon 80 containing wildtype mRNA, in a given sample (e.g., serum, plasma, tissue, cellular etc.). Various methods include administering an antisense oligomer described herein that is complementary to a target region within the human type VII collagen pre-mRNA, where expression of human type VII collagen mRNA, excluding exon 80, is increased relative to the expression of exon 80 containing wildtype (i.e. control) mRNA.

For illustration purposes, and without being bound by theory, antisense oligomers as described herein are believed to facilitate blocking, inhibiting or modulating the processing of a pre-mRNA, such as by inhibiting the action of a spliceosome and production of a mature mRNA transcript, and may also induce degradation of targeted mRNAs. In some instances, a splicesome may be inhibited from binding to an exon/intron splice junction such that an exon/intron splice junction is skipped and one or more exons are removed from a mRNA transcript. A mature mRNA transcript having one or more exons less than a wildtype mRNA transcript may result in a mRNA transcript that maintains the open reading frame such that the mRNA transcript may be translated to functional protein rather than degraded. A protein translated from a mRNA transcript having fewer exons than the wildtype mRNA may result in a transcribed protein comprising fewer amino acid residues than a protein transcribed from a wildtype mRNA transcript. A functional protein composed of fewer amino acid residues than a wildtype protein may have the same or similar activity/functionality as the wildtype protein. The antisense oligomer may be said to be "directed to" or "targeted against" a target sequence or target region with which it hybridizes. In certain embodiments, the target sequence includes a region including a 3' or 5' splice junction site of a pre-mRNA, a branch point, Exonic Splicing Enhancers (ESE) or Intronic Splicing Enhancers (ISE), or other sequence involved in the regulation of splicing. Within an intron, a donor site (5' end of the intron) and an acceptor site (3' end of the intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. The target sequence may include sequences within an exon/intron splice junction site, or spanning an exon/intron splice junction. The target sequence may include an exon/intron donor splice site.

An antisense oligomer having a sufficient sequence complementarity to a target pre-mRNA sequence to modulate splicing of the target RNA includes where the antisense oligomer has a sequence sufficient to trigger the masking or hindrance of a binding site for a spliceosome complex that would otherwise affect such splicing and/or otherwise includes alterations in the three-dimensional structure of the targeted pre-mRNA.

In various embodiments, the antisense oligomer has sufficient length and complementarity to a sequence spanning an exon 80/intron 80 splice junction of the human type VII collagen pre-mRNA. In various embodiments, targeting sequences within an antisense oligomer hybridize to a region of the target sequences, for example SEQ ID NO: 1, shown in Table 1 below. In some embodiments, antisense oligomers may be shorter, e.g., about 12 bases, or longer, e.g., about 40 bases, and include a small number of mismatches, as long as the sequence is sufficiently complementary to effect splice modulation upon hybridization to the target sequence, and optionally forms with the RNA a heteroduplex having a Tm of 45° C. or greater.

TABLE 1

Target sequence for Human Type VII Collagen-targeted oligomers (from GenBank/EMBL L23982)

| Name | Sequence (5'-3') | SEQ ID NO |
|---|---|---|
| Exon 80/<br>Intron 80 | GGTCTGCAGGGTCCAAGAGGCCCCCCTGGCCCA<br>GTG/GTGAGTACCCAAGAACCTTCACCTGTC | 1 |

"/" indicates splice site wherein thymine (T) bases may be uracil (U) bases

In various embodiments, the degree of complementarity between the antisense targeting sequence and the target sequence is sufficient to form a stable duplex. The region of complementarity of the antisense oligomers with the target sequence may be as short as 12-15 bases but can be 12-20 bases or more, e.g., 12-40 bases, 12-30 bases, 12-25 bases, 12-22 bases, 15-25 bases, 15-22 bases, or 15-20 bases, including all integers in between these ranges. An antisense oligomer of about 12-15 bases is generally long enough to have a unique complementary sequence. In certain embodiments, a minimum length of complementary bases may be required to achieve the requisite binding Tm, as discussed herein.

In various aspects, the oligomers are configured for additional functionality, including but not limited to bio-availability, stability, cellular update, and resistance to nuclease degradation. Generally, oligomers comprising 40 bases may be suitable, where at least a minimum number of bases, e.g., 12 bases, are complementary to the target sequence. In various aspects, the oligomers are configured to enhance facilitated or active cellular uptake. In various embodiments, these oligomers are optimized to a length of less than or about 30 bases. In various aspects, the antisense oligomers comprise one or more phosphoramidate morpholino monomer or phosphorodiamidate morpholino monomer subunits. In various embodiments, the antisense oligomers, comprise about 18-25 phosphoramidate morpholino monomer or phosphorodiamidate morpholino monomer subunits. In accordance with a further aspect of the disclosure, the antisense oligomer length and number of modified monomer subunits, including any of a phosphoramidate morpholino monomer or phosphorodiamidate morpholino monomer subunit are varied to obtain an optimum balance of formulation and post-administration stability, and cellular uptake. In certain embodiments, an optimized antisense oligomer comprises 18-25 bases in length with all or substantially all sub-units comprising a phosphoramidate morpholino monomer or phosphorodiamidate morpholino monomer subunit.

In various aspects, the antisense oligomers comprise, consist of, or consist essentially of 12 to 40 subunits, optionally comprising at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an exon/intron splice junction of a human type VII collagen pre mRNA. In various embodiments, the contiguous nucleotides include the exon/intron splice junction human type VII collagen. In further embodiments, the splice junction comprises the splice junction at exon 80/intron 80 (e.g., SEQ ID NO: 1).

Additional aspects include antisense oligomers of 12 to 40 subunits that specifically hybridize to a target region spanning an exon/intron splice junction of human type VII collagen pre-mRNA. The splice junction comprises the splice junction at the intersect of exon 80/intron 80. In embodiments, the splice junction of exon 80/intron 80 comprises the splice junction within SEQ ID NO: 1.

Additional aspects include antisense oligomers having a nucleotide analog subunit comprising a modified sugar moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl) ethyl] subunit, and a morpholino subunit.

Additional aspects include antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

Additional aspects include antisense oligomers having a nucleotide analog subunit comprising at least one combination of a modified sugar moiety and a modified internucleoside linkage, wherein various embodiments, one or more subunits are selected from:

a morpholino subunit optionally substituted with a phosphoramidate internucleoside linkage, a phosphorodiamidate internucleoside linkage, or a phosphorothioate internucleoside linkage, a 2' O-methyl subunit optionally substituted with a phosphoramidate internucleoside linkage, a phosphorodiamidate internucleoside linkage, or a phosphorothioate internucleoside linkage, a 2'O-methoxyethyl subunit optionally substituted with a phosphoramidate internucleoside linkage, a phosphorodiamidate internucleoside linkage, or a phosphorothioate internucleoside linkage, a 2'-fluoro subunit optionally substituted with a phosphoramidate internucleoside linkage, a phosphorodiamidate internucleoside linkage, or a phosphorothioate internucleoside linkages, a 2'O,4'C-ethylene-bridged nucleic acid subunit optionally substituted with a phosphoramidate internucleoside linkage, a phosphorodiamidate internucleoside linkage, or a phosphorothioate internucleoside linkage, a 2'-O-[2-(N-methylcarbamoyl)ethyl] subunit optionally substituted with a phosphoramidate internucleoside linkage, a phosphorodiamidate internucleoside linkage, or a phosphorothioate internucleoside linkage, a tricyclo-DNA subunit optionally substituted with a phosphoramidate internucleoside linkage, a phosphorodiamidate internucleoside linkage, or a phosphorothioate internucleoside linkage, a locked nucleic acid subunit optionally substituted with a phosphoramidate internucleoside linkage, a phosphorodiamidate internucleoside linkage, or a phosphorothioate internucleoside linkage, a morpholino subunit further comprising a phosphorodiamidate internucleoside linkage where a phosphorous atom of the phosphorodiamidate is covalently bonded to the nitrogen atom of the morpholine ring, and is covalently bonded to a (1,4-piperazin)-1-yl moiety or to a substituted (1,4-piperazin)-1-yl moiety, a morpholino subunit further comprising a phosphorodiamidate internucleoside linkage where a phosphorus atom of the phosphorodiamidate is covalently bonded to a 4-aminopiperdin-1-yl moiety or a substituted 4-aminopiperdin-1-yl moiety, a ribose sugar subunit substituted with a phosphorothioate internucleoside or a phosphoramidate internucleoside linkage, a deoxyribose sugar subunit substituted with a phosphorothioate internucleoside linkage or a phosphoramidate internucleoside linkage, a peptide nucleic acid subunit optionally substituted, or any combination of the foregoing.

In various aspects and embodiments, antisense oligomers of the disclosure further comprise a peptide covalently bonded to the antisense oligomer. In various embodiments, an arginine-rich cell-penetrating peptide is conjugated to the 3' or the 5' end of the antisense oligomer.

In embodiments, an antisense oligomer may consist of about 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, or range from 12 to 40, 12 to 30, 14 to 25, 15 to 30, 17 to 30, 17 to 27, 12 to 27, 12 to 25, and 12 to 20 bases. In some embodiments, the antisense oligomer is about 12 to about 40 or about 12 to about 30 bases in length. In some embodiments, the antisense oligomer is about 14 to about 25 or about 17 to about 27 bases in length. In some embodiments, an antisense oligomer sequence comprises at least about 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases that are complementary to the target sequences of Table 1 (e.g., SEQ ID NO: 1), or sequences that span at least a portion of SEQ ID NO: 1.

The antisense oligomers typically comprise a base sequence which is sufficiently complementary to a sequence or region within or adjacent to exon 80, or intron 80 of the pre-mRNA sequence of the human type VII collagen. Ideally, an antisense oligomer is able to effectively modulate aberrant splicing of the human type VII collagen pre-mRNA, and thereby increase expression of functional human type VII collagen protein. This requirement is optionally met when the oligomer compound has the ability to be actively taken up by mammalian cells, and once taken up, form a stable duplex (or heteroduplex) with the target mRNA, optionally with a Tm greater than about 40° C. or 45° C.

"Complementary" or "complementary" as used herein, refers to an antisense oligomer having about 90% to about 100% of the nucleotide sequence complementary to a target sequence. In embodiments, a complementary nucleotide sequence specifically hybridizes to a target sequence to induce a desired effect, for example, a therapeutic effect as described herein. In certain embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo. Hence, certain oligomers may have substantial complementarity, meaning, about or at least about 90% sequence complementarity, e.g., 90%, 91%, 92%, 93%, 94%, 95%, 96%, 97%, 98%, 99% or 100% sequence complementarity, between the oligomer and the target sequence. Oligomer internucleoside linkages that are less susceptible to cleavage by nucleases are provided herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer need not necessarily comprise 100% complementary to the target sequence, it should have sufficient complementarity to effectively, stably and specifically bind to the target sequence, such that splicing of the target pre-mRNA is sufficiently modulated, for example, to achieve a therapeutic effect, as described herein.

Without being bound by theory, the stability of the duplex formed between an oligomer and a target sequence is believed to be a function of the binding Tm and the susceptibility of the duplex to cellular enzymatic cleavage. The Tm of an oligomer with respect to a complementary-sequence RNA duplex may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107, the contents of which are incorporated herein by reference. In various embodiments, the antisense oligomers have a binding Tm, with respect to a complementary-sequence RNA duplex, of greater than body temperature, such as, for example, greater than about 45° C. or 50° C. Tm's in the range 60-80° C. or greater are also included. According to well-known principles, the Tm of an oligomer, with respect to a complementary-based RNA hybrid duplex, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (45-50° C. or greater) at a length of 25 bases or less are generally preferred over those requiring greater than 25 bases for high Tm values.

Table 2 below shows exemplary targeting sequences (in a 5'-to-3' orientation) that are complementary to the exon/intron splice junction relating to exon 80/intron 80 pre-mRNA sequences of the human type VII collagen gene.

TABLE 2

Antisense oligomer sequences for Human Type VII Collagen-targeted oligomers

| Name | Sequence (5'-3') | SEQ ID NO |
|---|---|---|
| COL7A1 Exon 80 Antisense Sequences | | |
| Col7a1-4 D(+27-12) | XXGGGXACXCACCACXGGGCCA | 2 |
| Col7a1-2 D(+31-16) | GXXCXXGGGXACXCACCACXGG | 3 |
| Col7a1-1 D(+34-19) | AAGGXXCXXGGGXACXCACCAC | 4 |
| Col7a1-3 D(+24-09) | GGXACXCACCACXGGGCCAGIG | 6 |

"X" is selected from either uracil (U) or thymine (T)
"I" is inosine

Certain antisense oligomers thus comprise, consist, or consist essentially of a sequence in Table 2 (e.g., SEQ ID NOS: 2, 3, 4 or 6), is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T). For instance, certain antisense oligomers comprise about or at least about 12, 13, 14, 15, 16, 17, 18, 19, 20, 21, 22, 23, 24, 25, 26, 27, 28, 29 or 30 contiguous or non-contiguous nucleotides of any of SEQ ID NOS: 2, 3, 4 or 6. For non-contiguous portions, intervening nucleotides can be deleted or substituted with a different nucleotide, or intervening nucleotides can be added. Additional examples of variants include oligomers having about or at least about 90% sequence identity or homology, e.g., 90%, 91%, 92%, 93%, 94%, 95%, 96%, 97%, 98%, 99% or 100% sequence identity or homology, over the entire length of any of SEQ ID NOS: 2, 3, 4 or 6. In preferred embodiments, the targeting sequence is selected from SEQ ID NOS: 2, 3, 4 or 6.

The activity/functionality of antisense oligomers and variants thereof can be assayed according to routine techniques in the art. For example, splice forms and expression levels of surveyed RNAs may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed oligonucleotide) from a cell, tissue or organism, and by hybridizing the mRNA/cDNA with a reference oligonucleotide that is a complement of the assayed nucleic acid, or a fragment thereof cDNA can, optionally, be amplified using any of a variety of polymerase chain reaction or in vitro transcription methods prior to hybridization with the complementary oligonucleotide; preferably, it is not amplified. Expression of one or more transcripts can also be detected using quantitative PCR to assess the level of expression of the transcript(s).

III. Antisense Oligomer Chemistries

A. General Characteristics

In various aspects and embodiments, the antisense oligomers specifically hybridize to a splice junction region of human type VII collagen pre-mRNA. Exemplary antisense oligomers comprise a targeting sequence set forth in Table 2, a fragment of at least 12 contiguous nucleotides of a targeting sequence in Table 2, or a variant having at least 90% sequence identity to a targeting sequence in Table 2. Other exemplary antisense oligomers consist or consist essentially of a targeting sequence set forth in Table 2.

Nuclease-resistant antisense oligomers are provided in a further aspect. In various embodiments, an antisense oligomer is provided comprising one or more internucleoside linkage modification(s). In other embodiments, an antisense oligomer is provided comprising one or more modified sugar moieties. In other embodiments, an antisense oligomer is provided comprising a combination of one or more modified internucleoside linkages and one or more modified sugar moieties. In other embodiments, an antisense oligomer is provided comprising a modified nucleobase, alone or in combination with any of a modified internucleoside linkage or a modified sugar moiety.

In various embodiments, an antisense oligomer may comprise an oligomer having completely modified internucleoside linkages, for example, 100% of the internucleoside linkages are modified (for example, a 25 mer antisense oligomer comprises 24 internucleoside linkages modified with one or any combination of the modifications as described herein). In various embodiments, an antisense oligomer may comprise about 100% to 2.5% of its internucleoside linkages modified. In various embodiments, an antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its internucleoside linkages modified, and iterations in between. In other embodiments, an antisense oligomer may comprise any combination of modifications as described herein.

In various embodiments, including embodiments in combination with embodiments of percent of modified internucleoside linkages, an antisense oligomer may comprise an oligomer having completely modified sugar moieties, for example, 100% of the sugar moieties are modified (for example, a 25 mer antisense oligomer comprises 25 sugar moieties modified with one or any combination of the modifications as described herein). In various embodiments, an antisense oligomer may comprise about 100% to 2.5% of its sugar moieties modified. In various embodiments, an antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its sugar moieties modified, and iterations in between. In other embodiments, an antisense oligomer may comprise any combination of modifications as described herein.

In various embodiments, the antisense oligomer is substantially uncharged, and is optionally suitable as a substrate for active or facilitated transport across the cell membrane. In some embodiments, all of the internucleoside linkages are uncharged. The ability of the oligomer to form a stable duplex with the target pre-mRNA may also relate to other features of the oligomer, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm.

In various embodiments, the antisense oligomer has at least one internucleoside linkage that is positively charged or cationic at physiological pH. In further embodiments, the antisense oligomer has at least one internucleoside linkage that exhibits a pKa between about 5.5 and about 12. In further embodiments, the antisense oligomer contains about, at least about, or no more than about 1, 2, 3, 4, 5, 6, 7, 8, 9, or 10 internucleoside linkages that exhibits a pKa between about 4.5 and about 12. In some embodiments, the antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. Optionally, the antisense oligomer has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. In some embodiments, the antisense oligomer comprises a morpholine ring. While not being bound by theory, it is believed that the presence of a cationic linkage or linkages (e.g., APN group or APN derivative) in the oligomer facilitates binding to the negatively charged phosphates in the target nucleotide. Thus, the formation of a heteroduplex between mutant RNA and the cationic linkage-containing oligomer may be held together by both an ionic attractive force and Watson-Crick base pairing.

In various embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In further embodiments, an oligomer of about 19-20 monomer subunits may have 2-10, e.g., 4-8, cationic linkages, and the remainder uncharged linkages. In other specific embodiments, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 15 to 20 to 30 or more (including all integers in between), and can be interspersed throughout the oligomer.

In some embodiments, an antisense oligomer may have about or up to about 1 cationic linkage per every 2-5 or 2, 3, 4, or 5 uncharged linkages, such as about 4-5 or 4 or 5 per every 10 uncharged linkages.

Certain embodiments include antisense oligomers that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the internucleoside linkages are cationic. In certain embodiments, enhancement may be seen with a small number e.g., 10-20% cationic linkages, or where the number of cationic linkages are in the range 50-80%, such as about 60%.

In further embodiments, the cationic linkages are interspersed along the internucleoside linkage. Such oligomers optionally contain at least two consecutive uncharged linkages; that is, the oligomer optionally does not have a strictly alternating pattern along its entire length. In specific instances, each one or two cationic linkage(s) is/are separated along the internucleoside linkage by at least 1, 2, 3, 4, or 5 uncharged linkages.

Also included are oligomers having blocks of cationic linkages and blocks of uncharged linkages. For example, a central block of uncharged linkages may be flanked by blocks of cationic linkages, or vice versa. In some embodiments, the oligomer has approximately equal-length 5', 3' and center regions, and the percentage of cationic linkages in the center region is greater than about 50%, 60%, 70%, or 80% of the total number of cationic linkages.

In certain antisense oligomers, the bulk of the cationic linkages (e.g., 70, 75%, 80%, 90% of the cationic linkages) are distributed close to the "center-region" of the internucleoside linkages, e.g., the 6, 7, 8, 9, 10, 11, 12, 13, 14, or 15 centermost linkages. For example, a 16, 17, 18, 19, 20, 21, 22, 23, or 24-mer oligomer may have at least 50%, 60%, 70%, or 80% of the total cationic linkages localized to the 8, 9, 10, 11, or 12 centermost linkages.

B. Chemistry Features

The antisense oligomers may contain a variety of nucleotide analog subunits. Further examples include:

phosphoroamidate containing oligomers, phosphorodiamidate containing oligomers, phosphorothioate containing oligomers, morpholino containing oligomers optionally substituted with a phosphoramidate internucleoside linkage or a phosphorodiamidate internucleoside linkage, 2'O-methyl containing oligomers optionally substituted with a phosphorothioate internucleoside linkage, locked nucleic acid (LNA) containing oligomers optionally substituted with a phosphorothioate internucleoside linkage, 2' O-methoxyethyl (MOE) containing oligomers optionally substituted with a phosphorothioate internucleoside linkage, 2'-fluoro-containing oligomers optionally substituted with a phosphorothioate internucleoside linkage, 2'O,4'C-ethylene-bridged nucleic acids (ENAs) containing oligomers optionally substituted with a phosphorothioate internucleoside linkage, tricyclo-DNA (tc-DNA) containing oligomers optionally substituted with a phosphorothioate internucleoside linkage, 2'-O-[2-(N-methylcarbamoyl)ethyl] containing oligomers optionally substituted with a phosphorothioate internucleoside linkage, morpholino containing oligomers further comprising a phosphorodiamidate internucleoside linkage wherein the phosphorous atom of the phosphorodiamidate is covalently bonded to the nitrogen atom of a morpholine ring, and is covalently bonded to a (1,4-piperazin)-1-yl moiety or to a substituted (1,4-piperazin)-1-yl (PMOplus) moiety, morpholino containing oligomers further comprising a phosphorodiamidate internucleoside linkage wherein the phosphorus atom of the phosphorodiamidate is covalently bonded to the nitrogen atom of a morpholine ring and is covalently bonded to a 4-aminopiperdin-1-yl moiety (i.e., APN) or a substituted 4-aminopiperdin-1-yl (PMO-X) moiety, ribose sugar containing oligomers further comprising a phosphorothioate internucleoside linkage or a phosphoramidate internucleoside linkage, deoxyribose sugar containing oligomers further comprising a phosphorothioate internucleoside linkage oligomer or a phosphoramidate internucleoside linkage, peptide-conjugated phosphorodiamidate morpholino containing oligomers (PPMO) which are further optionally substituted, peptide nucleic acid (PNA) oligomers which are further optionally substituted including further substitutions, and combinations of any of the foregoing.

In certain embodiments, the phosphorous atom of a phosphorodiamidate linkage is further substituted with a (1,4-piperazin)-1-yl moiety, a substituted (1,4-piperazin)-1-yl moiety, a 4-aminopiperidin-1-yl moiety, or a substituted 4-aminopiperidin-1-yl moiety.

In general, PNA and LNA chemistries can utilize shorter targeting sequences because of their relatively high target binding strength relative to PMO and 2'O-Me oligomers. Phosphorothioate and 2'O-Me chemistries can be combined to generate a 2'O-Me-phosphorothioate analog. See, e.g., PCT Publication Nos. WO/2013/112053 and WO/2009/008725, which are hereby incorporated by reference in their entireties.

In some instances, antisense oligomers, such as phosphorodiamidate morpholino oligomers (PMO), can be conjugated to cell penetrating peptides (CPPs) to facilitate intracellular delivery. Peptide-conjugated PMOs are called PPMOs and certain embodiments include those described in PCT Publication No. WO/2012/150960, which is hereby incorporated by reference in its entirety. In some embodiments, an arginine-rich peptide sequence conjugated or linked to, for example, the 3' terminal end of an antisense oligomer as described herein may be used.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The internucleoside linkages of PNAs are formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA oligomer comprising PNA subunits is depicted below:

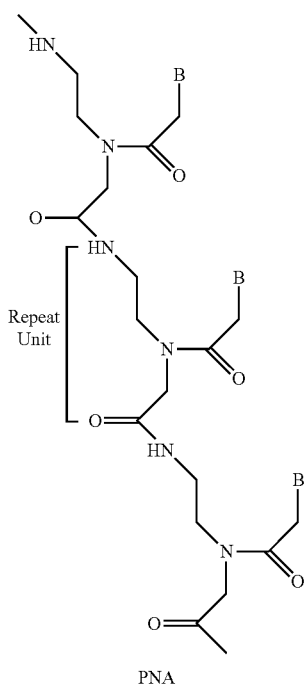

PNA

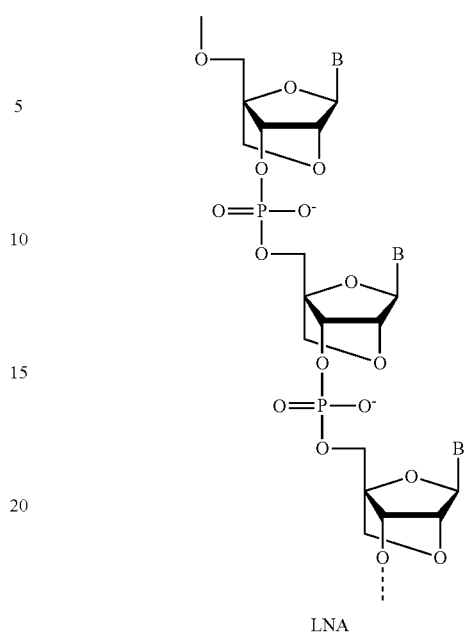

LNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE (Daejeon, Korea) has developed Bts PNA monomers (Bts; benzothiazole-2-sulfonyl group) and oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is hereby incorporated by reference in its entirety.

2. Locked Nucleic Acids (LNAs)

Antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a $C_{3o}$-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230, which are hereby incorporated by reference in their entirety. A non-limiting example of an LNA oligomer comprising LNA subunits and phosphodiester internucleoside linkages is depicted below:

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572,582, 7,569,575, 7,084,125, 7,060,809, 7,053,207, 7,034,133, 6,794,499, and 6,670,461, which are hereby incorporated by reference in their entirety. Typical internucleoside linkers include phosphodiester and phosphorothioate moieties; alternatively, non-phosphorous containing linkers may be employed. Further embodiments include an LNA containing compound where each LNA subunit is separated by a DNA subunit. Certain compounds are composed of alternating LNA and DNA subunits where the internucleoside linker is phosphorothioate.

2'O,4'C-ethylene-bridged nucleic acids (ENAs) are another member of the class of BNAs. A non-limiting example of an ENA subunit and phosphodiester internucleoside linkage is depicted below:

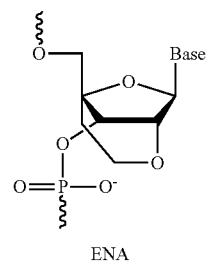

ENA

ENA oligomers and their preparation are described in Obika et al., Tetrahedron Ltt 38(50): 8735, which is hereby incorporated by reference in its entirety. Compounds of the disclosure may incorporate one or more ENA subunits.

3. Phosphorothioates

"Phosphorothioates" (or S-oligos) are a variant of native DNA or RNA in which one of the nonbridging oxygens of the phosphodiester internucleoside linkages is replaced by sulfur. A non-limiting example of a phosphorothioate DNA (left), comprising deoxyribose subunits and phosphorothioate internucleoside linkages, and phosphorothioate RNA (right), comprising ribose subunits and phosophorothioate internucleoside linkages, are depicted below:

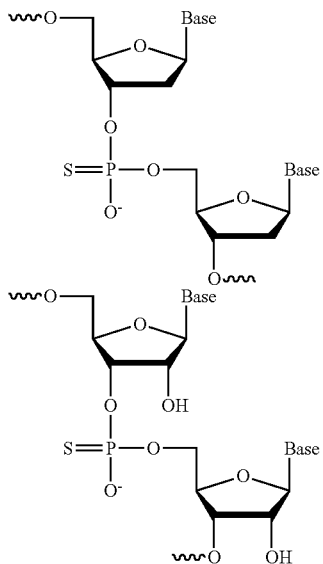

The sulfurization of the internucleoside bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates may be made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which are hereby incorporated by reference in their entirety). The latter methods avoid the problem of elemental sulfur's insolubility in most organic solvents and the toxicity of carbon disulfide. The TETD and BDTD methods also yield higher purity phosphorothioates.

4. Tricyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle α. Homobasic adenine- and thymine-containing tc-DNAs form extraordinarily stable A-T base pairs with complementary RNAs. Tricyclo-DNAs and their synthesis are described in PCT Publication No. WO 2010/115993, which is hereby incorporated by reference in its entirety. Compounds of the disclosure may incorporate one or more tricyclo-DNA subunits; in some cases, the compounds may be entirely composed of tricyclo-DNA subunits.

Tricyclo-phosphorothioate nucleotides are tricyclo-DNA subunits with phosphorothioate internucleoside linkages. Tricyclo-phosphorothioate nucleotides and their synthesis are described in PCT Publication No. WO 2013/053928, which is hereby incorporated by reference in its entirety. Compounds of the disclosure may incorporate one or more tricyclo-DNA subunits; in some cases, the compounds may be entirely composed of tricyclo-DNA nucleotides. A non-limiting example of a tricyclo-DNA/tricycle subunit and phosphodiester internucleoside linkage is depicted below:

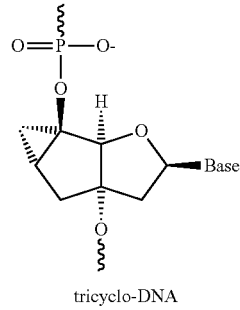

tricyclo-DNA 5. 2' O-Methyl, 2' O-MOE, and 2'-F Oligomers

"2'O-Me oligomer" molecules comprise subunits that carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphorothioate oligomers (PTOs) for further stabilization. 2'O-Me oligomers (wherein the 2'OMe subunits are connected by phosphodiester or phosphorothioate internucleoside linkages) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer comprising 2'OMe subunits and phosphodiester intersubunit linkages is depicted below:

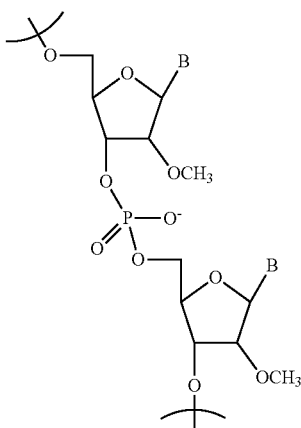

2' O-Me oligomers may also comprise a phosphorothioate linkage (2' O-Me phosphorothioate oligomers). 2' O-Methoxyethyl Oligomers (2'-O MOE), like 2' O-Me oligomers, comprise subunits that carry a methoxyethyl group at the 2'-OH residue of the ribose molecule and are discussed in Martin el al., Helv. Chim. Acta, 78, 486-504, 1995, which is hereby incorporated by reference in its entirety. A non-limiting example of a 2' O-MOE subunit is depicted below:

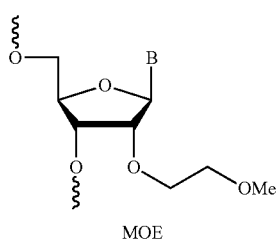

MOE

In contrast to the preceding alkylated 2'OH ribose derivatives, 2'-fluoro oligomers comprise subunits that have a fluoro radical in at the 2' position in place of the 2'OH. A non-limiting example of a 2'-F oligomer comprising 2'-F subunits and phosphodiester internucleoside linkages is depicted below:

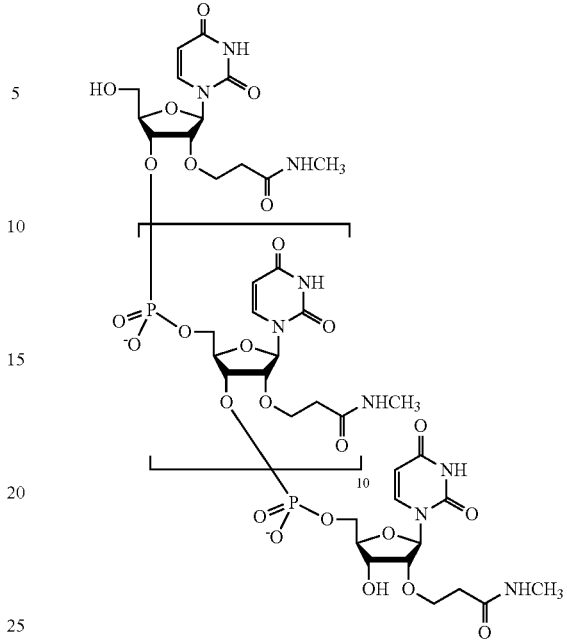

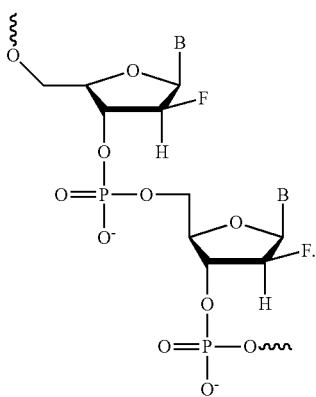

2'-fluoro oligomers are further described in WO 2004/043977, which is hereby incorporated by reference in its entirety. Compounds of the disclosure may incorporate one or more 2'O-Methyl, 2' O-MOE, and 2'-F subunits and may utilize any of the internucleoside linkages described here. In some instances, a compound of the disclosure could be composed of entirely 2'O-Methyl, 2' O-MOE, or 2'-F subunits. One embodiment of a compound of the disclosure is composed entirely of 2'O-methyl subunits.

6. 2'-O-[2-(N-methylcarbamoyl)ethyl] Oligomers (MCEs)

MCEs are another example of 2'O modified ribonucleosides useful in the compounds of the disclosure. Here, the 2'OH is derivatized to a 2-(N-methylcarbamoyl)ethyl moiety to increase nuclease resistance. A non-limiting example of an MCE oligomer comprising MCE subunits and phosphodiester internucleoside linkages is depicted below:

MCEs and their synthesis are described in Yamada et al., J Org. Chem., 76(9):3042-53, which is hereby incorporated by reference in its entirety. Compounds of the disclosure may incorporate one or more MCE subunits.

7. Morpholino-Based Oligomers

Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic internucleoside linkages of the morpholino-based oligomers described herein, one nitrogen is always pendant to the linkage chain. The second nitrogen, in a phosphorodiamidate linkage, is typically the ring nitrogen in a morpholine ring structure.

"PMO-X" refers to phosphorodiamidate morpholino-based oligomers having a phosphorus atom with (i) a covalent bond to the nitrogen atom of a morpholine ring and (ii) a second covalent bond to the ring nitrogen of, for example, a 4-aminopiperdin-1-yl (i.e., APN) or a derivative of 4-aminopiperdin-1-yl. Exemplary PMO-X oligomers are disclosed in PCT Application No. PCT/US2011/38459 and PCT Publication No. WO 2013/074834, which are hereby incorporated by reference in their entirety. PMO-X includes "PMO-apn" or "APN," which refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, an antisense oligomer comprising a targeting sequence as set forth in Table 2 comprises at least one APN-containing linkage or APN derivative-containing linkage. Various embodiments include morpholino-based oligomers that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In various embodiments, the antisense oligomer is a compound of formula (I):

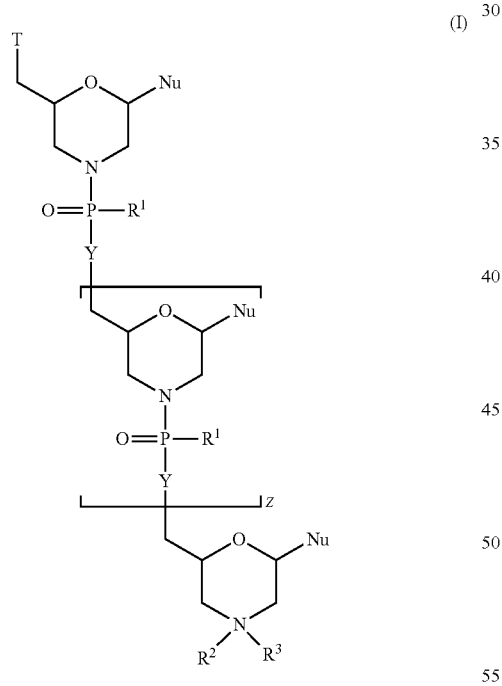

or a pharmaceutically acceptable salt thereof, wherein:

each Nu is a nucleobase which taken together forms a targeting sequence;

Z is an integer from 10 to 38;

each Y is independently selected from O and —NR$^4$, wherein each R$^4$ is independently selected from H, C$_1$-C$_6$ alkyl, aralkyl, —C(=NH)NH$_2$, —C(O)(CH$_2$), NR$^5$C(=NH)NH$_2$, —C(O)(CH$_2$)$_2$NHC(O)(CH$_2$)$_5$ NR$^5$C(=NH)NH$_2$, and G, wherein R$^5$ is selected from H and C$_1$-C$_6$ alkyl and n is an integer from 1 to 5;

T is selected from OH and a moiety of the formula:

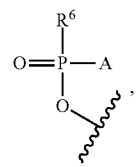

wherein:

A is selected from —OH, —N(R$^7$)$_2$R$^8$, and R$^1$ wherein:
each R$^7$ is independently selected from H and C$_1$-C$_6$ alkyl, and
R$^8$ is selected from an electron pair and H, and
R$^6$ is selected from OH, —N(R)CH$_2$C(O)NH$_2$, and a moiety of the formula:

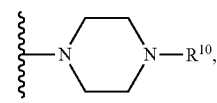

wherein:

R$^9$ is selected from H and C$_1$-C$_6$ alkyl; and
R$^{10}$ is selected from G, —C(O)—R$^{11}$OH, acyl, trityl, 4-methoxytrityl, —C(=NH)NH$_2$, —C(O)(CH$_2$)$_m$ NR$^{12}$C(=NH)NH$_2$, and —C(O)(CH$_2$)$_2$NHC(O) (CH$_2$)$_5$NR$^{12}$C(=NH)NH$_2$, wherein:
m is an integer from 1 to 5,
R$^{11}$ is of the formula —(O-alkyl)$_y$- wherein y is an integer from 3 to 10 and
each of the y alkyl groups is independently selected from C$_2$-C$_6$ alkyl; and
R$^{12}$ is selected from H and C$_1$-C$_6$ alkyl;

each instance of R$^1$ is independently selected from:

—N(R$^{13}$)$_2$R$^{14}$ wherein each R$^{13}$ is independently selected from H and C$_1$-C$_6$ alkyl, and R$^{14}$ is selected from an electron pair and H;

a moiety of formula (II):

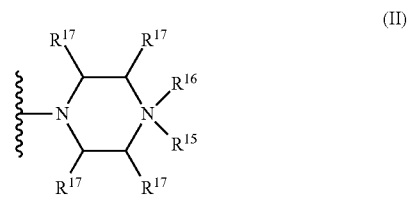

wherein:

R$^{15}$ is selected from H, G, C$_1$-C$_6$ alkyl, —C(=NH)NH$_2$, —C(O)(CH$_2$)$_q$NR$^{18}$C(=NH) NH$_2$, and —C(O)(CH$_2$)$_2$NHC(O)(CH$_2$)$_5$NR$^{18}$C (=NH)NH$_2$, wherein:
R$^{18}$ is selected from H and C$_1$-C$_6$ alkyl; and
q is an integer from 1 to 5,
R$^{16}$ is selected from an electron pair and H; and
each R$^{17}$ is independently selected from H and methyl; and a moiety of formula (III):

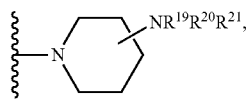

wherein:
R$^{19}$ is selected from H, C$_1$-C$_6$ alkyl, —C(=NH)NH$_2$, —C(O)(CH$_2$)$_r$NR$^{22}$C(=NH)NH$_2$, —C(O)CH(NH$_2$)(CH$_2$)$_3$NHC(=NH)NH$_2$, —C(O)(CH$_2$)$_2$NHC(O)(CH$_2$)$_5$NR$^{22}$C(=NH)NH$_2$, —C(O)CH(NH$_2$)(CH$_2$)$_4$NH$_2$, and G
wherein:
R$^{22}$ is selected from H and C$_1$-C$_6$ alkyl; and
r is an integer from 1 to 5,
R$^{20}$ is selected from H and C$_1$-C$_6$ alkyl; and
R$^{21}$ is selected from an electron pair and H;
R$^2$ is selected from H, G, acyl, trityl, 4-methoxytrityl, C$_1$-C$_6$ alkyl, —C(=NH)NH$_2$, —C(O)—R$^{23}$, —C(O)(CH$_2$)$_5$NR$^{24}$C(=NH)NH$_2$, —C(O)(CH$_2$)$_2$NHC(O)(CH$_2$)$_5$NR$^{24}$C(=NH)NH$_2$, —C(O)CH(NH$_2$)(CH$_2$)$_3$NHC(=NH)NH$_2$,
and a moiety of the formula:

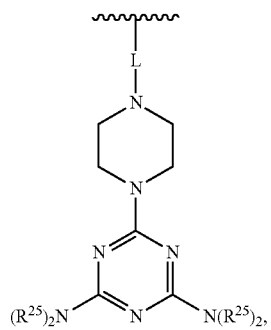

wherein,
R$^{23}$ is of the formula —(O-alkyl)$_v$-OH, wherein v is an integer from 3 to 10 and each of the v alkyl groups is independently selected from C$_2$-C$_6$ alkyl; and
R$^{24}$ is selected from H and C$_1$-C$_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each R$^{25}$ is of the formula —(CH$_2$)$_2$OC(O)N(R$^{26}$)$_2$ wherein each R$^{26}$ is of the formula —(CH$_2$)$_6$NHC(=NH)NH$_2$; and
R$^3$ is selected from an electron pair, H, and C$_1$-C$_6$ alkyl, wherein G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

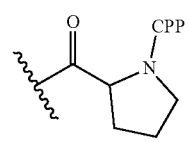

wherein the CPP is attached to the linker moiety by an amide bond at the CPP carboxy terminus, with the proviso that up to one instance of G is present.

In various embodiments, the targeting sequence is complementary to or spanning at least a portion of a splice junction region within exon 80/intron 80 (e.g., SEQ ID NO: 1) of the human type VII collagen pre-mRNA. In some embodiments, the targeting sequence is complementary to 12 or more contiguous nucleotides in a target region spanning an exon/intron junction of human type VII collagen pre-mRNA, said exon/intron splice junction comprises the splice junction of exon 80/intron 80. In various embodiments, the contiguous nucleotides include the exon/intron splice junction.

In various embodiments, the targeting sequence comprises one of SEQ ID NOS: 2, 3, 4 or 6, is selected from one of SEQ ID NOS: 2, 3, 4 or 6, is a fragment of at least 12 contiguous nucleotides of a sequence selected from at least one of SEQ ID NOS: 2, 3, 4 or 6, or is a variant having at least 90% sequence identity to a sequence selected from at least one of SEQ ID NOS: 2, 3, 4 or 6, where X is selected from uracil (U) or thymine (T), and wherein I is inosine.

In some embodiments, the targeting sequence of formula (I) is selected from:

a)
```
                                    SEQ ID NO: 2
(XXGGGXACXCACCACXGGGCCA)
wherein
Z is 22;
``` b)
```
                                    SEQ ID NO: 3
(GXXCXXGGGXACXCACCACXGG)
wherein
Z is 22;
``` c)
```
                                    SEQ ID NO: 4
(AAGGXXCXXGGGXACXCACCAC)
wherein
Z is 22;
and
``` d)
```
                                    SEQ ID NO: 6
(GGXACXCACCACXGGGCCAGIG)
wherein
Z is 22;
``` wherein X is selected from uracil (U) or thymine (T), and wherein I is inosine.

In some embodiments, R$^3$ is a moiety of the formula:

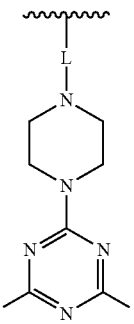

where L is selected from —C(O)(CH$_2$)$_6$C(O)— or —C(O)(CH$_2$)$_2$S$_2$(CH$_2$)$_2$C(O)—, and and each $R^{25}$ is of the formula $-(CH_2)_{20}C(O)N(R^{26})_2$ wherein each $R^{26}$ is of the formula $-(CH_2)_6NHC(=NH)NH_2$. Such moieties are further described in U.S. Pat. No. 7,935,816, which is hereby incorporated by reference in its entirety.

In certain embodiments, $R^3$ may comprise either moiety depicted below:

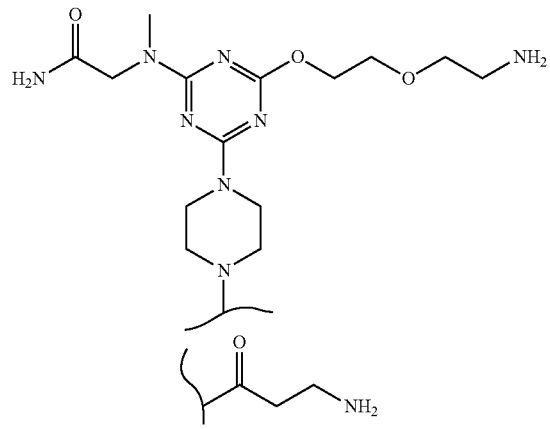

In various embodiments, Y is O, $R^2$ is selected from H or G, $R^3$ is selected from an electron pair or H. In some embodiments, $R^2$ is G wherein the CPP is of a sequence selected from SEQ ID NOS: 9-24. In certain embodiments, $R^2$ is H.

In certain embodiments, each $R^1$ is $-N(CH_3)_2$. In some embodiments, about 50-90% of the $R_1$ groups are dimethylamino (i.e. $-N(CH_3)_2$). In certain embodiments, about 66% of the $R_1$ groups are dimethylamino.

In some embodiments of the disclosure, $R_1$ may be selected from:

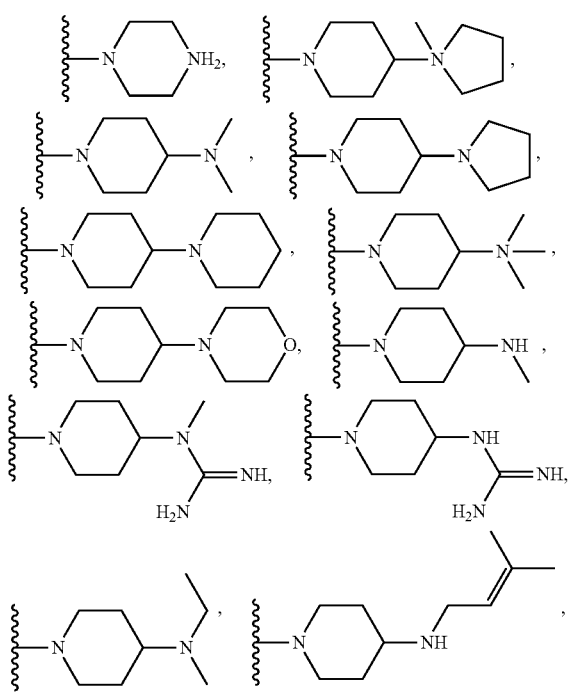

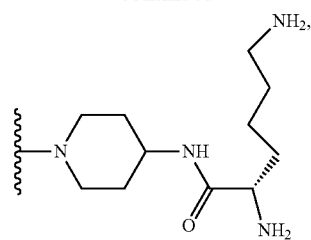

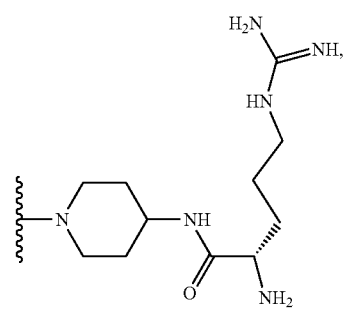

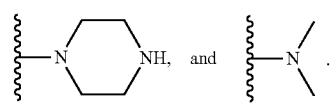

In some embodiments, at least one $R^1$ is:

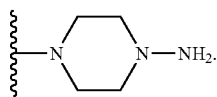

In certain embodiments, T is of the formula:

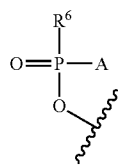

wherein A is $-N(CH_3)_2$, and $R^6$ is of the formula:

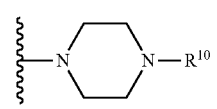

wherein $R^{10}$ is $-C(O)R_{11}OH$.

In some embodiments, Y is O, and T is selected from:

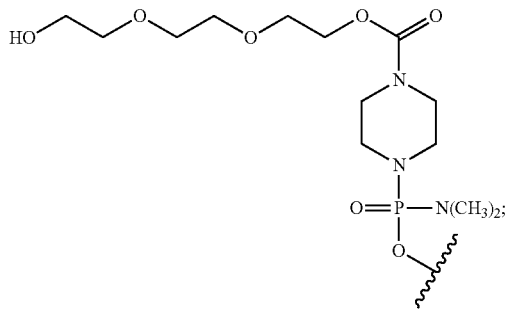

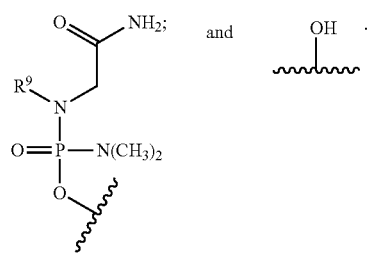

In certain embodiments, T is of the formula:

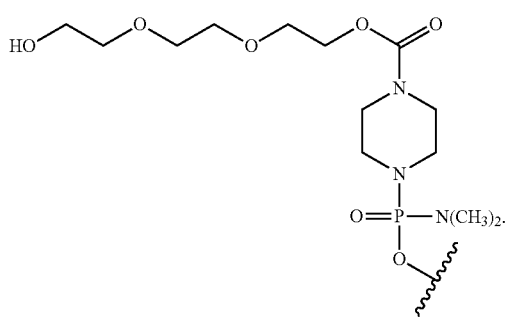 [SMILES: *OP(=O)(N(C)C)N1CCN(C(=O)OCCOCCOCCO)CC1]

In various embodiments, Y is O, R² is selected from H or G, R³ is selected from an electron pair or H. In some embodiments, R² is G, wherein the CPP is of a sequence selected from SEQ ID NOS: 9-24 described below.

In other embodiments, the antisense oligomer is a compound of formula (IV):

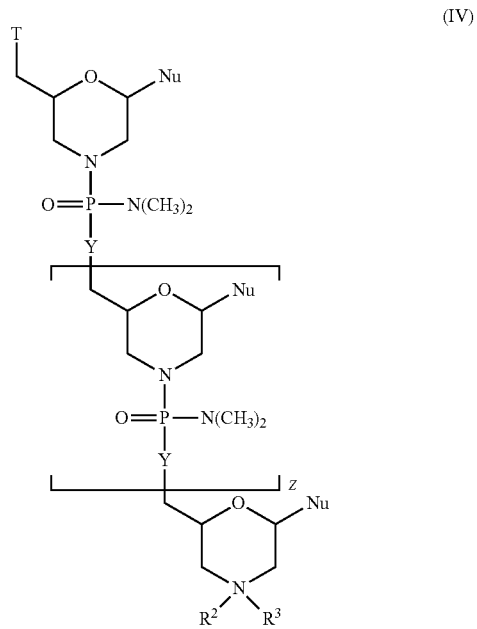

(IV)

or a pharmaceutically acceptable salt thereof, where:
  each Nu is a nucleobase which taken together forms a targeting sequence;
  Z is an integer from 10 to 38;
  each Y is independently selected from O and —NR⁴, wherein each R⁴ is independently selected from H, $C_1$-$C_6$ alkyl, aralkyl, —C(=NH)NH₂, —C(O)(CH₂), NR⁵C(=NH)NH₂, —C(O)(CH₂)₂NHC(O)(CH₂) NR⁵C(=NH)NH₂, and G, wherein R⁵ is selected from H and $C_1$-$C_6$ alkyl and n is an integer from 1 to 5;
  T is selected from OH and a moiety of the formula:

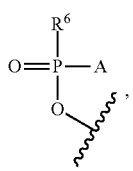

wherein:
  A is selected from —OH and —N(R⁷)₂R⁸, wherein:
    each R⁷ is independently selected from H and $C_1$-$C_6$ alkyl, and
    R⁸ is selected from an electron pair and H, and
  R⁶ is selected from OH, —N(R⁹)CH₂C(O)NH₂, and a moiety of the formula:

wherein:
  R⁹ is selected from H and $C_1$-$C_6$ alkyl; and
  R¹⁰ is selected from G, —C(O)—R¹¹OH, acyl, trityl, 4-methoxytrityl, —C(=NH)NH₂, —C(O)

$(CH_2)_m NR^{12}C(=NH)NH_2$, and $—C(O)(CH_2)_2NHC(O)(CH_2)_5NR^{12}C(=NH)NH_2$, wherein:

m is an integer from 1 to 5, $R^{11}$ is of the formula $—(O\text{-alkyl})_y-$ wherein y is an integer from 3 to 10 and each of the y alkyl groups is independently selected from $C_2$-$C_6$ alkyl; and $R^{12}$ is selected from H and $C_1$-$C_6$ alkyl;

$R^2$ is selected from H, G, acyl, trityl, 4-methoxytrityl, $C_1$-$C_6$ alkyl, $—C(=NH)NH_2$, and $—C(O)—R^{23}$; and $R^3$ is selected from an electron pair, H, and $C_1$-$C_6$ alkyl.

In various embodiments, the targeting sequence is complementary to or spans at least a portion of a splice junction region within exon 80/intron 80 (e.g., SEQ ID NO: 1) of the human type VII collagen pre-mRNA. In some embodiments, the targeting sequence is complementary to 12 or more contiguous nucleotides in a target region spanning an exon/intron splice junction of human type VII collagen pre-mRNA, said exon/intron splice junction comprises the splice junction of exon 80/intron 80. In various embodiments, the contiguous nucleotides include the exon/intron splice junction.

In various embodiments, the targeting sequence of compound (IV) comprises a sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6 where X is selected from uracil (U) or thymine (T), and wherein I is inosine.

In some embodiments, the targeting sequence of formula (IV) is selected from:

a)
```
                                    SEQ ID NO: 2
(XXGGGXACXCACCACXGGGCCA)
wherein
Z is 22;
``` b)
```
                                    SEQ ID NO: 3
(GXXCXXGGGXACXCACCACXGG)
wherein
Z is 22;
``` c)
```
                                    SEQ ID NO: 4
(AAGGXXCXXGGGXACXCACCAC)
wherein
Z is 22;
and
``` d)
```
                                    SEQ ID NO: 6
(GGXACXCACCACXGGGCCAGIG)
wherein
Z is 22;
``` wherein X is selected from uracil (U) or thymine (T), and wherein I is inosine.

In various embodiments, Y is O, $R^2$ is selected from H or G, $R^3$ is selected from an electron pair or H. In some embodiments, $R^2$ is G, wherein the CPP is of a sequence selected from SEQ ID NOS: 9-24. In certain embodiments, $R^2$ is H.

In some embodiments, Y is O, and T is selected from:

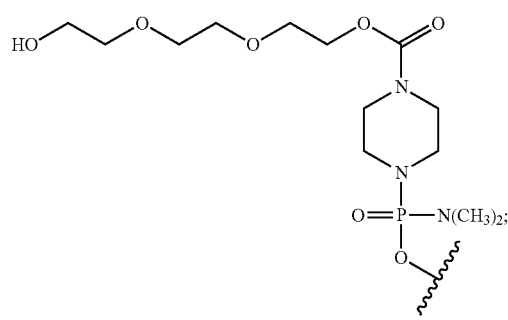

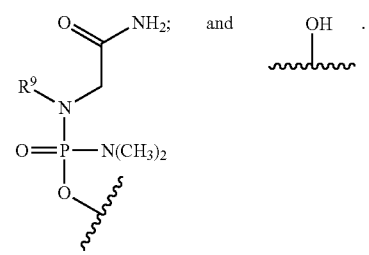

In some embodiments, T is of the formula:

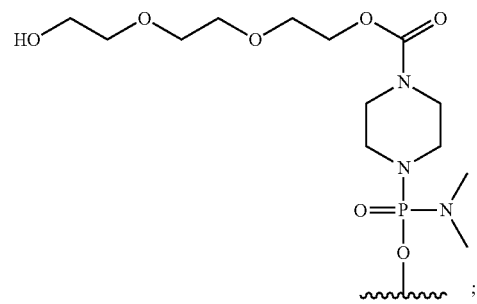 [SMILES: *OP(=O)(N(C)C)N1CCN(C(=O)OCCOCCOCCO)CC1]

$R^2$ is hydrogen; and $R^3$ is an electron pair.

In some embodiments, the antisense oligomer is a compound of formula (V):

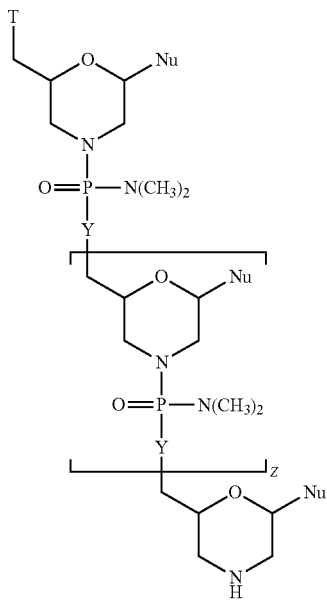

(V)

or a pharmaceutically acceptable salt thereof, where:
each Nu is a nucleobase which taken together forms a targeting sequence;
Z is an integer from 10 to 38;
each Y is independently selected from O and —$NR^4$ wherein each $R^4$ is independently selected from H, $C_1$-$C_6$ alkyl, aralkyl, —C(=NH)$NH_2$, —C(O)$(CH_2)_n$$NR^5$C(=NH)$NH_2$, —C(O)$(CH_2)_2$NHC(O)$(CH_2)_5$$NR^5$C(=NH)$NH_2$, and G, wherein $R^5$ is selected from H and $C_1$-$C_6$ alkyl and n is an integer from 1 to 5;
T is selected from OH and a moiety of the formula:

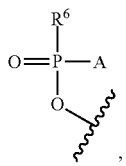

wherein:
A is selected from —OH and —N($R^7$)$_2$$R^8$, wherein:
each $R^7$ is independently selected from H and $C_1$-$C_6$ alkyl, and
$R^8$ is selected from an electron pair and H, and
$R^6$ is selected from OH, —N($R^9$)$CH_2$C(O)$NH_2$, and a moiety of the formula:

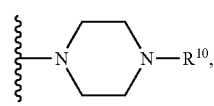

wherein:
$R^9$ is selected from H and $C_1$-$C_6$ alkyl; and
$R^{10}$ is selected from G, —C(O)—$R^{11}$OH, acyl, trityl, 4-methoxytrityl, —C(=NH)$NH_2$, —C(O)

$(CH_2)_m$$NR^{12}$C(=NH)$NH_2$, and —C(O)$(CH_2)_2$NHC(O)$(CH_2)_5$$NR^{12}$C(=NH)$NH_2$, wherein:
m is an integer from 1 to 5,
$R^{11}$ is of the formula —(O-alkyl)$_y$-, wherein y is an integer from 3 to 10 and
each of the y alkyl groups is independently selected from $C_2$-$C_6$ alkyl; and
$R^{12}$ is selected from H and $C_1$-$C_6$ alkyl;
wherein G is a cell penetrating peptide ("CPP") and linker moiety selected from —C(O)$(CH_2)_5$NH—CPP, —C(O)$(CH_2)_2$NH—CPP, —C(O)$(CH_2)_2$NHC(O)$(CH_2)_5$NH—CPP, and —C(O)$CH_2$NH—CPP, or G is of the formula:

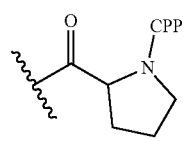

wherein the CPP is attached to the linker moiety by an amide bond at the CPP carboxy terminus, with the proviso that up to one instance of G is present.

In various embodiments, the targeting sequence is complementary to or spans at least a portion of a splice junction region within exon 80/intron 80 (e.g., SEQ ID NO: 1) of a human type VII collagen pre-mRNA. In some embodiments, the targeting sequence is complementary to 12 or more contiguous nucleotides in a target region spanning an exon/intron junction of human type VII collagen pre-mRNA, said junction comprises the splice junction of exon 80/intron 80. In various embodiments, the contiguous nucleotides include the exon/intron splice junction.

In various embodiments, the targeting sequence of compound (V) comprises a sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T), and wherein I is inosine.

In some embodiments, the targeting sequence of formula (V) is selected from:

a)
```
                                        SEQ ID NO: 2
(XXGGGXACXCACCACXGGGCCA)
wherein
Z is 22;
``` b)
```
                                        SEQ ID NO: 3
(GXXCXXGGGXACXCACCACXGG)
wherein
Z is 22;
``` c)
```
                                        SEQ ID NO: 4
(AAGGXXCXXGGGXACXCACCAC)
wherein
Z is 22;
and
``` d)
```
                                        SEQ ID NO: 6
(GGXACXCACCACXGGGCCAGIG)
wherein
Z is 22;
``` wherein X is selected from uracil (U) or thymine (T), and wherein I is inosine.

In some embodiments, Y is O, and T is selected from:

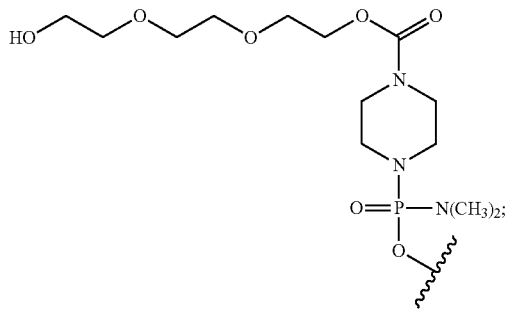

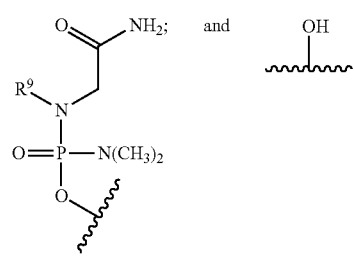

In some embodiments, T is of the formula:

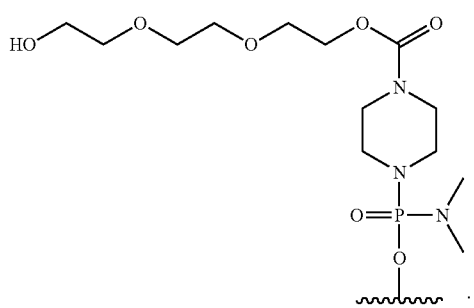 [SMILES: *OP(=O)(N(C)C)N1CCN(C(=O)OCCOCCOCCO)CC1]

In certain embodiments, the antisense oligomer of the disclosure is a compound of formula (VI):

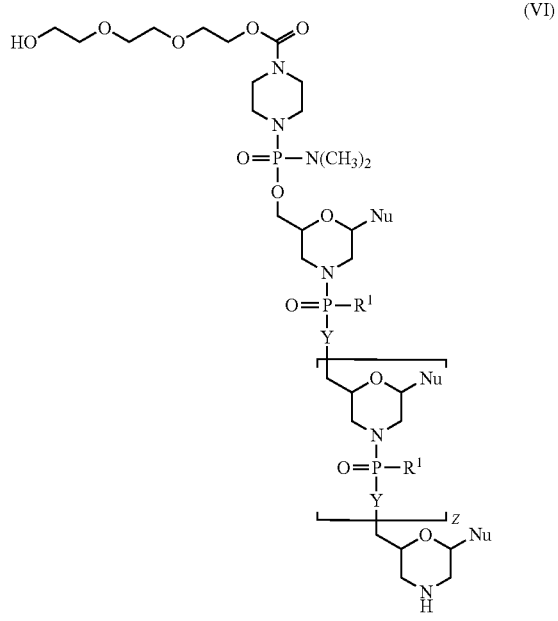  (VI)

or a pharmaceutically acceptable salt thereof, where:
each Nu is a nucleobase which taken together form a targeting sequence;
Z is an integer from 15 to 25;
each Y is O;
each $R^1$ is independently selected from:

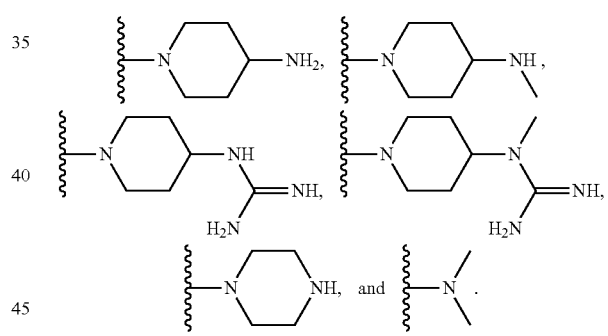

In various embodiments, at least one $R^1$ is —N(CH$_3$)$_2$. In some embodiments, each $R^1$ is —N(CH$_3$)$_2$.

In various embodiments, the targeting sequence is complementary to or spans at least a portion of a splice junction region within exon 80/intron 80 (e.g., SEQ ID NO: 1) of the human type VII collagen pre-mRNA. In some embodiments, the targeting sequence is complementary to 12 or more contiguous nucleotides in a target region spanning an exon/intron junction of human type VII collagen pre-mRNA, said junction comprises the splice junction of exon 80/intron 80. In various embodiments, the contiguous nucleotides include the exon/intron splice junction.

In various embodiments, the targeting sequence of compound (VI) comprises a sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T), and wherein I is inosine.

In some embodiments, the targeting sequence of formula (VI) is selected from:

a)
```
(XXGGGXACXCACCACXGGGCCA)
wherein
Z is 22;
```
SEQ ID NO: 2 b)
```
(GXXCXXGGGXACXCACCACXGG)
wherein
Z is 22;
```
SEQ ID NO: 3 c)
```
(AAGGXXCXXGGGXACXCACCAC)
wherein
Z is 22;
and
```
SEQ ID NO: 4 d)
```
(GGXACXCACCACXGGGCCAGIG)
wherein
Z is 22;
```
SEQ ID NO: 6 wherein X is selected from uracil (U) or thymine (T), and wherein I is inosine.

In some embodiments, the antisense oligomer is a compound of formula (VII):

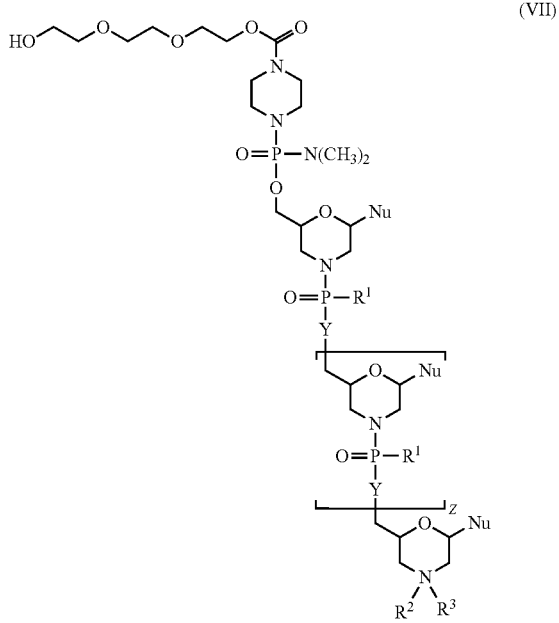

(VII)

or a pharmaceutically acceptable salt thereof, where:

each Nu is a nucleobase which taken together form a targeting sequence; and

Z is an integer from 10 to 38;

each Y is O;

each $R^1$ is independently selected from:

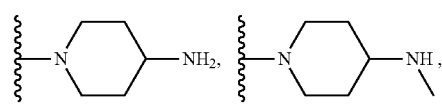

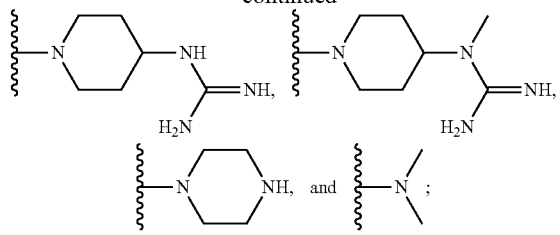

$R^2$ is selected from H, acyl, trityl, 4-methoxytrityl, $C_1$-$C_6$ alkyl, —C(=NH)$NH_2$, and —C(O)—$R^{23}$; and $R^3$ is selected from an electron pair, H, and $C_1$-$C_6$ alkyl.

In various embodiments, the targeting sequence is complementary to or spans at least a portion of a splice junction region within exon 80/intron 80 (e.g., SEQ ID NO: 1) of the human type VII collagen pre-mRNA. In some embodiments, the targeting sequence is complementary to 12 or more contiguous nucleotides in a target region spanning an exon/intron splice junction of human type VII collagen pre-mRNA, said exon/intron junction comprises the splice junction of exon 80/intron 80. In various embodiments, the contiguous nucleotides include the exon/intron splice junction.

In various embodiments, the targeting sequence of compound (VII) comprises a sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T), and wherein I is inosine.

In some embodiments, the targeting sequence of formula (VII) is selected from:

a)
```
(XXGGGXACXCACCACXGGGCCA)
wherein
Z is 22;
```
SEQ ID NO: 2 b)
```
(GXXCXXGGGXACXCACCACXGG)
wherein
Z is 22;
```
SEQ ID NO: 3 c)
```
(AAGGXXCXXGGGXACXCACCAC)
wherein
Z is 22;
and
```
SEQ ID NO: 4 d)
```
(GGXACXCACCACXGGGCCAGIG)
wherein
Z is 22;
```
SEQ ID NO: 6 wherein X is selected from uracil (U) or thymine (T), and wherein I is inosine.

In various embodiments, Y is O, $R^2$ is selected from H or G, $R^3$ is selected from an electron pair or H. In some embodiments, $R^2$ is G, wherein the CPP is a sequence selected from SEQ ID NOS: 9-24. In certain embodiments, $R^2$ is H.

In certain embodiments, the antisense oligomer is a compound of formula (VIII):

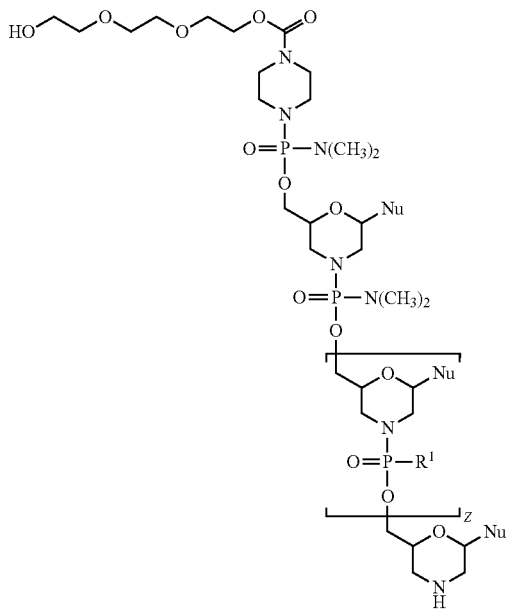

(VIII)

or a pharmaceutically acceptable salt thereof, where:

each Nu is a nucleobase which taken together form a targeting sequence; and

Z is an integer from 10 to 38.

In various embodiments, the targeting sequence is complementary to or spans at least a portion of a splice junction region within exon 80/intron 80 (e.g., SEQ ID NO: 1) of the human type VII collagen pre-mRNA. In some embodiments, the targeting sequence is complementary to 12 or more contiguous nucleotides in a target region spanning an exon/intron splice junction of human type VII collagen pre-mRNA, said junction comprises the splice junction of exon 80/intron 80. In various embodiments, the contiguous nucleotides include the exon/intron splice junction.

In various embodiments, the targeting sequence of compound (VIII) comprises a sequence selected from SEQ ID NOS: 2, 3, 4 or 6, is selected from SEQ ID NOS: 2, 3, 4 or 6, is a fragment of at least 12 contiguous nucleotides of a targeting sequence selected from SEQ ID NOS: 2, 3, 4 or 6, or is a variant having at least 90% sequence identity to a targeting sequence selected from SEQ ID NOS: 2, 3, 4 or 6, where X is selected from uracil (U) or thymine (T), and wherein I is inosine.

In some embodiments, the targeting sequence of compound (VIII) is selected from:

a)
SEQ ID NO: 2
(XXGGGXACXCACCACXGGGCCA)
wherein
Z is 22;

b)
SEQ ID NO: 3
(GXXCXXGGGXACXCACCACXGG)
wherein
Z is 22;

c)
SEQ ID NO: 4
(AAGGXXCXXGGGXACXCACCAC)
wherein
Z is 22;
and d)
SEQ ID NO: 6
(GGXACXCACCACXGGGCCAGIG)
wherein
Z is 22;

wherein X is selected from uracil (U) or thymine (T), and wherein I is inosine.

In some embodiments, each Nu of the antisense oligomers of the disclosure, including compounds of formula (I), (IV), (V), (VI), (VII) and (VIII), is independently selected from adenine, guanine, thymine, uracil, cytosine, hypoxanthine (inosine), 2,6-diaminopurine, 5-methyl cytosine, $C_5$-propynyl-modified pyrimidines, and 10-(9-(aminoethoxy)phenoxazinyl). In some embodiments, the targeting sequence of the antisense oligomers of the disclosure, including compounds of formula (I), (IV), (V), (VI), (VII) and (VIII), comprises a sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T), and wherein I is inosine.

Additional antisense oligomers/chemistries that can be used in accordance with the present disclosure include those described in the following patents and patent publications, which are hereby incorporated by reference in their entirety: PCT Publication Nos. WO 2007/002390; WO 2010/120820; and WO 2010/148249; U.S. Pat. No. 7,838,657; and U.S. Patent Application No. 2011/0269820.

C. The Preparation of Morpholino Subunits and Phosphoroamidate Internucleoside Linkers Morpholino monomer subunits, the modified internucleoside linkages, and oligomers comprising the same can be prepared as described, for example, in U.S. Pat. Nos. 5,185,444, and 7,943,762, which are hereby incorporated by reference in their entirety. The morpholino subunits can be prepared according to the following general Reaction Scheme I Reaction Scheme 1. Prepartion, Protection, and Activation of Morpholino Subunit

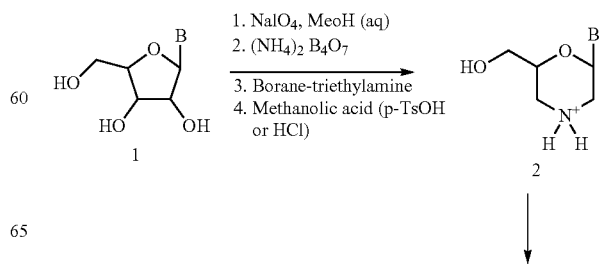

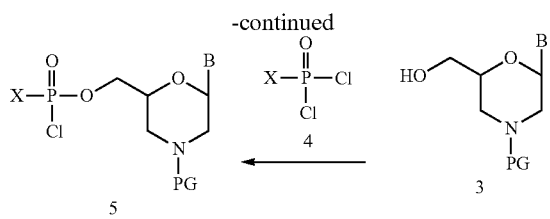

Referring to Reaction Scheme 1, where B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in U.S. Pat. No. 8,076,476, which is hereby incorporated by reference in its entirety.

Reaction of compound 3 with the activated phosphorous compound 4, results in morpholino subunits having the desired linkage moiety compound 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. Nos. 5,185,444, 7,943,762, and 8,779,128, which are hereby incorporated by reference in its entirety.

Compounds of structure 5 can be used in solid-phase automated oligomer synthesis for preparation of oligomers comprising the internucleoside linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$. An exemplary method is demonstrated in FIG. 1A. Once supported, the protecting group (e.g., trityl) is removed and the free amine is reacted with an activated phosphorous moiety of a second compound of structure 5. This sequence is repeated until the desired length of oligo is obtained. The protecting group in the terminal 5' end may either be removed or left on if a 5'-modification is desired. The oligo can be removed from the solid support using any number of methods, for example treatment with DTT followed by ammonium hydroxide.

The preparation of modified morpholino subunits and morpholino-based oligomers are described in more detail in the Examples. The morpholino-based oligomers containing any number of modified linkages may be prepared using methods described herein, methods known in the art and/or described by reference herein. Also described in the examples are global modifications of morpholino-based oligomers prepared as previously described (see e.g., PCT Publication No. WO 2008/036127, which is hereby incorporated by reference in its entirety).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999), which is hereby incorporated by reference in its entirety. It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

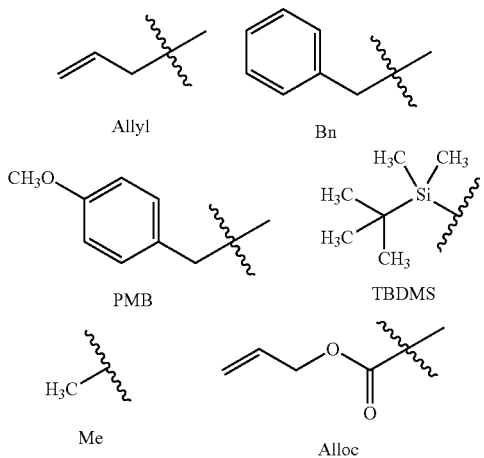

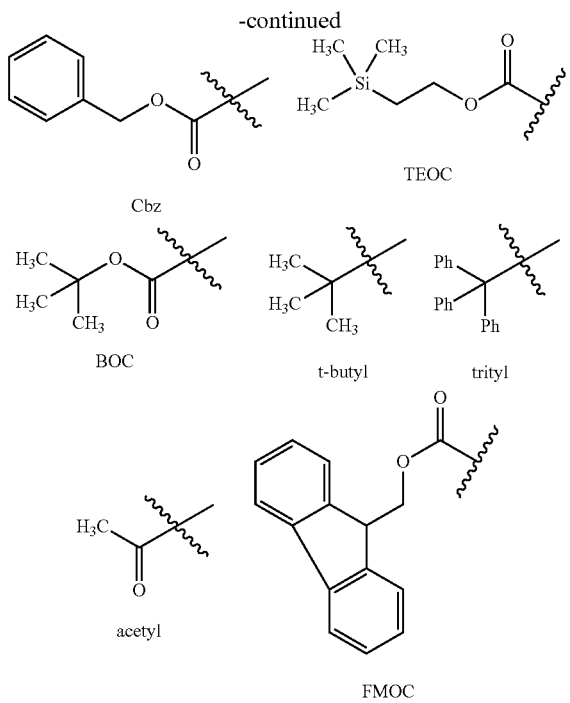

Cbz, TEOC, BOC, t-butyl, trityl, acetyl, FMOC

Unless otherwise noted, all chemicals were obtained from Sigma-Aldrich-Fluka (St. Louis, MO). Benzoyl adenosine, benzoyl cytidine, and phenylacetyl guanosine were obtained from Carbosynth Limited (Berkshire, UK).

Synthesis of PMO, PMOplus, PPMO, and PMO-X containing further linkage modifications as described herein was done using methods known in the art and described in pending U.S. patent application Ser. Nos. 12/271,036 and 12/271,040 and PCT Publication No. WO 2009/064471, which is hereby incorporated by reference in its entirety.

PMO with a 3' trityl modification are synthesized essentially as described in PCT Publication No. WO 2009/064471 with the exception that the detritylation step is omitted.

D. Cell-Penetrating Peptides

Figure 1C:
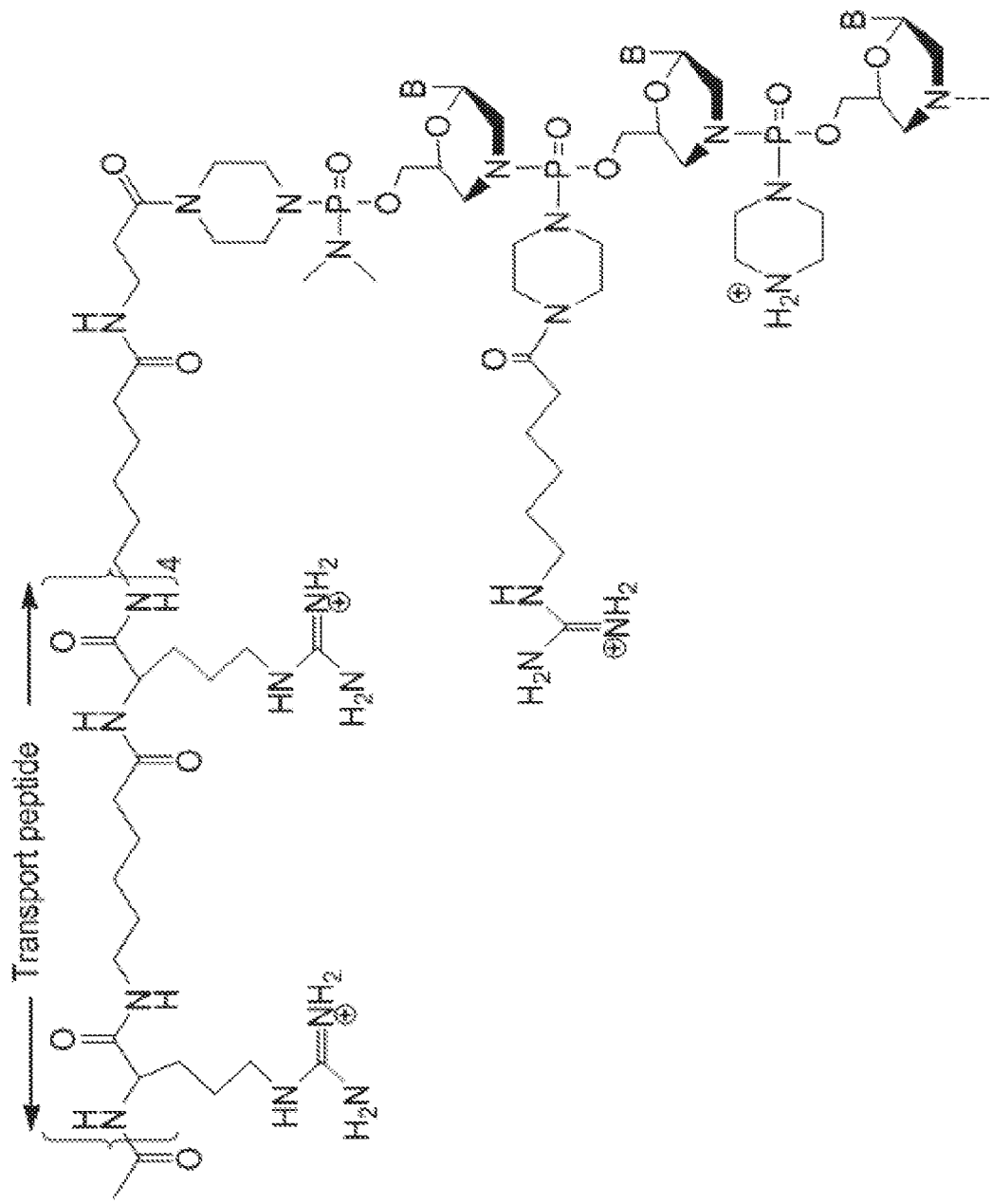
Figure 1E:
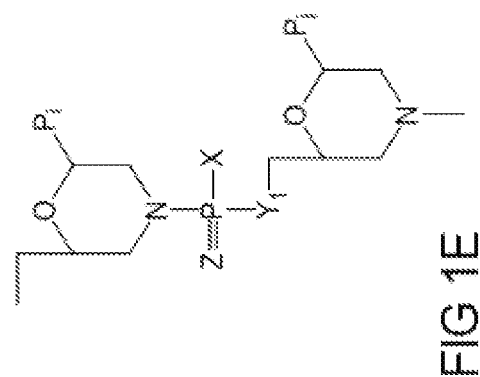
FIGS. 1D, 1E, 1F and 1G illustrate a repeating subunit segment of exemplary morpholino oligomers, designated D through G.
Figure 1G:
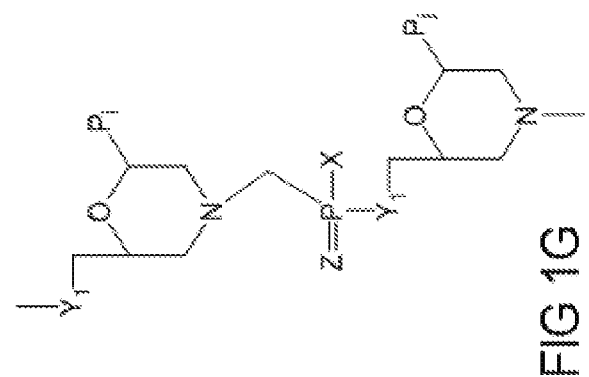
Figure 1D:
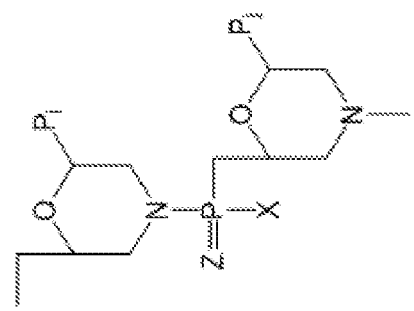
Figure 1F:
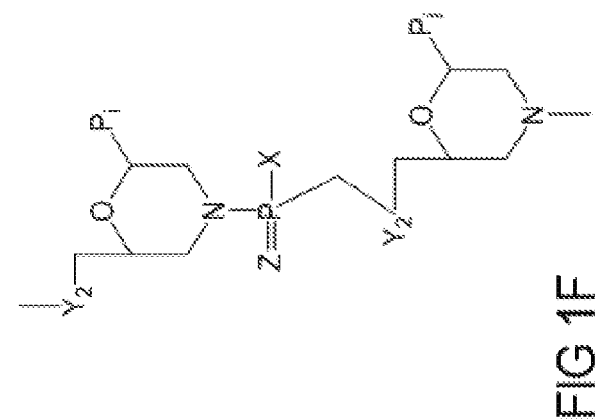

The antisense oligomer compounds of the disclosure may be conjugated to a peptide, also referred to herein as a cell penetrating peptide (CPP). In certain preferred embodiments, the peptide is an arginine-rich peptide transport moiety effective to enhance transport of the compound into cells. The transport moiety is preferably attached to a terminus of the oligomer, for example to the 3' terminal end of the oligomer. Exemplary transport moieties are shown in FIGS. 1B and 1C. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter. In another embodiment, the cell-penetrating peptide may be Penetratin or the Tat peptide. These peptides are well known in the art and are disclosed, for example, in US Publication No. 2010-0016215 A1, which is hereby incorporated by reference in its entirety. One approach to conjugation of peptides to antisense oligomers of the disclosure can be found in PCT publication WO2012/150960, which is hereby incorporated by reference in its entirety. Some embodiments of a peptide conjugated oligomer of the present disclosure utilize glycine as the linker between the CPP and the antisense oligomer. For example, a peptide conjugated PMO of the disclosure consists of $R_6$-G-PMO.

The transport moieties as described above have been shown to greatly enhance cell entry of attached oligomers, relative to uptake of the oligomer in the absence of the attached transport moiety. Uptake is preferably enhanced at least ten fold, and more preferably twenty fold, relative to the unconjugated compound.

The use of arginine-rich peptide transporters (i.e., cell-penetrating peptides) are particularly useful in practicing the present disclosure. Certain peptide transporters have been shown to be highly effective at delivery of antisense compounds into primary cells including muscle cells (Marshall, Oda et al. 2007; Jearawiriyapaisarn, Moultoneta. 2008; Wu, Moulton eta. 2008, which are hereby incorporated by reference in their entirety). Furthermore, compared to other known peptide transporters such as Penetratin and the Tat peptide, the peptide transporters described herein, when conjugated to an antisense PMO, demonstrate an enhanced ability to alter splicing of several gene transcripts (Marshall, Oda et al. 2007, which is hereby incorporated by reference in its entirety).

Exemplary peptide transporters, such as arginine-rich peptides, excluding linkers, are given below in Table 3.

TABLE 3

Exemplary peptide transporters

| NAME (DESIGNATION) | SEQUENCE | SEQ ID NO[A] |
|---|---|---|
| rTAT | RRRQRRKKR | 9 |
| Tat | RKKRRQRRR | 10 |
| $R_9F_2$ | RRRRRRRRFF | 11 |
| $R_5F_2R_4$ | RRRRRFFRRRR | 12 |
| $R_4$ | RRRR | 13 |
| $R_5$ | RRRRR | 14 |
| $R_6$ | RRRRRR | 15 |
| $R_7$ | RRRRRRR | 16 |
| $R_8$ | RRRRRRRR | 17 |
| $R_9$ | RRRRRRRRR | 18 |
| $(RX)_8$ | RAhxRAhxRAhxRAhxRAhxRAhxRAhxRAhx | 19 |
| $(RAhxR)_4$; (P007) | RAhxRRAhxRRAhxRRAhxR | 20 |
| $(RAhxR)_5$; (CP04057) | RAhxRRAhxRRAhxRRAhxRRAhxR | 21 |
| $(RAhxRRBR)_2$; (CP06062) | RAhxRRBRRAhxRRBR | 22 |
| $(RAR)_4F_2$ | RARRARRARRARFF | 23 |
| $(RGR)_4F_2$ | RGRRGRRGRRGRFF | 24 |

[A]Sequences assigned to SEQ ID NOS do not include the linkage portion (e.g., C (cys), G (gly), P (pro), Ahx, B, AhxB where Ahx and B refer to 6-aminohexanoic acid and beta-alanine, respectively).

In various embodiments, G (as recited in formulas I, IV, and V) is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, and —C(O)CH$_2$NH—CPP, or G is of the formula:

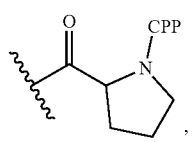

wherein the CPP is attached to the linker moiety by an amide bond at the CPP carboxy terminus. In some embodiments, the CPP is selected from SEQ ID NOS: 9-24.

In some embodiments, G (as recited in formulas I, IV, and V) is of the formula:

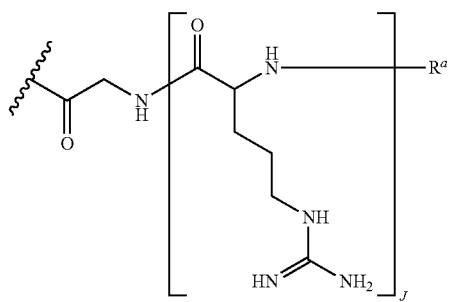

wherein $R^a$ is selected from H, acetyl, benzoyl, and stearoyl, and J is an integer from 4 to 9. In certain embodiments J is 6.

In various embodiments, the CPP (as recited in formulas I, IV, and V) is of the formula:

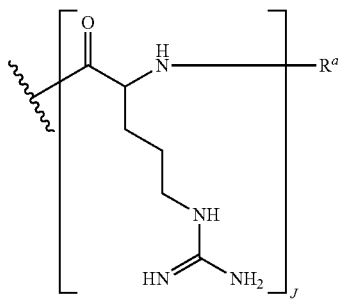

wherein $R^a$ is selected from H, acetyl, benzoyl, and stearoyl, and J is an integer from 4 to 9. In certain embodiments, the CPP is SEQ ID NO: 15. In various embodiments, J is 6. In some embodiments $R_a$ is selected from H and acetyl. For example, in some embodiments, $R_a$ is H. In certain embodiments, $R_a$ is acetyl.

IV. Formulations

The compounds of the disclosure may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, which are hereby incorporated by reference in their entirety.

The antisense compounds of the disclosure encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the disclosure are prepared as SATE [(S-acetyl-2-thioethyl) phosphate] derivatives according to the methods disclosed in PCT Publication No. WO 1993/24510 to Gosselin et al., published Dec. 9, 1993 or in PCT Publication No. WO 1994/26764 and U.S. Pat. No. 5,770,713 to Imbach et al., which are hereby incorporated by reference in their entirety The term "pharmaceutically acceptable salts" refers to physiologically and pharmaceutically acceptable salts of the compounds of the disclosure: i.e., salts that retain the desired biological activity of the parent compound and do not impart undesired toxicological effects thereto. For oligomers, examples of pharmaceutically acceptable salts and their uses are further described in U.S. Pat. No. 6,287,860, which is hereby incorporated by reference in its entirety.

The present disclosure also includes pharmaceutical compositions and formulations which include the antisense compounds of the disclosure. In various embodiments, the pharmaceutical composition comprises antisense oligomer compounds of 12 to 40 subunits and a pharmaceutically acceptable carrier, where the compound comprises at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an exon/intron junction of human type VII collagen pre-mRNA, wherein the contiguous nucleotides include the exon/intron junction, and wherein said exon/intron junction comprises the splice junction of exon 80/intron 80. In further embodiments, the pharmaceutical compositions and formulations comprise a compound of formula (I). In various embodiments, the pharmaceutical compositions and formulations further comprise an arginine-rich peptide sequence conjugated to the 3' terminal end of the antisense oligomer, where the arginine-rich peptide sequence comprises a sequence selected from SEQ ID NOS: 9-24 as provided in Table 3. The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present disclosure include, but are not limited to, solutions, emulsions, foams and liposome-containing formulations. The pharmaceutical compositions and formulations of the present disclosure may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is hereby incorporated by reference in its entirety.

Formulations of the present disclosure include liposomal formulations. As used in the present disclosure, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic oligomers, such as a polyethylene glycol (PEG) moiety. Liposomes and their uses are further described in U.S. Pat. No. 6,287,860, which is hereby incorporated by reference in its entirety.

The pharmaceutical formulations and compositions of the present disclosure may also include surfactants. The use of surfactants in drug products, formulations and in emulsions is well known in the art. Surfactants and their uses are further described in U.S. Pat. No. 6,287,860, which is hereby incorporated by reference in its entirety.

In some embodiments, the present disclosure employs various penetration enhancers to effect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is hereby incorporated by reference in its entirety.

One of skill in the art will recognize that formulations are routinely designed according to their intended use, i.e. route of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is hereby incorporated by reference in its entirety. Topical formulations are described in detail in U.S. patent application Ser. No. 09/315,298 filed on May 20, 1999 and Mourich et al., 2009, J. Invest. Dermatol., 129(8):1945-53, which are hereby incorporated by reference in their entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860, which is hereby incorporated by reference in its entirety. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860, which is hereby incorporated by reference in its entirety. Oral formulations for oligomers and their preparation are described in detail in U.S. patent application Ser. No. 09/108,673 (filed Jul. 1, 1998), Ser. No. 09/315,298 (filed May 20, 1999) and Ser. No. 10/071,822 (filed Feb. 8, 2002), which are hereby incorporated by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

In another related embodiment, compositions of the disclosure may contain one or more antisense compounds, particularly oligomers, targeted to a first nucleic acid and one or more additional antisense compounds targeted to a second nucleic acid target. Alternatively, compositions of the disclosure may contain two or more antisense compounds targeted to different regions of the same nucleic acid target. Numerous examples of antisense compounds are known in the art. Two or more combined compounds may be used together or sequentially.

V. Methods of Use

Various aspects relate to methods of increasing functional human type VII collagen expression in a subject. In further aspects, methods of treating or preventing dystrophic epidermolysis bullosa (DEB) and related disorders in a subject, including such as where a subject may be a healthy subject or a subject afflicted with a disease, disorder, or condition associated with blistering of the skin. In further aspects, methods of increasing functional human type VII collagen expression are provided. In further aspects, methods of increasing translation of functional human type VII collagen are provided. In further aspects, methods of increasing the accumulation of functional human type VII collagen in anchoring fibrils and/or increasing the accumulation of anchoring fibrils are provided.

In further aspects, methods of inhibiting the expression of genomic exon 80 of the human type VII collagen gene are provided. In further aspects, methods of inhibiting the splicing of human type VII collagen pre-mRNA sequences comprising a splice junction are provided. In further aspects, methods of inhibiting the expression of exon 80 in a mature mRNA human type VII collagen transcript are provided. In further aspects, methods of modulating such as, for example, increasing the expression of functional human type VII collagen protein are provided. In further aspects, methods of inhibiting the progression of dystrophic epidermolysis bullosa are provided.

In further aspects and embodiments, methods of treating an individual afflicted with or at risk for developing dystrophic epidermolysis bullosa and related disorders are provided, comprising administering an effective amount of an antisense oligomer of the disclosure to the subject. In various embodiments, the antisense oligomer comprises a nucleotide sequence of sufficient length and complementarity to specifically hybridize to a splice junction region within the pre-mRNA transcript of the human type VII collagen gene, where binding of the antisense oligomer to the region decreases the level of exon 80 containing human type VII collagen mRNA in a cell and/or tissue of the subject. In further embodiments, the antisense oligomer comprises formula (I). In further embodiments, the antisense oligomer comprises a targeting sequence selected from SEQ ID NOS: 2, 3, 4 or 6, is selected from SEQ ID NOS: 2, 3, 4 or 6, is a fragment of at least 12 contiguous nucleotides of a sequence selected from SEQ ID NOS: 2, 3, 4 or 6, or is a variant having at least 90% sequence identity to a sequence selected from SEQ ID NOS: 2, 3, 4 or 6, where X is selected from uracil (U) or thymine (T). In further embodiments, binding of an antisense oligomer to a splice junction region within the pre-mRNA transcript of the human type VII collagen gene increases translation of functional human type VII collagen mRNA. In various embodiments, binding of an antisense oligomer to a splice junction region within the pre-mRNA transcript of the human type VII collagen gene increases expression of functional human type VII collagen. Exemplary antisense targeting sequences are shown in Table 2.

Also included are antisense oligomers for use in the preparation of a medicament for the treatment of dystrophic epidermolysis bullosa and related disorders, comprising a nucleotide sequence of sufficient length and complementarity to specifically hybridize to a region within the pre-mRNA transcript of the human type VII collagen gene, where binding of the antisense oligomer to the target region decreases the level of exon 80 human type VII collagen mRNA. In further embodiments, binding of an antisense oligomer to a splice junction region within the pre-mRNA transcript of the human type VII collagen gene increases translation of functional human type VII collagen mRNA. In various embodiments, binding of an antisense oligomer to a splice junction region within the pre-mRNA transcript of the human type VII collagen gene increases expression of functional human type VII collagen.

In various aspects and embodiments, methods of treating dystrophic epidermolysis bullosa and related disorders, and medicaments for the treatment of dystrophic epidermolysis bullosa and related disorders are provided comprising administering an antisense oligomer where the antisense oligomer comprises 12 to 40 subunits, optionally having at least one subunit that is a nucleotide analog having (i) a modified internucleoside linkage, (ii) a modified sugar moiety, or (iii) a combination of the foregoing; and a targeting sequence complementary to 12 or more contiguous nucleotides in a target region spanning an exon/intron splice junction of human type VII collagen pre mRNA. In various embodiments, the contiguous nucleotides include the exon/intron splice junction. In further embodiments, the splice junction comprises exon 80/intron 80 (e.g., SEQ ID NO: 1). These may include 12 to 40 subunits that specifically hybridize to a target region spanning an exon/intron splice junction of human type VII collagen pre-mRNA. The splice junction comprises the splice junction at the intersect of exon 80/intron 80. In embodiments, the splice junction of exon 80/intron 80 comprises the splice junction of SEQ ID NO: 1.

These additional aspects and embodiments include antisense oligomers having a nucleotide analog subunit comprising a modified sugar moiety. In various embodiments, the modified sugar moiety is selected from a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' O-methoxyethyl subunit, a 2'-fluoro subunit, a 2'-O-[2-(N-methylcarbamoyl)ethyl] subunit, and a morpholino subunit.

These additional aspects and embodiments include antisense oligomers having a nucleotide analog subunit comprising a modified internucleoside linkage. In various embodiments, the modified internucleoside linkage is selected from a phosphorothioate internucleoside linkage, a phosphoramidate internucleoside linkage, a phosphorodiamidate internucleoside linkage. In further embodiments, the phosphorodiamidate internucleoside linkage comprises a phosphorous atom that is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

These additional aspects and embodiments include antisense oligomers having a nucleotide analog subunit comprising at least one combination of a modified sugar moiety and a modified internucleoside linkage.

Various aspects relate to methods of decreasing expression of exon 80 containing human type VII collagen mRNA transcript in a cell, tissue, and/or subject, using the antisense oligomers as described herein. In some instances, human type VII collagen mRNA transcript containing exon 80 or dysfunctional human type VII collagen protein is decreased or reduced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject having dystrophic epidermolysis bullosa or a related disorder), a control composition without the antisense oligomer, the absence of treatment, and/or an earlier timepoint. Also included are methods of decreasing the expression of exon 80 containing mRNA transcript or dysfunctional human type VII collagen protein relative to the levels of a control, for example, a subject having dystrophic epidermolysis bullosa or a related disorder.

Various aspects relate to methods of increasing the expression of functional human type VII collagen protein, increasing the accumulation of functional human type VII collagen in anchoring fibrils, and/or increasing the accumulation of anchoring fibrils in a cell, tissue, and/or subject, using the antisense oligomers as described herein. In some instances, functional human type VII collagen, functional human type VII collagen anchoring fibrils or anchoring fibrils is increased or enhanced by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject having dystrophic epidermolysis bullosa or a related disorder), a control composition without the antisense oligomer, the absence of treatment, and/or an earlier time-point. Also included are methods of increasing the expression of functional human type VII collagen protein, increasing the accumulation of functional human type VII collagen in anchoring fibrils, and/or increasing the accumulation of anchoring fibrils relative to the levels of a control, for example, a subject having dystrophic epidermolysis bullosa or a related disorder.

Various aspects relate to methods of decreasing expression of a dysfunctional/inactive human type VII collagen protein in a cell, tissue, and/or subject, as described herein. In certain instances, the level of dysfunctional/inactive human type VII collagen protein is decreased by about or at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject (for example, a subject having epidermolysis bullosa or a related disorder), a control composition without the antisense oligomer, the absence of treatment, and/or an earlier time-point. Also included are methods of decreasing the expression of dysfunctional/inactive human type VII collagen protein relative to the levels of an affected control, for example, a subject having dystrophic epidermolysis bullosa or a related disorder.

Various aspects relate to methods of inhibiting the progression of dystrophic epidermolysis bullosa and related disorders in a subject using the antisense oligomers as described herein.

Various aspects relate to methods of reducing, or improving, as appropriate, one or more symptoms of dystrophic epidermolysis bullosa and related disorders in a subject in need thereof. Particular examples include symptoms of progressive skin fragility such as blistering of the skin and mucosae after mild trauma, skin cancer, metastatic squamous cell carcinoma and loss of dermo-epidermal adhesion.

Antisense oligomers herein may be administered to subjects to treat (prophylactically or therapeutically) dystrophic epidermolysis bullosa and related disorders. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced. Direct CNS delivery may be employed, for instance, intracerebral ventribular or intrathecal administration may be used as routes of administration.

In particular embodiments, the antisense oligomer(s) are administered to the subject by intravenous (IV) or subcutaneous (SC), i.e., they are administered or delivered intravenously into a vein or subcutaneously into the fat layer between the skin and muscle. Non-limiting examples of intravenous injection sites include a vein of the arm, hand, leg, or foot. Non-limiting examples of subcutaneous injections sites include the abdomen, thigh, lower back or upper arm. In exemplary embodiments, a PMO, PMO-X, or PPMO forms of the antisense oligomer is administered by IV or SC. In other embodiments, the antisense oligomer(s) are administered to the subject by intramuscular (IM), e.g., they are administered or delivered intramuscularly into the deltoid muscle of the arm, the vastus lateralis muscle of the leg, the ventrogluteal muscles of the hips, or dorsogluteal muscles of the buttocks.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, which are hereby incorporated by reference in their entirety.

The antisense oligomers described herein may also be delivered via an implantable device. Design of such a device is an art-recognized process, with, e.g., synthetic implant design described in, e.g., U.S. Pat. No. 6,969,400, which are hereby incorporated by reference in their entirety.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49 (2000), which is hereby incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The antisense oligomers of the present disclosure may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure where hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in PCT Publication No. WO 1993/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules. Each such reference is hereby incorporated by reference in their entirety.

In one embodiment, the antisense oligomer is administered to a mammalian subject, e.g., human or domestic animal, exhibiting the symptoms of dystrophic epidermolysis bullosa and related disorders, in a suitable pharmaceutical carrier. In one aspect of the method, the subject is a human subject, e.g., a patient diagnosed as having dystrophic epidermolysis bullosa and related disorders. In one preferred embodiment, the antisense oligomer is contained in a pharmaceutically acceptable carrier, and is delivered orally. In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mRNA which does not comprise human type VII collagen exon 80 in relation to a reference exon 80-containing human type VII collagen mRNA as determined by standard techniques such as RT-PCR, Northern blotting, ELISA or Western blotting.

In some embodiments, the antisense oligomer is actively taken up by mammalian cells. In further embodiments, the antisense oligomer may be conjugated to a transport moiety (e.g., transport peptide or CPP) as described herein to facilitate such uptake. In various embodiments, the transport moiety may comprise an arginine-rich peptide transporter comprising a sequence, excluding linkers, as provided in Table 3.

VI. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 g to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, where the oligomer is administered in maintenance doses, ranging from 1-1000 mg oligomer per 70 kg of body weight for oral administration, or 0.5 mg to 1000 mg oligomer per 70 kg of body weight for i.v. administration, once or more daily, to once every 20 years.

While the present disclosure has been described with specificity in accordance with certain of its embodiments, the following examples serve only to illustrate the disclosure and are not intended to limit the same. Each of the references, patents, patent applications, GenBank accession numbers, and the like recited in the present application are hereby incorporated by reference in its entirety.

VII. Examples

Example 1

Design and Manufacture of Antisense Oligomers

Figure 2A:
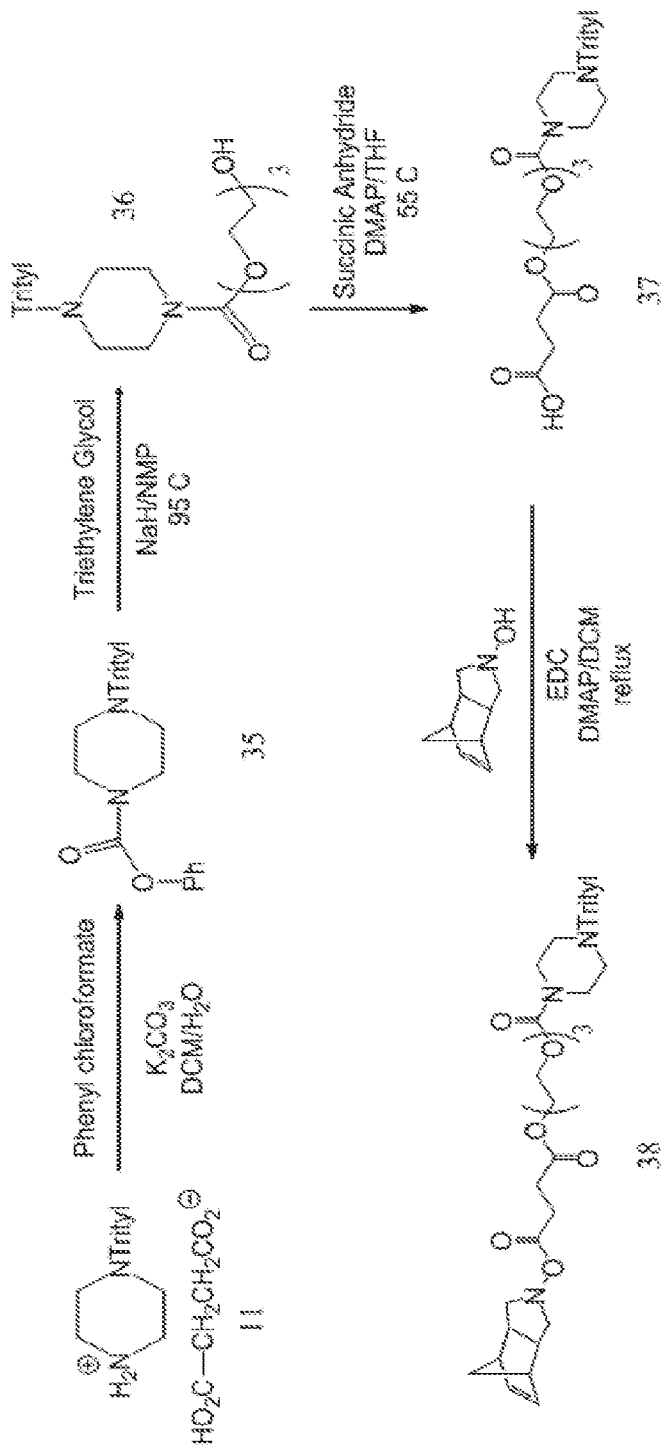
FIG. 2A illustrates preparation of trityl piperazine phenyl carbamate.

Antisense oligomers of the disclosure were designed to bind to a target region spanning an exon 80/intron 80 splice junction of a human type VII collagen pre-mRNA transcript and prepared using the following protocol:

Preparation of trityl piperazine phenyl carbamate 35 (FIG. 2A): To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile.

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbomene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts.

Introduction of the activated "Tail" onto the anchor-loaded resin was performed in dimethyl imidazolidinone (DMI) by the procedure used for incorporation of the subunits during solid phase synthesis.

Preparation of the Solid Support for Synthesis of morpholino-based oligomers: This procedure was performed in a silanized, jacketed peptide vessel (ChemGlass, NJ, USA) with a coarse porosity (40-60 µm) glass frit, overhead stirrer, and 3-way Teflon stopcock to allow N2 to bubble up through the frit or a vacuum extraction.

The resin treatment/wash steps in the following procedure consist of two basic operations: resin fluidization or stirrer bed reactor and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

Figure 2B:
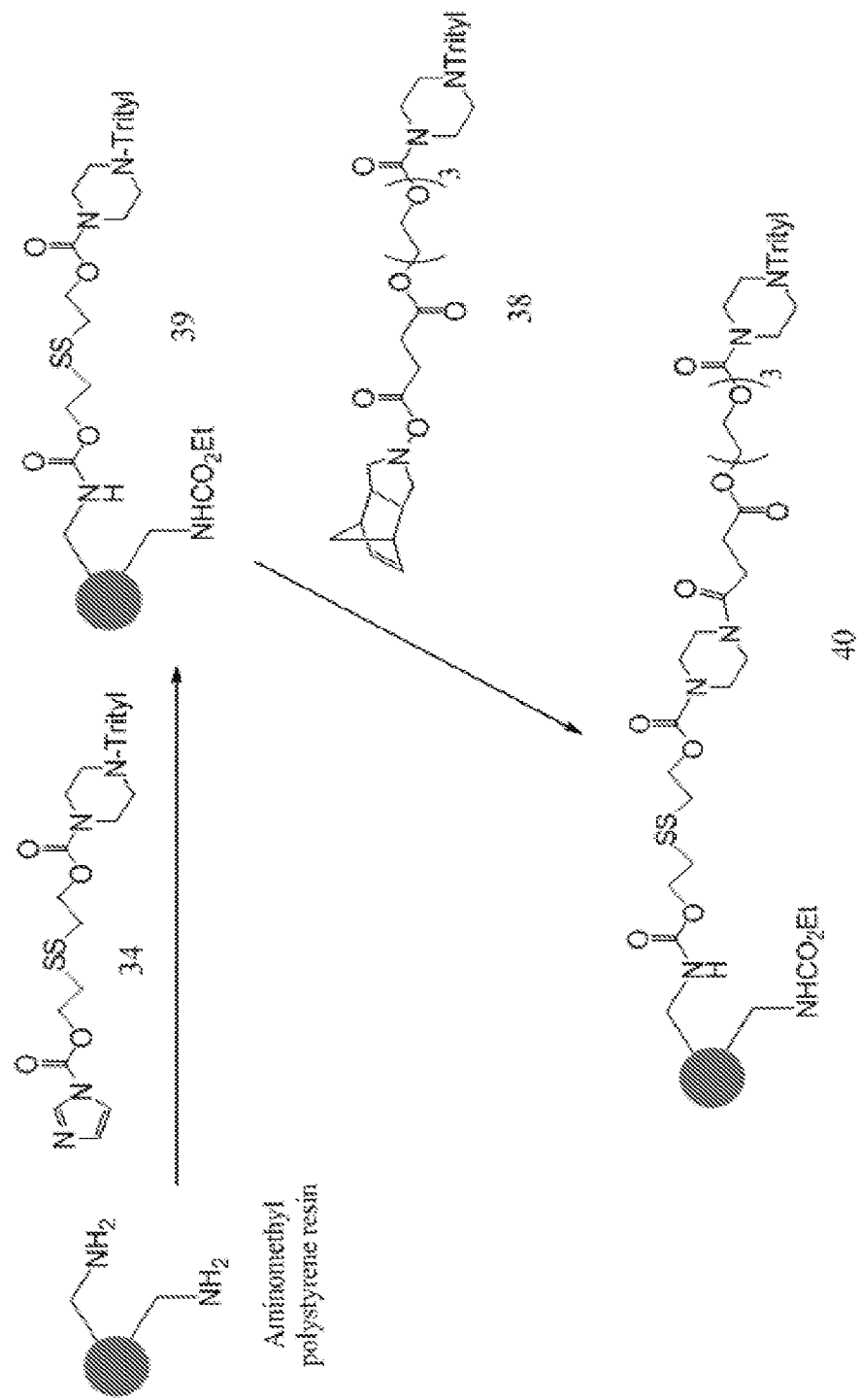
FIG. 2B illustrates preparation of a resin/reagent mixture.

To aminomethylpolystyrene resin (100-200 mesh; ~1.0 mmol/g load based on nitrogen substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was treated with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 (see FIG. 2B) was dried under a N2 stream for 1-3 hr and then under vacuum to constant weight (2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient (ε: 41 µmol-1 cm-1) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into solid support. The anchor loaded resin was first deprotected under acidic condition and the resulting material neutralized before coupling. For the coupling step, a solution of 38 (0.2 M) in DMI containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Solid Phase Synthesis: morpholino-based oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:
Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated morpholino subunit of the desired base and linkage type and 0.4 M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

TABLE 4

| Step | Volume | Delivery | Hold time |
| --- | --- | --- | --- |
| Detritylation | 1.5 mL | Manifold | 15 sec. |
| Detritylation | 1.5 mL | Manifold | 15 sec. |

TABLE 4-continued

| Step | Volume | Delivery | Hold time |
|---|---|---|---|
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| Detritylation | 1.5 mL | Manifold | 15 sec. |
| DCM | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| Neutralization | 1.5 mL | Manifold | 30 sec. |
| DCM | 1.5 mL | Manifold | 30 sec. |
| Coupling | 350-500 uL | Syringe | 40 min. |
| DCM | 1.5 mL | Manifold | 30 sec. |
| Neutralization | 1.5 mL | Manifold | 30 sec. |
| Neutralization | 1.5 mL | Manifold | 30 sec. |
| DCM | 1.5 mL | Manifold | 30 sec. |
| DCM | 1.5 mL | Manifold | 30 sec. |
| DCM | 1.5 mL | Manifold | 30 sec. |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and protecting groups: After methoxytritylation, the resin was washed 8 times with 2 mL 1-methyl-2-pyrrolidinone. One mL of a cleavage solution comprising 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 μL of cleavage solution. To the solution was added 4.0 mL conc. Aqueous ammonia (stored at −20° C.), the vial capped tightly (with Teflon lined screw cap), and the mixture swirled to mix the solution. The vial was placed in a 45° C. oven for 16-24 hr to effect cleavage of base and protecting groups.

Crude product purification: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of morpholino-based oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

SPE column packing and conditioning: Amberchrome CG-300M (Rohm and Haas; Philadelphia, PA) (3 mL) is packed into 20 mL fritted columns (BioRad Econo-Pac Chromatography Columns (732-1011)) and the resin rinsed with 3 mL of the following: 0.28% NH4OH/80% acetonitrile; 0.5M NaOH/20% ethanol; water; 50 mM H3PO4/80% acetonitrile; water; 0.5 NaOH/20% ethanol; water; 0.28% NH4OH.

SPE purification: The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia.

Product isolation: The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of morpholino-based oligomers by MALDI: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

Example 2

In Vitro Studies of Antisense Oligomers

In vitro experiments were performed to investigate the ability of antisense oligomers designed and prepared as described above to decrease the expression of exon 80 containing human type VII collagen pre-mRNA and increase the expression of functional human type VII collagen. Both normal human dermal adult fibroblast cells (HDFa cells; cat #C-013-5C, Cascade Biologics (Life Technologies; Grand Island, NY) and normal human epidermal adult keratinocytes (HEKa cells; cat #C-005-5C, Cascade Biologics (Life Technologies; Grand Island, NY) were used in the experiments as noted. HDFa cells or HEKa cells were nucleofected with antisense oligomers at 10, 3, 1 and 0.3 μM in SG or P3 nucleofector solution, respectively, and incubated overnight at 37° C. with 5% CO$_2$. Total RNA was isolated from the cells and RT-PCR was performed using primers DEB 79 FWD Set 2 (5' TAC CAG GAG AGC GTG GTA T 3'; SEQ ID NO: 25) and DEB 83 REV Set 2 (5' GTC CTG GAG GTC CTG TCT 3'; SEQ ID NO: 26). Amplified samples were analyzed using the LabChip Caliper to determine percent exon 80 skipping. EC50 values were determined using non-linear regression analysis in GraphPad Prism. EC50 values represent the concentration at which the test PMO induces 50% exon skipping.

A first series of antisense oligomers designed to target exon 80 of the human type VII collagen gene (COL7A1), including the exon 80/intron 80 junction (splice donor site) was synthesized and used to treat normal human dermal adult fibroblasts cells (HDFa) and normal human epidermal adult keratinocytes (HEKa) as described above. The antisense oligomers of the disclosure included Col7a-1, Col7a-2, Col7a-3, and Col7a-4, and were compared to compounds Col7a-5, Col7a-6, and Col7a-7, all of which are described in Table 5 below.

Figure 3:
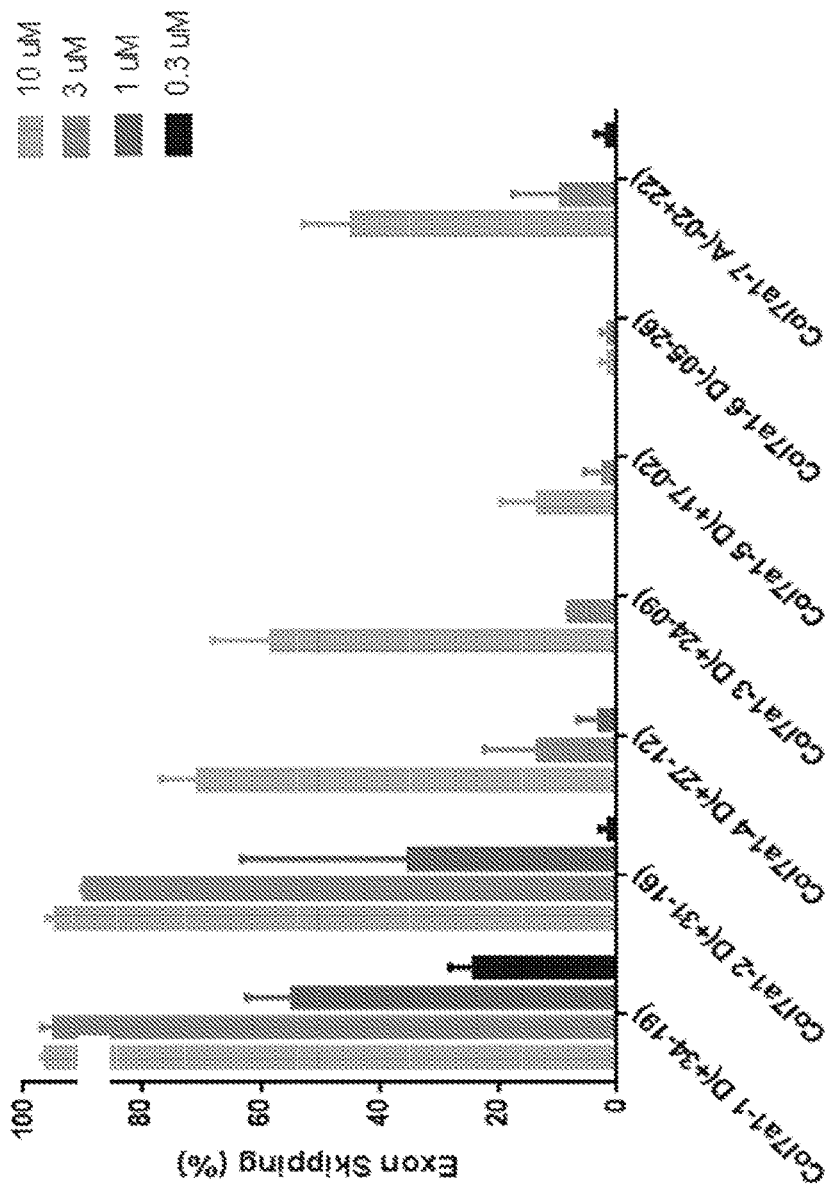
FIG. 3 illustrates a first series of human type VII collagen antisense oligomers activity in human adult dermal fibroblasts (HDFa).

As shown in FIG. 3(HDFa) and FIG. 4(HEKa), antisense oligomers according to the disclosure (Col7a1-1, Col7a1-2, Col7a1-3, and Col7a1-4) were particularly effective at causing exon 80 skipping and showed improved activity compared to an antisense oligomer comprising a sequence known in the prior art (Col7a1-7(−02+22); SEQ ID NO:8; International Pub. No.: WO 2013/053819), an antisense oligomer comprising a targeting sequence that does not hybridize to the exon 80/intron 80junction (Col7a-6 D(−05−26) targeting sequence SEQ ID NO:5),and Col7a1-5 D(+17−02) (targeting sequence SEQ ID NO: 7).

TABLE 5

Exon 80 Antisense Oligomers

| Compound Name | Target Area | Sequence 5' to 3'* | SEQ ID NO: | 5' End | 3' End |
|---|---|---|---|---|---|
| Col7a1-1 | D(+34-19) | AAGGTTCTTGGGTACTCACCAC | 27 | EG3 | H |
| Col7a1-2 | D(+31-16) | GTTCTTGGGTACTCACCACTGG | 28 | EG3 | H |
| Col7a1-3 | D(+24-09) | GGTACTCACCACTGGGCCAGIG | 29 | EG3 | H |

TABLE 5-continued

Exon 80 Antisense Oligomers

| Compound Name | Target Area | Sequence 5' to 3'* | SEQ ID NO: | 5' End | 3' End |
|---|---|---|---|---|---|
| Col7a1-4 | D(+27-12) | TTGGGTACTCACCACTGGGCCA | 30 | EG3 | H |
| Col7a1-7 | A(-02-22) | GGCCTCTTGGACCCTGCAGACCCT | 31 | EG3 | H |
| Col7a1-6 | D(-05-26) | ACAGGTGAAGGTTCTTGGGTAC | 32 | EG3 | H |
| Col7a1-5 | D(+17-02) | ACCACTGIGCCAGIGIGICCTC | 33 | EG3 | H |

*wherein thymine (T) bases may be uracil (U) bases; wherein "I" is inosine

EC50 values of compounds Col7a1-1, Col7a1-2, Col7a1-3, and Col7a1-4 as compared to EC50 values for Col7a1-7 are shown below in Table 6.

TABLE 6

EC50 Values

| Compound Name | Target Area | Sequence 5' to 3'* | SEQ ID NO: | 5' End | 3' End | HDFa EC50 | HEKa EC50 |
|---|---|---|---|---|---|---|---|
| Col7a1-1 | D(+34-19) | AAGGTTCTTGGGTACTCACCAC | 27 | EG3 | H | 0.14 | 0.05 |
| Col7a1-2 | D(+31-16) | GTTCTTGGGTACTCACCACTGG | 28 | EG3 | H | 0.46 | 0.11 |
| Col7a1-3 | D(+24-09) | GGTACTCACCACTGGGCCAGIG | 29 | EG3 | H | 2.75 | 0.66 |
| Col7a1-4 | D(+27-12) | TTGGGTACTCACCACTGGGCCA | 30 | EG3 | H | 1.99 | 0.73 |
| Col7a1-7 | A(-02+22) | GGCCTCTTGGACCCTGCAGACCCT | 31 | EG3 | H | 3.07 | 0.86 |

*wherein thymine (T) bases may be uracil (U) bases; wherein "I" is inosine

The sequences disclosed herein are further listed in Table 7 below.

TABLE 7

Sequence Listing

| Name | Sequence (5'-3')* | SEQ ID NO |
|---|---|---|
| Exon 80/Intron 80 | GGTCTGCAGGGTCCAAGAGGCCCCCCTGGCCCAGTG/GTGAGTACCCAAGAACCTTCACCTGTC | 1 |
| Col7a1-4 D(+27-12) | XXGGGXACXCACCACXGGGCCA | 2 |
| Col7a1-2 D(+31-16) | GXXCXXGGGXACXCACCACXGG | 3 |
| Col7a1-1 D(+34-19) | AAGGXXCXXGGGXACXCACCAC | 4 |
| Col7a1-6 D(-05-26) | ACAGGXGAAGGXXCXXGGGXAC | 5 |
| Col7a1-3 D(+24-09) | GGXACXCACCACXGGGCCAGIG | 6 |
| Col7a1-5 D(+17-02) | ACCACXGIGCCAGIGIGICCXC | 7 |
| Col7a1-7 A(-02+22) | GGCCXCXXGGACCCXGCAGACCCX | 8 |
| rTAT | RRRQRRKKR | 9 |
| Tat | RKKRRQRRR | 10 |

TABLE 7-continued

Sequence Listing

| Name | Sequence (5'-3')* | SEQ ID NO |
|---|---|---|
| $R_9F_2$ | RRRRRRRRRFF | 11 |
| $R_5F_2R_4$ | RRRRRFFRRRR | 12 |
| $R_4$ | RRRR | 13 |
| $R_5$ | RRRRR | 14 |
| $R_6$ | RRRRRR | 15 |
| $R_7$ | RRRRRRR | 16 |
| $R_8$ | RRRRRRRR | 17 |
| $R_9$ | RRRRRRRRR | 18 |
| $(RAhx)_8$ | RAhx RAhx RAhx RAhx RAhx RAhx RAhx RAhx | 19 |
| $(RAhxR)_4$; (P007) | RAhxRRAhxRRAhxRRAhxR | 20 |
| $(RAhxR)_5$; (CP04057) | RAhxRRAhxRRAhxRRAhxRRAhxR | 21 |
| $(RAhxRRBR)_2$; (CP06062) | RAhxRRBRRAhxRRBR | 22 |
| $(RAR)_4F_2$ | RARRARRARRARFF | 23 |
| $(RGR)_4F_2$ | RGRRGRRGRRGRFF | 24 |
| DEB 79 FWD Set 2 | TAC CAG GAG AGC GTG GTA T | 25 |
| DEB 83 REV Set 2 | GTC CTG GAG GTC CTG TCT | 26 |
| Col7a1-1 D(+34-19) | AAGGTTCTTGGGTACTCACCAC | 27 |
| Col7a1-2 D(+31-16) | GTTCTTGGGTACTCACCACTGG | 28 |
| Col7a1-3 D(+24-09) | GGTACTCACCACTGGGCCAGIG | 29 |
| Col7a1-4 D(+27-12) | TTGGGTACTCACCACTGGGCCA | 30 |
| Col7a1-7 A(-02+22) | GGCCTCTTGGACCCTGCAGACCCT | 31 |
| Col7a1-6 D(-05-26) | ACAGGTGAAGGTTCTTGGGTAC | 32 |
| Col7a1-5 D(+17-02) | ACCACTGIGCCAGIGIGICCTC | 33 |
| Exon 80/ Intron 80 Target Sequence | GGXCXGCAGGGXCCAAGAGGCCCCCCXGGC CCAGXG/GXGAGXACCCAAGAACCXXCACCX GXC | 34 |
| DEB 79 FWD Set 2 Primer | XAC CAG GAG AGC GXG GXA X | 35 |
| DEB 83 REV Set 2 Primer | GXC CXG GAG GXC CXG XCX | 36 |

*wherein X is selected from thymine and uracil, and thymine (T) bases may be uracil (U) bases; wherein "I" is inosine, wherein Ahx is 6-aminohexanoic acid, and wherein B is beta-alanine

What is claimed is:

1. An antisense oligomer compound of 12 to 40 subunits, comprising:
   at least one subunit that is a nucleotide analog having (i) a modified internucleoside linkage, (ii) a modified sugar moiety, or (iii) a combination of the foregoing; and
   a targeting sequence complementary to 12 or more contiguous nucleotides in a target region spanning an exon/intron junction of human type VII collagen pre-mRNA, wherein the contiguous nucleotides include the exon/intron junction, and wherein said exon/intron junction comprises the splice junction of exon 80/intron 80, wherein the targeting sequence is selected from SEQ ID NOS: 27, 28, 29, and 30.

2. The antisense oligomer compound of claim 1, wherein the modified internucleoside linkage is selected from a phosphorothioate internucleoside linkage, a phosphoramidate internucleoside linkage, a phosphorodiamidate internucleoside linkage, or a phosphorodiamidate wherein the phosphorous atom is covalently bonded to a (1,4-piperazin)-1-yl moiety, a substituted (1,4-piperazin)-1-yl moiety, a 4-aminopiperidin-1-yl moiety, or a substituted 4-aminopiperidin-1-yl moiety.

3. The antisense oligomer compound of claim 1, wherein the modified sugar moiety includes at least one of a peptide nucleic acid (PNA) subunit, a locked nucleic acid (LNA) subunit, a 2'O,4'C-ethylene-bridged nucleic acid (ENA) subunit, a tricyclo-DNA (tc-DNA) subunit, a 2' O-methyl subunit, a 2' 0-methoxyethyl subunit, a 2'-fluoro subunit, a 2'-O-[2-(N-methylcarbamoyl)ethyl] subunit, or a morpholino subunit.

4. The antisense oligomer compound of claim 1, further comprising an arginine-rich cell-penetrating peptide conjugated to the 3' or the 5' end of the antisense oligomer compound.

5. The antisense oligomer compound of claim 1, wherein the target region comprises SEQ ID NO: 1.

6. The antisense oligomer according to claim 1, wherein a nucleobase of each of the subunits is independently adenine, guanine, thymine, uracil, cytosine, inosine, hypoxanthine, 2,6-diaminopurine, 5-methyl cytosine, C5-propynyl-modified pyrimidines, or 10-(9-(aminoethoxy)phenoxazinyl).

7. A pharmaceutical composition, comprising an antisense oligomer compound according to claim 1.

8. An antisense oligomer compound comprising a sequence of 12 to 40 subunits that specifically hybridizes to a target region spanning an exon/intron junction of human type VII collagen pre-mRNA, said exon/intron junction comprises the splice junction of exon 80/intron 80, wherein the sequence is selected from SEQ ID NOS: 27, 28, 29 or 30.

* * * * *